US010065979B2

(12) United States Patent
Horcajada-Cortes et al.

(10) Patent No.: US 10,065,979 B2
(45) Date of Patent: Sep. 4, 2018

(54) ORGANIC/INORGANIC HYBRID NANOPARTICULATES MADE FROM IRON CARBOXYLATES

(75) Inventors: Patricia Horcajada-Cortes, Trappes (FR); Gérard Ferey, Paris (FR); Christian Serre, Plaisir (FR); Ruxandra Gref, Verrières-le-Buisson (FR); Patrick Couvreur, Villebon-sur-Yvette (FR)

(73) Assignees: CENTRE NATIONAL DE LA RECHERCHE SCIENTIFIQUE-CNRS, Paris (FR); UNIVERSITÉ DE VERSAILLES—SAINT-QUENTIN-EN-YVELINES, Versailles (FR)

( * ) Notice: Subject to any disclaimer, the term of this patent is extended or adjusted under 35 U.S.C. 154(b) by 668 days.

(21) Appl. No.: 12/679,645

(22) PCT Filed: Oct. 1, 2008

(86) PCT No.: PCT/FR2008/001366
§ 371 (c)(1),
(2), (4) Date: May 5, 2010

(87) PCT Pub. No.: WO2009/077670
PCT Pub. Date: Jun. 25, 2009

(65) Prior Publication Data
US 2010/0209354 A1 Aug. 19, 2010

(30) Foreign Application Priority Data
Oct. 1, 2007 (FR) .................................... 07 06873

(51) Int. Cl.
C07F 15/02 (2006.01)

(52) U.S. Cl.
CPC .................................. C07F 15/025 (2013.01)

(58) Field of Classification Search
CPC combination set(s) only.
See application file for complete search history.

(56) References Cited

U.S. PATENT DOCUMENTS

| 4,329,332 | A | 5/1982 | Couvreur et al. |
| 5,648,508 | A | 7/1997 | Yaghi |
| 6,638,494 | B1 | 10/2003 | Pilgrimm |
| 6,929,679 | B2 | 8/2005 | Muller et al. |
| 6,930,193 | B2 | 8/2005 | Yaghi et al. |
| 7,855,299 | B2 * | 12/2010 | Jhung .................... C07F 11/005 556/147 |
| 7,880,026 | B2 * | 2/2011 | Ni .......................... C01G 9/00 204/157.75 |
| 2003/0078311 | A1 | 4/2003 | Muller et al. |
| 2011/0052650 | A1 * | 3/2011 | Morris ..................... A61K 8/02 424/401 |
| 2015/0152123 | A1 * | 6/2015 | Zhou ..................... C07F 15/025 423/351 |

FOREIGN PATENT DOCUMENTS

| WO | WO 2005/003032 A1 | 1/2005 |
| WO | WO 2007/090864 A1 | 8/2007 |
| WO | WO-2007/090864 A1 | 8/2007 |
| WO | WO 2007/091828 | 8/2007 |

OTHER PUBLICATIONS

Lee et al., Crystal Growth & Design, 2008, vol. 8, Nol. 1 296-303 (Published Online: Nov. 20, 2007).*
Serre et al., Chem. Mater. 2004, 16, 2706-2711.*
A. M. Layre et al, "Freeze-drying of Composite Core-Shell Nanoparticles", Drug Development and Industrial Pharmacy vol. 32, 2006, 839-246.
A. M. Layre et al, "Nanoencapsulation of a crystalline drug", Int Journal of Pharmaceutics, 298, 2005, 323-327.
A. M. Layre et al, "Novel composite core-shell nanoparticles as busulfan carriers", Journal of Controlled Release vol. 111, 2006, 271-280.
A. Pichon et al., "Solvent-free synthesis of a microporous metal-organic framework", Cryst. Eng. Comm. 8, 2006, 211-214.
A. Shiotani et al., "Die Pd-katalysierte oxidative Kupplungsreaktion von Methylbenzoesauremethylester" 1994, 49, 12, 1731-1736.
A.K. Gupta et al., "Recent advances on surface engineering of magnetic iron oxide nanoparticles and their biomedical applications", Nanomed. 2007, 2(1), 23-39.
A.M. Badawi et al., "Surface and biocidal activity of some synthesized metallo azobenzene isothiouronium salts", Bioorg. Med. Chem., 14, 2006, 8661.
Ameerunisha et al., "Characterization of simple photoresponsive systems and their applications to metal ion transport", J. Chem. Soc. Perkin Trans. 2, 1679, 1995.
B. Baleux et al., "Chimie analytique-dosage colorimétrique d'agents de surface non ioniques polyoxyéthylènes à l'aide d'une solution iode-iodurée", C.R. Acad. Sciences Paris, 1972, série C, 274, 1617-1620.
B. Stella et al., "Biological characterization of folic acid-conjugated poly(H2NPEGCA-co-HDCA) nanoparticles in cellular models", J Drug Target. 2007, 15(2), 146-153.
C Serre et al, "A Route to the synthesis of trivalent transition metal porous carboxylates with trimeric secondary building units", Angew Chme Int vol. 43, 2004, 6285-6289.
C. S. Cundy, "Microwave Techniques in the Synthesis and Modification of Zeolite Catalysts. A Review", Collect. Czech. Chem. Commum. 1998, 63, 1699.
C. Serre et al., J. Am. Chem. Soc., 2002, 124, 13519-13526.

(Continued)

Primary Examiner — Robert S Cabral
(74) Attorney, Agent, or Firm — Arent Fox LLP

(57) ABSTRACT

The invention relates to nanoparticles made from organometallic hybrid materials made from iron carboxylates, used for example as contrast agents. The particles can also be used for the encapsulation and vectoring of molecules of interest such as active3 pharmaceutical agents, cosmetically interesting compounds and markers. Apart from the intrinsic properties thereof for imaging, said nanoparticles give good results in terms of capacity for loading with medicaments and in biocompatibility.

5 Claims, 21 Drawing Sheets

(56) References Cited

OTHER PUBLICATIONS

C. Serre, C. Mellot-Draznieks, S. Surblé, N. Audebrand, Y. Fillinchuk and G. Férey: Science, 2007, 315, 1828.
C.T. Dziobkowski et al., "Magnetic Properties and Mossbauer Spectra of Several Iron(III)-Dicarboxylic Acid Complexes", Inorg. Chem., 1981, 20, 671-678.
D. Braga et al., "Mechanochemical preparation of molecular and supramolecular organometallic materials and coordination networks", Dalton Trans., 2006, 1249-1263.
D. Braga et al., "Simple and Quantitative Mechanochemical Preparation of a Porous Crystalline Material Based on a 1D Coordination Network for Uptake of Small Molecules", Angew. Chem. Int. Ed. 45, 2006, 142-146.
G. Férey et al, "A Chromium Terephtalate-based solid with unusually large pore volumes and surface area", Science vol. 309, 2005, 2040-2042.
G. Oros et al., "Separation of the strength and selectivity of the microbiological effect of synthetic dyes by spectral mapping technique", Chemosphere 52, 2003, 185-193.
G. Tompsett et al., "Microwave Synthesis of Nanoporous Materials", ChemPhysChem. 2006, 7, 296-319.
J. Bouligand et al., "Busulfan-loaded long-circulating nanospheres, a very attractive challenge for both galenists and pharmacologists", Int. J. Microencapsulation., 24:8, 715-730, 2004.
J.H. Van Steenis et al., "Preparation and characterization of folate-targeted pEG-coated pDMAEMA-based polyplexes", J Control Release 87 (2003), pp. 167-176.
K. Byrappa et al., "Handbook of hydrothermal technology", Noyes Publications, Parkridge, New Jersey USA, William Andrew Publishing, LLC, Norwich NY USA, 2001.
K. Luker et al., "Applications of bioluminescence imaging to antiviral research and therapy: Multiple luciferase enzymes and quantitation", Antiviral Research, vol. 78, Issue 3, Jun. 2008, pp. 179-187.
L. Anzalone et al., "Substituent Effects on Hydrogenation of Aromatic Rings: Hydrogenation vs. Hydrogenolysis in Cyclic Analogues of Benzyl Ethers", J. Org. Chem., 1985, 50, 2128-2133.
Lee et al., "Covalent Metal—Peptide Framework Compounds That Extend in One and Two Dimensions", Crystal Growth & Design, 2008, 8(1), 296-303.
M. Hasaan et al., "A phase II trial of liposomal busulphan as an intravenous myeloablative agent prior to stem cell transplantation: 500 mg/m($\wedge$2) as a optimal total dose for conditioning", Bone Marrow Transplant. 2002, 30 (12), 833-841.
Mulder et al., "Magnetic and fluorescent nanoparticles for multimodality imaging", Nanomed. 2007, 2(3), 307-324.
N. Kohler et al., "A bifunctional poly(ethylene glycol) silane immobilized on metallic oxide-based nanoparticles for conjugation with cell targeting agents." J Am Chem Soc 2004; 126: 7206-7211.
P. Caravan, "Strategies for increasing the sensitivity of gadolinium based MRI contrast agents", Chem. Soc. Rev., 2006, 35, 512-523.
P. Chan et al., "Synthesis and characterization of chitosan-g-poly-(ethylene glycol)-folate as a non-viral carrier for tumor-targeted gene delivery", Biomaterials, vol. 28, Issue 3, 2007, pp. 540-549.
P. Couvreur et al, "Nanotechnologies for drug delivery: Application to Cancer and Autoimmune Diseases", Progress in Solid State Chemistry vol. 34, 2006, 231-235.
R. Gref et al. "Surface-engineered nanoparticles for multiple ligand coupling", Biomaterials, 24 (2003), 4529-4537.
R. Gref et al., "Biodegradable long-circulating polymeric nanospheres", Science vol. 263, 1994, 1600-1603.
R. Gref et al., "'Stealth' corona-core nanoparticles surface modified by polyethylene glycol (PEG): influences of the corona (PEG chain length and surface density) and of the core composition on phagocytic uptake and plasma protein adsorption", Colloids and Surfaces B: Biointerfaces, 2000, 18, 3-4 301-313.
Roch et al., "Theory of proton relaxationinduced by superparamagnetic particles", J Chem Phys 110, 5403-5411, 1999.
S. Balthasar et al., "Preparation and characterisation of antibody modified gelatin nanoparticles as drug carrier system for uptake in lymphocytes", Biomaterials, 2005, 26, 15, 2723-2732.
S. C. Wuang et al., "Synthesis and functionalization of polypyrrole-Fe3O4 nanoparticles for applications in biomedicine", Journal of Materials Chemistry vol. 17, 2007, 3354-3362.
S.-E. Park et al., "Supramolecular interactions and morphology control in microwave synthesis of nanoporous materials", Catal. Survey Asia 2004, 8, 91.
Sung Hwa Jhung et al., "Microwave Synthesis of Chromium Terephthalate MIL-101 and Its Benzene Sorption Ability", Adv. Mater, 2007, 19(1), 121-124.
T. Loiseau et al., C.R. Chimie, 2005, 8, 765-772.
W-J. Tsai et al., "Selective COX-2 inhibitors. PArt 1: Synthesis and bilolgical evaluation of phenylazobenzenesulfonamides", Bioorg. Med. Chem. Letters 16, 2006, 4440-4443.
Y. Hattori et al., "Folate-Linked Lipid-Based Nanoparticle for Targeted Gene Delivery", Curr Drug Deliv. 2005, 2(3), 243-252.
Y. Kim et al., "Ultra-photostable n-type PPVs", Chem. Commun., 2005, 372-374.
Yan-Ping Ren et al., Angew. Chem. Int. Ed. 2003, 42, No. 5, 532.
Whitfield, Tabatha R. et al: "Metal-organic frameworks based on iron oxide octahedral chains connected by benzenedicarboxylate dianions" Solid State Sciences, 7(9), 1096-1103 CODEN: SSSCFJ; ISSN: 1293-2558, 2005.
Mellot-Draznieks, Caroline et al: "Very Large Swelling in Hybrid Frameworks: A Combined Computational and Powder Diffraction Study" Journal of the American Chemical Society, 127(46), 16273-16278 CODEN: JACSAT; ISSN: 0002-7863, 2005.
Horcajada, Patricia et al: "Synthesis and catalytic properties of MIL-100 (Fe), an iron (III) carboxylate with large pores" Chemical Communications (Cambridge, United Kingdom), (27), 2820-2822 CODEN: CHCOFS; ISSN: 1359-7345, 2007.
Eddaoudi, Mohamed et al: "Geometric requirements and examples of important structures in the assembly of square building blocks" Proceedings of the National Academy of Sciences of the United States of America, 99(8), 4900-4904 CODEN: PNASA6; ISSN: 0027-8424, 2002.
Surble, Suzy et al: "A new isoreticular class of metal-organic-frameworks with the MIL-88 topology" Chemical Communications (Cambridge, United Kingdom), (3), 284-286 CODEN: CHCOFS; ISSN: 1359-7345, 2006.
Millange, F. et al: "Towards the reactivity of MIL-53 or FeIII(OH)0.8F0.2[02C—C6H4—C02] versus lithium" retrieved from STN Database accession No. 2008:428343 abstract & Studies in Surface Science and Catalysis, 170B (From Zeolites to Prous MOF Materials), 2037-2041 CODEN: SSCTDM; ISSN: 0167-2991, 2007.
Llewellyn, Philip L. et al: "High Uptakes of C02 and CH4 in Mesoporous Metal-Organic Frameworks MIL-100 and MIL-101" Langmuir ACS ASAP CODEN: LANGD5; ISSN: 0743-7463, Mar. 21, 2008 (Mar. 21, 2008).
Choi, Sang Beom et al: "A porous and interpenetrated metal-organic framework comprising tetranuclear ironIII-oxo clusters and tripodal organic carboxylates and its implications for (3,8)-coordinated networks" Crystal Growth & Design, 7(11), 2290-2293 CODEN: CGDEFU; ISSN: 1528-7483, 2007.
Horcajada, Patricia et al: "MOFS as new materials for drug delivery" retrieved from STN Database accession No. 2008:389294 abstract & Abstracts of Papers, 235th ACS National Meeting, New Orleans, LA, United States, Apr. 6-10, 2008, INOR-828 Publisher: American Chemical Society, Washington, D. C. CODEN: 69KNN3, 2008.
Horcajada, Patricia et al: "Metal-organic frameworks as efficient materials for drug delivery" Angewandte Chemie, International Edition, 45(36), 5974-5978 CODEN: ACIEF5; ISSN: 1433-7851, 2006.

* cited by examiner

ORGANIC/INORGANIC HYBRID NANOPARTICULATES MADE FROM IRON CARBOXYLATES

CROSS-REFERENCE TO RELATED APPLICATION

This application is a National Stage entry of International Application No. PCT/FR2008/001366, filed Oct. 1, 2008, which claims priority to French Application No. 07/06873, filed Oct. 1, 2007, the entire specification claims and drawings of which are incorporated herewith by reference.

TECHNICAL FIELD

The present invention relates to nanoparticles of an isoreticular crystalline porous metal-organic framework (MOF), and also, notably, to a process for preparing them.

The MOF nanoparticles of the present invention may be used, for example, as contrast agents and/or as nanoparticles for carrying pharmaceutical compounds.

The nanoparticles of the present invention may also be used for applications in the cosmetics field. They may also be used for vectorizing and/or monitoring pharmaceutical compounds in a body.

The references between square brackets [X] refer to the list of references at the end of the examples.

STATE OF THE ART

Metal-organic frameworks (MOF) are inorganic-organic hybrid framework coordination polymers comprising metal ions and organic ligands coordinated to the metal ions. These materials are organized in one-, two- or three-dimensional frameworks in which the metal clusters are periodically connected together via spacer ligands. These materials have a crystalline structure, are usually porous and are used in many industrial applications such as gas storage, liquid adsorption, liquid or gas separation, catalysis, etc.

An example that may be mentioned is U.S. patent application Ser. No. 10/039,733 [1], which describes a reaction process involving a catalyst system comprising a zinc-based MOF material. This same material is also used for storing gas in U.S. patent application Ser. No. 10/061,147 [2].

In addition, MOF materials based on frameworks of the same topology are termed "isoreticular". These spatially organized frameworks have made it possible to obtain more uniform porosity. Thus, U.S. patent application Ser. No. 10/137,043 [3] describes several zinc-based IRMOF (Iso-Reticular Metal-Organic Framework) materials used for gas storage.

However, nanoparticles are difficult to synthesize, and especially nanoparticles smaller than 1000 nm, given their nature to aggregate readily and given the tendency of these materials to organize in crystal lattices of large size (microns). This also leads to problems of non-uniformity of particle size, which are unfavorable for certain applications.

Furthermore, the structure of these materials and the topology of the constituent elements have not really been studied in the prior art. In addition, the structures are not always controlled so as to obtain specific properties such as a "custom" pore size suited to the molecules to be adsorbed, a flexible or rigid structure, an improved specific surface area and/or adsorption capacity, etc. Specifically, it is difficult to control the structural organization and the porosity of these materials.

One of the reasons for the difficulty in controlling the structural organization is linked to the risks of interpenetration of the frameworks. Specifically, during the formation or polymerization of the materials, frameworks may become interlaced. Increasing the number of interpenetrated frameworks leads to a denser material with smaller pores, resulting in a non-uniform structure with unsuitable, heterogeneous porosity.

Thus, "modeling" agents have been used to obtain "controlled" structures as described in U.S. Pat. No. 5,648,508 [4]. The ligands organize around the metal by encapsulating these "modeling" agents in cavities or pores. However, these agents interact strongly with the MOF material, making it difficult or even impossible to remove them without damaging the framework, thus leading to a solid whose pores are already occupied by these agents.

However, the use of these agents adds chemical material during the synthesis of the particles, which makes the process more complex and more expensive. In addition, for medical applications, this modeling appears to be poorly adaptable.

Many improvements thus remain to be made in terms of controlling the structure and size of the particles so as to obtain materials that are suitable for each application, with suitable and uniform porosities, particle sizes and loading capacities.

Moreover, studies of the dynamics of molecular processes, the localization of molecules and visualization of the molecular interactions inside a living cell or body are nowadays possible by virtue of the development of molecular imaging methods. In addition, Magnetic Resonance Imaging (MRI) is a powerful and non-invasive technique of medical diagnosis for obtaining three-dimensional images with great precision. This technique thus finds many applications, from the detection and monitoring of diseases (such as cancer) to the development of targeted and personalized treatments; however, it is also increasingly used by the pharmaceutical industries for the development of medicaments (study of delivery of active principles, measurement of the efficacy of vectors, etc).

The use of specific or nonspecific contrast agents is, however, necessary to improve the signal intensity and the image contrast.

Contrast agents are characterized by their relaxivity. The greater the relaxivity, the greater the effect of the contrast agents. The relaxivity corresponds to the capacity of contrast agents to modify the relaxation times of the protons of the water of the medium following the application of a magnetic field. It depends on the paramagnetic properties of the metals used, but also on the amount and mobility of the water molecules that are coordinated to the metal in the first inner sphere, making the greatest contribution, and also in the outer sphere. These "coordination spheres" represent the atoms immediately attached to the metallic center in the case of the first sphere; for the outer sphere, this represents the atoms immediately located beyond the first sphere.

Thus, for the gadolinium-based contrast agents, the inner sphere contribution results from the chemical exchange of a water molecules between the first coordination sphere of the paramagnetic ion and of the solvent. According to the Solomon-Bloembergen-Morgan theory, it depends on several characteristic times:

T1 and T2, the longitudinal and transverse electronic relaxation times of the protons of water, the residence time of a water molecule in the first coordination sphere of the cation, the rotational correlation time $\tau_R$.

The more water molecules there are coordinated to the metal, the more the relaxation time decreases, which has the consequence of increasing the signal.

The contrast agents commonly used are generally the gadolinium (III) paramagnetic ion, which has favourable magnetic and electronic properties with a slow electronic relaxation at the scale of the movements of water in biological tissues. In free form, the $Gd^{3+}$ ion is highly toxic, which accounts for the use of gadolinium complexes that must be stable enough to avoid dissociation of the complex.

Thus, the commercial contrast agents are gadolinium polyaminocarboxylate complexes, which are highly stable relative to the dissociation of the ligand. However, they have low relaxivity and are not specific.

Iron oxides, as described in U.S. Pat. No. 6,638,494 [5], are also used, but generally have insufficient magnetic properties with poor MRI contrast effects.

Furthermore, drawbacks associated with the instability of these compounds, their aggregation, the inhomogeneity of the particles or the poor crystal properties persist, giving rise to problems of toxicity, incompatibility, degradability, solubility, distribution, non-specificity, etc.

There is thus a real need to use particles of uniform size, which have good properties in imaging and which are nontoxic, stable, biocompatible and biodegradable, and/or which have suitable solubility and crystal characteristics, etc.

Moreover, the use of carriers and vectors for molecules of interest, especially molecules with a therapeutic effect or markers, has become a major issue for the development of novel diagnostic methods or novel medicaments. Specifically, the molecules of interest have characteristics that have an influence on the pharmacokinetics and biodistribution of these molecules and that are not always favorable or adaptable to the medium into which they are introduced. They are, for example, physicochemical characteristics, such as instability, a strong tendency toward crystallization, poor water solubility and/or biological characteristics such as toxicity, biodegradability, etc.

By way of example, many anticancer agents have a therapeutic index that is limited by their high cytotoxic activity.

The therapeutic index may also be limited by poor solubility and a strong tendency toward crystallization of the active principles. This may not only lead to slowing-down of the dissolution and absorption of the active principles, but also to a risk of partial or total vascular obstruction via the formation of crystalline particles in situ after administration. This is especially the case for alkylating anticancer agents such as busulfan, which contain chemical groups that have a strong tendency to self-associate, via hydrophobic or polar interactions leading to spontaneous crystallization of these molecules. It is therefore important to avoid this crystallization phenomenon, for example during the vectorization of such active principles.

The instability of active principles also poses a problem of therapeutic efficacy. Specifically, certain principles are rapidly eliminated by the immune system or taken up by the organs of the reticulo-endothelial system (mainly the liver and the spleen). This is especially the case for busulfan, which is predominantly taken up by the liver within 10 to 30 minutes of oral or intravenous administration and which may be responsible for the onset of veno-occlusive liver disease, for which no treatment exists.

Thus, various materials, for instance liposomes or various polymers have been developed for carrying active compounds. In particular, "furtive" vectors, which are poorly recognized by the immune system and/or capable of avoiding uptake by these organs, have been developed in order to encapsulate and/or vectorize unstable and/or toxic active principles.

The article Bone Marrow Transplant. 2002, 30 (12), 833-841 [6] describes, for example, colloidal vectors, especially loaded with busulfan. Unfortunately, the degree of encapsulation of the busulfan is low, barely reaching 0.5% by weight relative to the total weight of liposomes. Furthermore, such liposome-based colloidal vectors have a short lifetime in plasmatic medium due to spontaneous dissociation and to rapid metabolic degradation of these lipid structures. This entails poor therapeutic efficacy and large liposomal dispersion volumes, which are occasionally incompatible with the necessary treatment dosages.

To overcome this problem of intra-plasmatic stability, solid colloidal vectors based on water-insoluble polymers have been developed. They are in the form of biodegradable polymer nanoparticles and the active principles they may carry are gradually released, by diffusion and/or gradually as the nanoparticles are metabolically degraded. This is the case for polymers of the poly(alkyl cyanoacrylate) family, as described in U.S. Pat. No. 4,329,332 [7], which are used for carrying toxic and/or unstable products.

However, these nanoparticles have a poor degree of encapsulation. In addition, the degree of encapsulation depends on the nature of the active principle to be encapsulated in the poly(alkyl cyanoacrylate) nanoparticles. Specifically, in the case of crystalline active principles, sparingly soluble in water and/or hydrophobic, they have a tendency to precipitate and to crystallize in the dispersing aqueous phase of the in situ polymerization process used for obtaining these nanoparticles. This makes the encapsulation of such active principles difficult, with poor degrees of encapsulation of poly(alkyl cyanoacrylate) nanoparticles, of the order of 0.1% to 1% by weight of the mass of polymer employed.

Furthermore, such vectors are poorly suited to the encapsulation of highly reactive active principles, for instance busulfan. Specifically, insofar as these vectors are manufactured by in situ polymerization in the presence of the active principle, said active principle runs the risk of reacting with the monomer units, preventing adequate polymerization necessary for the production of the nanoparticles.

Thus, many molecules remain difficult or even impossible to encapsulate on account of their tendency toward crystallization, their poor solubility in solvents and/or their instability.

In addition, busulfan poses a real challenge with respect to its encapsulation. Furtive vectors that avoid the liver have not made it possible to achieve satisfactory encapsulation objectives due to the small possible loading with busulfan. The maximum loading obtained with liposomes does not exceed 0.5% by weight.

More recently, the use of poly(alkyl cyanoacrylate)-based biodegradable polymer nanoparticles has made it possible to improve the degree of encapsulation of busulfan up to about 5% by weight, as described in J. Bouligand, et al., *Int. J. Pharm.*, 2004 [8]. However, during repeated administration of the nanoparticles, a large accumulation of polymers in the body may be dramatic, for example in high-dose chemotherapy.

There is therefore a real need for novel compounds that are capable of carrying active principles, notably active principles that have particular encapsulation difficulties linked to their instability, their strong tendency to crystallize, their poor solubility, their amphiphilic or hydrophilic nature, etc. In addition, there is a need for novel compounds with sufficient loading capacities, especially if repeated administration of nanoparticles is envisioned.

Furthermore, there is a real need for compounds that can afford controlled release of the active principles.

Furthermore, there is a real need for compounds that are capable of vectorizing active principles toward specific targets, or of modifying the biodistribution of these active principles.

DESCRIPTION OF THE INVENTION

The aim of the present invention is, precisely, to meet these needs and drawbacks of the prior art by providing isoreticular porous crystalline MOF nanoparticles comprising a three-dimensional succession of units corresponding to formula (I) below:

   Formula (I)

in which:

Fe represents the metallic ion $Fe^{3+}$ or $Fe^{2+}$, preferably $Fe^{3+}$;

m is 1 to 4, for example 1 or 3;

k is 0 to 4, for example 0 or 1;

l is 0 to 4, for example 0 or 1;

p is 1 to 4, for example 1 or 3;

X is a ligand chosen from the group comprising $OH^-$, $Cl^-$, $F^-$, $I^-$, $Br^-$, $SO_4^{2-}$, $NO_3^-$, $ClO_4^-$, $PF_6^-$, $BF_3^-$, $R^1$—$(COO)_n^-$, $R^1$—$(SO_3)_n^-$, $R^1$—$(PO_3)_n^-$, in which $R^1$ is a hydrogen atom, an optionally substituted linear or branched $C_1$ to $C_{12}$ alkyl, n=1 to 4;

L is a spacer ligand comprising a radical R bearing q carboxylate groups

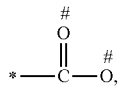

in which q is 1, 2, 3, 4, 5 or 6; for example 2 to 4;

* denotes the point of attachment of the carboxylate to the radical R;

# denotes the possible points of attachment of the carboxylate to the metal ion;

R represents:
(i) a $C_{1-12}$alkyl, $C_{2-12}$alkene or $C_{2-12}$alkyne radical;
(ii) a fused or non-fused monocyclic or polycyclic aryl radical, comprising 6 to 50 carbon atoms;
(iii) a fused or non-fused monocyclic or polycyclic heteroaryl, comprising 1 to 50 carbon atoms;
(iv) an organic radical comprising a metal element chosen from the group comprising ferrocene, porphyrin, phthalocyanin and a Schiff's base $R^{X1}R^{X2}$—C=N—$R^{X3}$,
in which $R^{X1}$ and $R^{X2}$ are independently a hydrogen atom, a linear, branched or cyclic, optionally substituted $C_{1-12}$alkyl, $C_{2-12}$alkene or $C_{2-12}$alkyne radical, or an optionally branched and/or substituted monocyclic or polycyclic aryl comprising 6 to 50 carbon atoms;
and $R^{X3}$ is a linear, branched or cyclic, optionally substituted $C_{1-12}$alkyl, $C_{2-12}$alkene or $C_{2-12}$alkyne radical, or an optionally branched and/or substituted monocyclic or polycyclic aryl comprising 6 to 50 carbon atoms;

the radical R being optionally substituted with one or more groups $R^2$ independently chosen from the group comprising $C_{1-10}$alkyl; $C_{2-10}$alkene; $C_{2-10}$alkyne; $C_{3-10}$cycloalkyl; $C_{1-10}$heteroalkyl; $C_{6-10}$aryl; $C_{3-10}$heteroaryl; $C_{5-20}$heterocycle $C_{1-10}$alkyl$C_{6-10}$aryl; $C_{1-10}$alkyl$C_{3-10}$heteroaryl; $C_{1-10}$alkoxy; $C_{6-10}$aryloxy; $C_{3-10}$heteroalkoxy; $C_{3-10}$heteroaryloxy; $C_{1-10}$alkylthio; $C_{6-10}$arylthio; $C_{1-10}$heteroalkylthio; $C_{3-10}$-heteroarylthio; F; Cl; Br; I; —$NO_2$; —CN; —$CF_3$; —$CH_2CF_3$; —$CHCl_2$; —OH; —$CH_2OH$; —$CH_2CH_2OH$; —$NH_2$; —$CH_2NH_2$; —NHCOH; —COOH; —$CONH_2$; —$SO_3H$; —$CH_2SO_2CH_3$; —$PO_3H_2$; —$B(OR^{G1})_2$; or a function -$GR^{G1}$ in which G is —O—, —S—, —$NR^{G2}$—, —C(=O)—, —S(=O)—; —$SO_2$—; —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}$$SO_2$—, —C(=$NR^{G2}$)$NR^{G3}$—, —OC(=$NR^{G2}$)—, —$NR^{G2}$C(=$NR^{G3}$)—, —$NR^{G2}$$SO_2$—, —$NR^{G2}$$SO_2$$NR^{G3}$—, —$NR^{G2}$C(=S)—, —SC(=S)$NR^{G2}$—, —$NR^{G2}$C(=S)S—, —$NR^{G2}$C(=S)$NR^{G2}$—, —SC(=$NR^{G2}$)—, —C(=S)$NR^{G2}$—, —OC(=S)$NR^{G2}$—, —$NR^{G2}$C(=S)O—, —SC(=O)$NR^{G2}$—, —$NR^{G2}$C(=O)S—, —C(=O)S—, —SC(=O)—, —SC(=O)S—, —C(=S)O—, —OC(=S)—, —OC(=S)O— or —$SO_2NR^{G2}$—, in which each occurrence of $R^{G1}$, $R^{G2}$ and $R^{G3}$ is, independently of the other occurrences of $R^{G1}$, a hydrogen atom; a halogen atom; or a linear, branched or cyclic, optionally substituted $C_{1-12}$alkyl, $C_{1-12}$heteroalkyl, $C_{2-10}$alkene or $C_{2-10}$alkyne group; or a group $C_{6-10}$aryl, $C_{3-10}$heteroaryl, $C_{5-10}$heterocycle, $C_{1-10}$alkyl$C_{6-10}$aryl or $C_{1-10}$alkyl$C_{3-10}$heteroaryl in which the aryl, heteroaryl or heterocyclic radical is optionally substituted; or alternatively, when G represents —$NR^{G2}$—, $R^{G1}$ and $R^{G2}$ together with the nitrogen atom to which they are attached form an optionally substituted heterocycle or heteroaryl.

In the context of the present invention, the various occurrences of Fe in the units of formula (I) may be identical or different. Thus, the expression "Fe represents metal ion $Fe^{3+}$ or $Fe^{2+}$" featured hereinabove and in the present document is equivalent to the expression: "each occurrence of Fe independently represents the metal ion $Fe^{3+}$ or $Fe^{2+}$".

The term "nanoparticle" refers to a particle smaller than 1 µm in size. In particular, the solid MOF nanoparticles according to the invention may have a diameter of less than 1000 nanometers, preferably less than 500 nm, more preferably less than 250 nm and most particularly less than 100 nm.

The term "substituted" denotes, for example, the replacement of a hydrogen radical in a given structure with a radical $R^2$ as defined previously. When more than one position may be substituted, the substituents may be the same or different in each position.

For the purposes of the present invention, the term "spacer ligand" refers to a ligand (including, for example, neutral species and ions) coordinated to at least two metals, which participates in providing distance between these metals and in forming empty spaces or pores. The spacer ligand may comprise 1 to 6 carboxylate groups, as defined previously, which may be monodentate or bidentate, i.e. possibly comprising one or two points of attachment to the metal. The points of attachment to the metal are represented by the sign # in the formulae. When the structure of a function A comprises two points of attachment #, this means that the coordination to the metal may take place via one, the other or both the points of attachment.

For the purposes of the present invention, the term "alkyl" refers to a linear, branched or cyclic, saturated or unsaturated, optionally substituted carbon-based radical, comprising 1 to 12 carbon atoms, for example 1 to 10 carbon atoms, for example 1 to 8 carbon atoms, for example 1 to 6 carbon atoms.

For the purposes of the present invention, the term "alkene" refers to an alkyl radical as defined previously, containing at least one carbon-carbon double bond.

For the purposes of the present invention, the term "alkyne" refers to an alkyl radical, as defined previously, containing at least one carbon-carbon triple bond.

For the purposes of the present invention, the term "aryl" refers to an aromatic system comprising at least one ring that satisfies Hückel's aromaticity rule. Said aryl is optionally substituted and may comprise from 6 to 50 carbon atoms, for example 6 to 20 carbon atoms, for example 6 to 10 carbon atoms.

For the purposes of the present invention, the term "heteroaryl" refers to a system comprising at least one 5- to 50-membered aromatic ring, among which at least one member of the aromatic ring is a heteroatom, chosen especially from the group comprising sulfur, oxygen, nitrogen and boron. Said heteroaryl is optionally substituted and may comprise 1 to 50 carbon atoms, preferably 1 to 20 carbon atoms, preferably 3 to 10 carbon atoms.

For the purposes of the present invention, the term "cycloalkyl" refers to a saturated or unsaturated, optionally substituted cyclic carbon-based radical, which may comprise 3 to 20 carbon atoms, preferably 3 to 10 carbon atoms.

For the purposes of the present invention, the term "haloalkyl" refers to an alkyl radical as defined previously, said alkyl system comprising at least one halogen.

For the purposes of the present invention, the term "heteroalkyl" refers to an alkyl radical as defined previously, said alkyl system comprising at least one heteroatom, chosen especially from the group comprising sulfur, oxygen, nitrogen and boron.

For the purposes of the present invention, the term "heterocycle" refers to a saturated or unsaturated, optionally substituted cyclic carbon-based radical comprising at least one heteroatom, and which may comprise 2 to 20 carbon atoms, preferably 5 to 20 carbon atoms, preferably 5 to 10 carbon atoms. The heteroatom may be chosen, for example, from the group comprising sulfur, oxygen, nitrogen and boron.

For the purposes of the present invention, the terms "alkoxy", "aryloxy", "heteroalkoxy" and "heteroaryloxy" refer to, respectively, an alkyl, aryl, heteroalkyl or heteroaryl radical, linked to an oxygen atom.

For the purposes of the present invention, the terms "alkylthio", "arylthio", "heteroalkylthio" and "heteroarylthio" refer to, respectively, an alkyl, aryl, heteroalkyl or heteroaryl radical linked to a sulfur atom.

The term "Schiff's base" refers to a functional group that contains a double bond C=N, of general formula $R^{X1}R^{X2}-C=N-R^{X3}$, with $R^{X1}$, $R^{X2}$ and $R^{X3}$ as defined previously.

The term "three-dimensional structure" refers to a three-dimensional succession or repetition of units of formula (I) as is conventionally understood in the field of MOF materials, which are also characterized as "metallo-organic polymers".

Unless otherwise indicated, the various embodiments that follow concerning MOF materials apply equally to the abovementioned use and process of the invention.

The MOF nanoparticles according to the invention have the advantage of having a controlled crystal structure, with a particular topology and distribution, which affords these materials specific properties. These specific properties are found in the nanoparticles prepared from various forms mentioned above of the MOF solid of the present invention.

The MOF nanoparticles according to the invention may comprise octahedral trivalent iron atoms, with an oxidation state of +3 and a coordination number of 6.

The term "coordination number" refers to the number of bonds for which the two electrons shared in the bond originate from the same atom. The electron-donating atom acquires a positive charge, while the electron-accepting atom acquires a negative charge.

In addition, the metal atoms may be isolated or grouped into metal "clusters". The MOF nanoparticles according to the invention may be constructed, for example, from octahedral chains or of trimers of octahedra. For example, the MOF nanoparticles according to the invention may be formed from iron carboxylate MOF materials constructed from octahedral chains linked via apices or edges or octahedral trimers connected via a central oxygen atom.

For the purposes of the present invention, the term "metal cluster" refers to a group of atoms containing at least two metals linked via ionocovalent bonds, either directly via anions, for example O, OH, Cl, etc., or via the organic ligand.

Furthermore, the MOF nanoparticles according to the invention may be in various forms or "phases", given the various possibilities for organization and connection of the ligands to the metal or to the metal group.

For the purposes of the present invention, the term "phase" refers to a hybrid composition comprising at least one metal and at least one organic ligand having a defined crystal structure.

The crystalline spatial organization of the nanoparticles of the present invention is the basis of the particular characteristics and properties of these materials, and especially governs the pore size, which has an influence on the specific surface area of the materials and on the adsorption characteristics, but also the density of the materials, this density being relatively low, the proportion of metal in these materials, the stability of the materials, the rigidity and flexibility of the structures, etc.

In addition, the pore size may be adjusted by choosing appropriate spacer ligands.

In one embodiment, the ligand L of the unit of the formula (I) of the MOF solids of the present invention may be a di-, tri-, tetra- or hexacarboxylate ligand chosen from the group comprising:

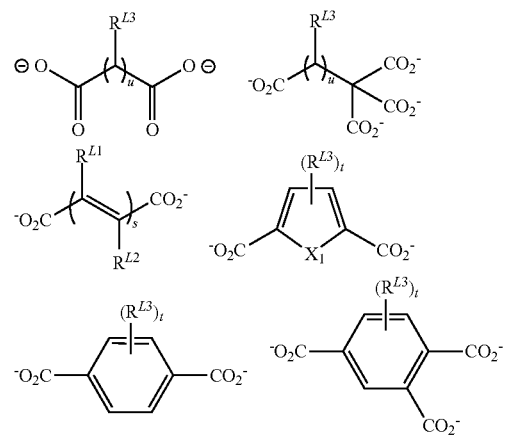

-continued

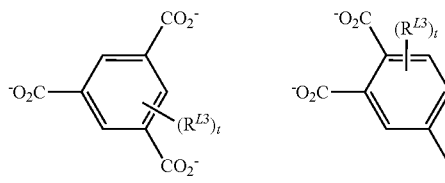

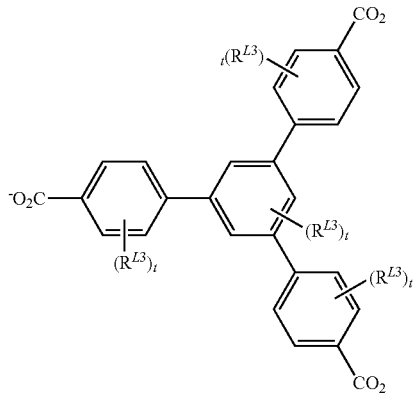

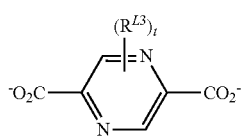

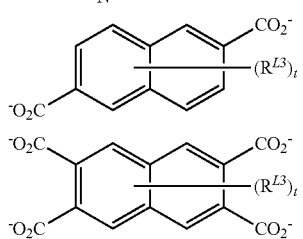

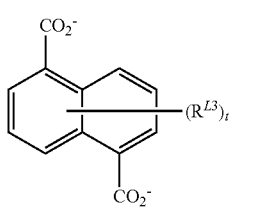

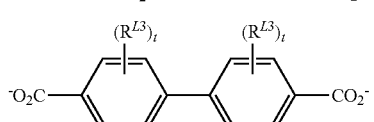

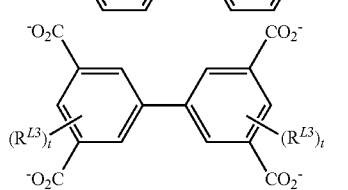

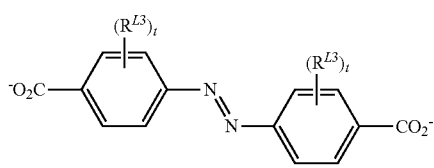

-continued

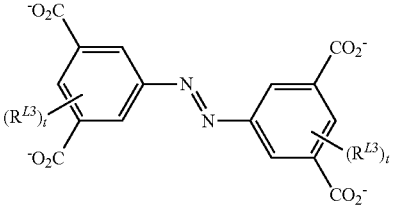

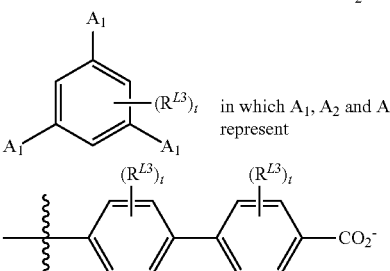

in which $A_1$, $A_2$ and $A_3$ independently represent in which:
$X_1$ represents O or S,
s represents an integer from 1 to 4,
each occurrence of t independently represents an integer from 1 to 4,
u represents an integer from 1 to 7,
$R^{L1}$ and $R^{L2}$ independently represent H, a halogen or a $C_1$ to $C_6$ alkyl (preferably methyl or ethyl), and
each occurrence of $R^{L3}$ independently represents H, a halogen (preferably F, Cl or Br), OH, $NH_2$, $NO_2$ or a $C_1$ to $C_6$ alkyl (preferably methyl or ethyl).

In particular, the ligand L of the unit of formula (I) of the present invention may be a di-, tri- or tetracarboxylate ligand chosen from the group comprising: $C_2H_2(CO_2^-)_2$ (fumarate), $C_2H_4(CO_2^-)_2$ (succinate), $C_3H_6(CO_2^-)_2$ (glutarate), $C_4H_4(CO_2^-)_2$ (muconate), $C_4H_8(CO_2^-)_2$ (adipate), $C_7H_{14}(CO_2^-)_2$ (azelate), $C_5H_3S(CO_2^-)_2$ (2,5-thiophenedicarboxylate), $C_6H_4(CO_2^-)_2$ (terephthalate), $C_6H_2N_2(CO_2^-)_2$ (2,5-pyrazinedicarboxylate), $C_{10}H_6(CO_2^-)_2$ (naphthalene-2,6-dicarboxylate), $C_{12}H_8(CO_2^-)_2$ (biphenyl-4,4'-dicarboxylate), $C_{12}H_8N_2(CO_2^-)_2$ (azobenzenedicarboxylate), $C_6H_3(CO_2^-)_3$ (benzene-1,2,4-tricarboxylate), $C_6H_3(CO_2)_3$ (benzene-1,3,5-tricarboxylate), $C_{24}H_{15}(CO_2^-)_3$ (benzene-1,3,5-tribenzoate), $C_6H_2(CO_2^-)_4$ (benzene-1,2,4,5-tetracarboxylate), $C_{10}H_4(CO_2^-)_4$ (naphthalene-2,3,6,7-tetracarboxylate), $C_{10}H_4(CO_2^-)_4$ (naphthalene-1,4,5,8-tetracarboxylate), $C_{12}H_6(CO_2^-)_4$ (biphenyl-3,5,3',5'-tetracarboxylate), and modified analogs chosen from the group comprising 2-aminoterephthalate, 2-nitro-terephthalate, 2-methylterephthalate, 2-chloroterephthalate, 2-bromoterephthalate, 2,5-dihydroxoterephthalate, tetrafluoroterephthalate, tetramethylterephthalate, dimethyl-4,4'-biphenyldicarboxylate, tetramethyl-4,4'-biphenyldicarboxylate, dicarboxy-4,4'-biphenyldicarboxylate, 2,5-pyrazinedicarboxylate. The ligand L of the unit of formula (I) of the present invention may also represent 2,5-diperfluoroterephthalate, azobenzene-4,4'-dicarboxylate, 3,3'-dichloroazobenzene-4,4'-dicarboxylate, 3,3'-dihydroxoazobenzene-4,4'-dicarboxylate, 3,3'-diperfluoroazobenzene-4,4'-dicarboxylate, 3,5,3',5'-azobenzenetetracarboxylate, 2,5-dimethylterephthalate, perfluorosuccinate, perfluoromuconate, perfluoroglutarate, 3,5,3',5'-perfluoro-4,4'-azobenzenedicarboxylate, 3,3'-diperfluoroazobenzene-4,4'-dicarboxylate.

Most of the carboxylate ligands listed above are commercially available. The reader may refer to the Examples section for the preparation of the non-commercial carboxylate ligands.

In one embodiment, the ligand L has biological activity. The nanoporous hybrid solids according to the invention have a mineral part, the metal (iron), and an organic part, a ligand with two or more complexing functions (carboxylate, phosphate, amide, etc.). The incorporation of organic ligands that have biological activity has the advantage of allowing controlled release of active molecules as a function of the rate of degradation of the material (these are the abovementioned biologically active ligands that are released during the degradation of the MOF material). Thus, the MOF material itself is "bioactive", i.e. it is capable of releasing components with biological activity.

In addition, the release of these active molecules that form part of the MOF framework may be combined with the release of other active principles encapsulated in the nanoparticles of MOF material according to the invention. This aspect of encapsulation of active principles is described hereinbelow in the present document.

Thus, the present invention also relates to nanoparticles of MOF material comprising biologically active ligands and encapsulating one or more active principles, with potentially complementary or different activity, and to their use for combined therapies. The combined therapy is performed by releasing (i) the active principle encapsulated in the pores of the MOF material and (ii) biologically active ligands incorporated in the framework of the crystalline MOF material.

Many biologically active organic molecules exist comprising complexing functions, which are capable of forming porous hybrid solids according to the present invention.

For example, it may be azelaic acid ($HO_2C(CH_2)_7CO_2H$, a dermatological agent with antineoplastic activity), meprobamate (anticonvulsive, sedative, muscle relaxant, antianxiety agent), aminosalicylic acid (antituberculosis), chlodronate, pamidrontate, alendronate and etidronate (prophylactic saccharide-bearing antineoplastic agent for osteoporosis), azobenzenes (antimicrobial activity, COX inhibitors), porphyrins or amino acids (Lys, Arg, Asp, Cys, Glu, Gln, etc.), dibenzofuran-4,6-dicarboxylic acid (transtryretin inhibitor), dipicolinic acid (dihydrodipicolinate reductase inhibitor), glutamic acid, fumaric acid, succinic acid, suberic acid, adipic acid, nicotinic acid, nicotinamide, purines, pyrimidines, etc.

Mention is made, for example, of the antimicrobial or anti-inflammatory activity (NSAIDs, COX inhibitors) of azobenzenes. In this respect, the reader may refer to the following references: G. Oros, T. Cserhati, E. Forgacs, *Chemosphere* 52, 2003, 185 [ref 35], A. M. Badawi, E. M. S. Azzam, S. M. I. Morsy, *Bioorg. Med. Chem.*, 14, 2006, 8661 [ref 36] and W-J. Tsai, Y-J Shiao, S-J Lin, W-F Chiou, L-C Lin, T-H Yang, C-M Teng, T-S Wu, L-M Yang, *Bioorg. Med. Chem. Letters* 16, 2006, 4440 [ref 37].

Thus, the ligand L may be a biologically active ligand chosen from the group comprising $C_7H_{14}(CO_2^-)_2$ (azelate), aminosalicylate, porphyrins comprising carboxylate groups, amino acids (Lys, Arg, Asp, Cys, Glu, Gln, etc.), azobenzenes comprising carboxylate groups, dibenzofuran-4,6-dicarboxylate, dipicolinate, glutamate, fumarate, succinate, suberate, adipate, and nicotinate.

Most particularly, the ligand L may represent a biologically active ligand chosen from the group comprising $C_7H_{14}(CO_2^-)_2$ (azelate), azobenzenedicarboxylate, glutamate, fumarate, succinate, adipate, amino acids and nicotinate.

Porous hybrid solids based on iron and azobenzene ligands, and the demonstration of their antimicrobial activity, the study of their degradation in physiological media and their activity on cells are described in the "Examples" section.

The anion X of the unit of formula (I) of the present invention may be chosen from the group comprising $OH^-$, $Cl^-$, $Br^-$, $F^-$, $R—(COO)_n^-$, $PF_6^-$, $NO_3^-$, $SO_4^{2-}$ and $ClO_4^-$, with R and n as defined previously.

In particular, the anion X of the unit of formula (I) of the present invention may be chosen from the group comprising $OH^-$, $CH_{13}$, $F^-$, and $CH_3—COO^-$, $PF_6^-$ and $ClO_4^-$, or alternatively a carboxylate ligand chosen from the above list.

In one particular embodiment, the anion X may be chosen from the group comprising $OH^-$, $Cl^-$, $F^-$ and $R—(COO)_n^-$ in which R represents $—CH_3$, $—C_6H_3$, $—C_6H_4$, $—C_{10}H_4$ or $—C_6(CH_3)_4$.

In one embodiment, the anion X may be in an isotopic form suitable for imaging techniques such as positron emission tomography (PET).

Positron emission tomography (PET) is a nuclear medical imaging method that enables three-dimensional measurement of the metabolic activity of an organ by virtue of the emissions produced by positrons originating from the disintegration of a preinjected radioactive product. PET is based on the general principle of scintigraphy, which consists in injecting a tracer whose behavior and biological properties are known, to obtain an image of the functioning of an organ. This tracer is labeled with a radioactive atom (carbon, fluorine, nitrogen, oxygen, etc.) which emits positrons, the annihilation of which itself produces two photons. Detection of the trajectory of these photons by the collimator of the PET camera makes it possible to localize the place of their emission and thus the concentration of the tracer at each point in the organ. It is this quantitative information that is represented in the form of an image presenting in color the areas of high concentration of the tracer.

Thus, PET makes it possible to visualize the metabolic activities of the cells: this is referred to as functional imaging, as opposed to so-called structural imaging techniques such as those based on X-rays (radiology or CT-scan), which are limited to images of the anatomy. Consequently, positron emission tomography is a diagnostic tool that makes it possible to detect certain pathologies that are reflected by an impairment in normal physiology, for instance cancers. PET is also used in biomedical research, for example in cerebral imaging where it enables detection of the active regions of the brain during such and such cognitive activity in a similar manner to that which is performed in functional magnetic resonance imaging.

For example, X may represent $^{18}F^-$, which is a positron emitter and thus allows the use of the MOF nanoparticles of the invention for applications involving PET imaging.

Thus, in one embodiment, in the unit of formula (I), at least one occurrence of the ligand X is $^{18}F^-$.

In one embodiment, the ligand L is a fluoro ligand; i.e. comprising at least one F substituent. For example, it may be a tetrafluoroterephthalate, perfluorosuccinate, perfluoromuconate, perfluoroglutarate, 2,5-diperfluoroterephthalate, 3,6-perfluoro-1,2,4,5-benzenetetracarboxylate, 3,5,3',5'-perfluoro-4,4'-azobenzenedicarboxylate or 3,3'-diperfluoroazobenzene-4,4'-dicarboxylate ligand.

The abovementioned fluoro ligands may be enriched in $^{18}F$ isotope via standard radiosynthesis techniques that are well known to those skilled in the art.

The PET technique makes it possible to obtain very detailed images of living tissue. The fluorine-18 radioisotope ($^{18}$F) (t1/2=110 minutes) is a positron emitter; the positrons emitted are instantly annihilated by the electrons of the surrounding material, and it is the resulting gamma rays that are detected.

Thus, the invention also relates to the use of MOF nanoparticles according to the invention as markers that may be used in medical imaging, such as PET imaging.

Thus, a process is provided for viewing living tissue by PET, comprising administrering MOF solid nanoparticles according to the invention to an individual, and viewing the tissues by PET imaging. In particular, the MOF solid contains at least one 18F fluoro ligand and/or $^{18}$F as counterion (i.e. at least one occurrence of X in the unit of formula (I) represents $^{18}$F), such as those mentioned previously.

Moreover, the presence of fluorine atoms in the MOF solids (in the very framework of the MOF solids (anion X=F), via fluoro ligands L or via the presence of fluoro molecules in the pores or at the surface of the nanoparticles of the invention) makes it possible to envision the use of these MOF solid nanoparticles for applications in medical imaging such as echography.

Thus, the invention also relates to the use of MOF nanoparticles according to the invention for the manufacture of a contrast agent that may be used in medical imaging, especially in echography, echosonography or magnetic resonance imaging.

The development of a contrast agent for echography assumes the introduction into the tissues to be examined of efficient ultrasound reflectors. Since the ideal reflectors are gas microbubbles, it is a matter of injecting a gas into the veins of the patient. When formulated as microbubbles a few microns in diameter, administration of the gas becomes harmless. However, once in the circulation, air microbubbles, under the combined action of the arterial pressure and the Laplace pressure, dissolve in the blood within a few seconds.

Up to now, the use of perfluoro compounds, whose solubility in water is extremely low, has made it possible to formulate injectable microbubbles whose intravascular persistence is sufficient to enable efficient radiological examination. Several contrast agents have just become commercially available; especially based on $C_3F_8$, $SF_6$ or $C_6F_{14}$. These agents make it possible, in particular, to view the endocardial edge and to diagnose structural or functional cardiac anomalies. They also facilitate the viewing of vessels and the detection of perfusion defects, tumors and other lesions.

Fluorocarbons combine exceptional chemical and biological inertness with a high capacity for dissolution of the gases, extreme hydrophobicity and also pronounced lipophobicity. Their very low solubility in water makes it possible to stabilize the injectable microbubbles that serve as contrast agent in echography.

Thus, the MOF nanoparticles according to the present invention, whether surface-modified or not and containing perfluoro molecules, may serve for diagnosis by echosonography or by magnetic resonance imaging.

Thus, a process is provided for diagnosis by echography, echosonography or magnetic resonance imaging, comprising administering MOF solid nanoparticles according to the invention to an individual, and viewing of the tissues by echography, echosonography or magnetic resonance imaging. In particular, the MOF solid contains at least one perfluoro molecule, such as those mentioned previously.

Furthermore, as discussed hereinbelow, the particular structural characteristics of the MOF solids forming the nanoparticles of the present invention, especially in terms of flexibility or pore size, make them adsorbents with a high loading capacity, of high selectivity and high purity. They thus enable the adsorption of fluoro molecules, for instance fluorocarbons, with a favorable energy cost and a longer release time.

In addition, the presence of fluorine atoms in the MOF solids (in the very framework of the MOF solids (anion X=F), via fluoro ligands L or via the presence of fluoro molecules in the pores or at the surface of the nanoparticles of the invention) makes it possible to envision the use of these MOF solid nanoparticles for carrying oxygen for medical purposes (e.g., blood substitutes).

In the present text, the term "blood substitute" refers to a material for encapsulating oxygen, carrying it and releasing it in tissues and organs that need to be oxygenated (for example during a surgical intervention, or during hemorrhaging).

Ready-to-use, sterile, injectable, stable submicron fluorocarbon (FC) emulsions currently exist, which can deliver oxygen to tissues and, for example, reduce the recourse to blood transfusion in surgery.

Nature formulates oxygen as a water-soluble Fe complex, hemoglobin, which is itself encapsulated in the red blood cell.

The advantages of blood substitutes over transfusion include:
  avoiding contamination,
  being usable for any type of blood group,
  being accepted by all patients (even Jehovah's Witnesses),
  being easily transportable and storable and thus very useful in the event of an emergency.

Blood substitutes based on fluorocarbons, which are biologically very inert materials, are capable of dissolving large amounts of gas to deliver oxygen to tissues. Since fluorocarbons are insoluble in water, they are administered in the form of an emulsion which a) must be stable, and 2) must be rapidly excretable.

Oxygent® is one of the emulsions developed to date in this field. It is a composition comprising 60% by weight per volume of perfluorooctyl bromide ($C_8F_{17}Br$), stabilized against molecular diffusion with a few % of $C_{10}F_{21}Br$, emulsified with phospholipid droplets about 200 nm in diameter. This product has side effects in patients, and has moreover been refused marketing authorization by the FDA in February 2005 on account of safety problems.

Thus, according to the invention, the ligand L of the unit of formula (I) of the MOF solids of the present invention may be a di-, tri-, tetra- or hexacarboxylate ligand chosen from the group comprising:

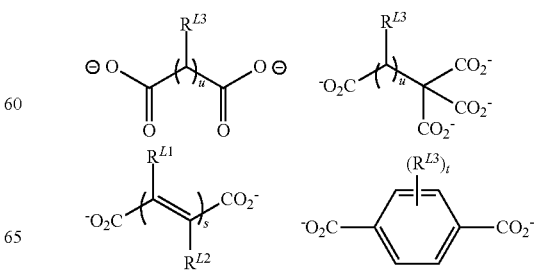

-continued

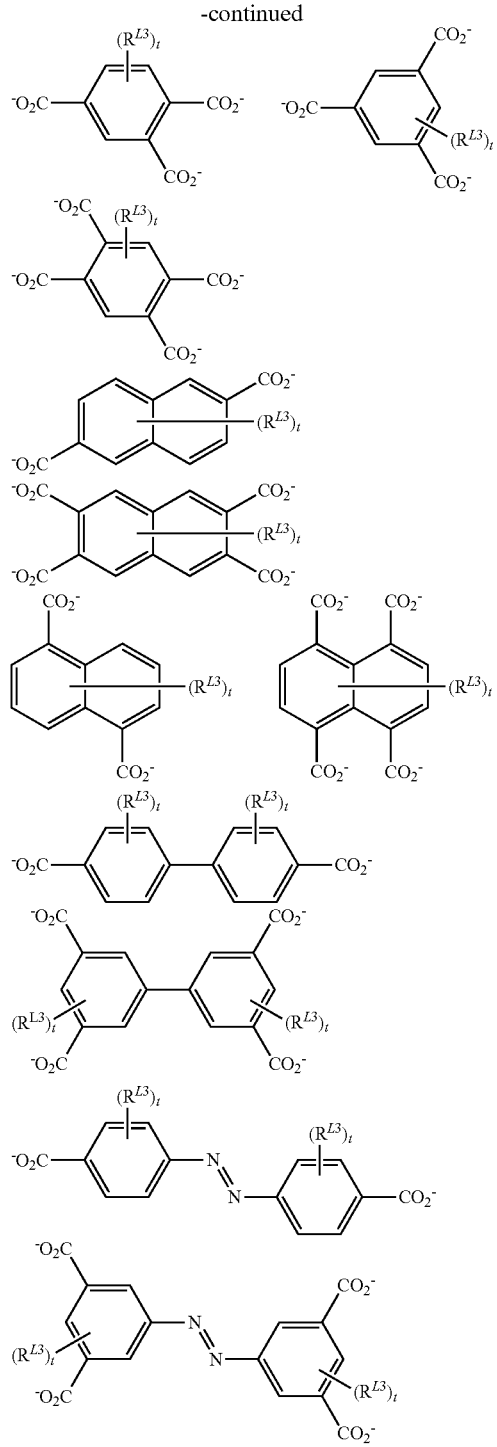

in which:

s represents an integer from 1 to 4, each occurrence of t independently represents an integer from 1 to 4, u represents an integer from 1 to 7, $R^{L1}$ and $R^{L2}$ independently represent H, a halogen or a $C_1$ to $C_6$ alkyl (preferably methyl or ethyl) and at least one occurrence of $R^{L1}$ or $R^{L2}$ represents F, and each occurrence of $R^{L3}$ independently represents H, a halogen (preferably F, Cl or Br), OH, $NH_2$, $NO_2$ or a $C_1$ to $C_6$ alkyl (preferably methyl or ethyl), and at least one occurrence of $R^{L3}$ represents F.

Preferably, each occurrence of $R^{L1}$ and $R^{L2}$ represents F.

Preferably, each occurrence of $R^{L3}$ represents F.

For example, L may represent HOOC—$C_8F_{16}$—COOH.

As generally described hereinbelow, the surface of these MOFs may be modified with a surface agent such as polyethylene glycol (PEG) so as to give them furtivity.

The surface of the nanoparticles may also be stabilized with fluoro amphiphiles so as to control the release of oxygen (delayed diffusion of oxygen from the pores of the nanoparticles). The reader may refer to the section dealing with the modification of the surfaces of the nanoparticles of the present invention, and adapt the abovementioned teaching to the grafting of fluoro amphiphilic ligands.

Thus, a process for the in vivo release of oxygen is provided, comprising administering MOF solid nanoparticles according to the invention to an individual, said nanoparticle comprising in its pores or at the surface at least one fluorocarbon or a fluoro molecule such as those mentioned previously, and encapsulated oxygen.

In particular, the MOF nanoparticle according to the invention may comprise a percentage of iron in the dry phase of from 5% to 40% and preferably from 18% to 31%.

The mass percentage (m %) is a unit of measurement used in chemistry and metallurgy for denoting the composition of a mixture or an alloy, i.e. the proportions of each component in the mixture.

1 m % of a component=1 g of the component per 100 g of mixture, or 1 kg of said component per 100 kg of mixture.

The MOF solids of the present invention especially have the advantage of being heat-stable up to a temperature of 350° C.

In particular, the MOF nanoparticles of the present invention especially have the advantage of having heat stability from 120° C. to 350° C.

In particular, the MOF nanoparticle according to the invention may have a particle diameter of less than 1000 nanometers, preferably less than 500 nm, more preferably less than 250 nm and most particularly less than 100 nm.

In particular, the MOF nanoparticle according to the invention may have a pore size of from 0.4 to 6 nm, preferably from 0.5 to 5.2 nm and more preferably from 0.5 to 3.4 nm.

In particular, the MOF nanoparticle according to the invention may have a specific surface area (BET) of from 5 to 6000 $m^2/g$ and preferably from 5 to 4500 $m^2/g$.

In particular, the MOF nanoparticle according to the invention may have a pore volume of from 0.05 to 4 $cm^2/g$ and preferably from 0.05 to 2 $cm^2/g$.

In the context of the invention, the pore volume refers to the volume accessible to the gas and/or liquid molecules.

The inventors have demonstrated that MOF materials comprising a three-dimensional structure of units of formula (I) may be in the form of a rigid or flexible structure.

The MOF nanoparticle of the present invention may be in the form of a robust structure, which has a rigid framework and contracts very little when the pores empty, or in the form of a flexible structure, which may swell and shrink, causing the aperture of the pores to vary as a function of the nature of the adsorbed molecules.

These adsorbed molecules may be, for example, solvents and/or gases.

For the purposes of the present invention, the term "rigid structure" refers to structures that swell or contract very sparingly, i.e. with an amplitude of up to 10%.

Thus, an MOF material of rigid structure may swell or contract with an amplitude of from 0 to 10%.

In particular, the MOF nanoparticle according to the invention may have a rigid structure that swells or contracts with an amplitude of from 0 to 10%.

The rigid structures may be constructed, for example, on the basis of octahedral trimers or chains.

For example, the MOF nanoparticle of rigid structure according to the invention may have a percentage of iron in the dry phase of from 5% to 40%, for example from 18% to 31%.

For example, the MOF nanoparticle of rigid structure according to the invention may have a pore size from 0.4 to 6 nm, for example from 0.5 to 5.2 nm, for example from 0.5 to 3.4 nm.

For example, the MOF nanoparticle of rigid structure according to the invention may have a pore volume from 0 to 4 $cm^3/g$, for example from 0.05 to 2 $cm^3/g$.

For the purposes of the present invention, the term "flexible structure" refers to structures that swell or contract with large amplitude, especially with an amplitude of greater than 10%, for example greater than 50%.

In particular, an MOF material of flexible structure may swell or contract with an amplitude from 10% to 300% and preferably from 50% to 300%.

The flexible structures may be constructed, for example, on the basis of octahedral trimers or chains.

In particular, the MOF nanoparticle according to the invention may have a flexible structure that swells or contracts with an amplitude of greater than 10%, for example from 50% to 300%.

For example, the MOF nanoparticle of flexible structure according to the invention may have a percentage of iron in the dry phase from 5% to 40%, for example from 18% to 31%.

For example, the nanoparticle of flexible structure according to the invention may have a pore size from 0.4 to 6 nm, for example from 0.5 to 5.2 nm, for example from 0.5 to 1.6 nm.

For example, the nanoparticle of flexible structure according to the invention may have a pore volume from 0 to 3 $cm^3/g$, for example from 0 to 2 $cm^3/g$. The pore volume represents the equivalent accessible volume (open forms) for the solvent molecules.

The present invention may be implemented with MOF materials of rigid or flexible structure.

In addition, the inventors have demonstrated experimentally that the amplitude of the flexibility depends on the nature of the ligand and of the solvent used, as described in the "Examples" section hereinbelow (especially in Example 10).

Various MOF materials were developed by the inventors at the Institut Lavoisier, Versailles with varied phases, known as "MIL" (for "Matériau Institut Lavoisier"). The name "MIL" for these structures is followed by an arbitrary number n given by the inventors to identify the various phases.

The inventors also demonstrated that iron(III) carboxylates may have a higher number of possible phases relative to the MOF materials conventionally encountered in the literature. Various phases were obtained for the iron(III) carboxylates according to the invention, for example MIL-47, MIL-53, MIL-69, MIL-88A, MIL-88B, MIL-88Bt, MIL-88C, MIL-88D, MIL-89, MIL-100, MIL-101, MIL-102. These phases are presented in the "Examples" section.

The crystallographic characteristics of these structures are known, and have been the subject of numerous reports.

Moreover, the abovementioned names "MIL" are well known to those skilled in the art.

Mention will be made, for example, of:

MIL-53: Whitfield, T. R.; Wang, X.; Liu, L.; Jacobson, A. J. *Solid State Sci.* 2005, 7, 1096.

MIL-69: T. Loiseau et al., *C. R. Chimie,* 8 765 (2005).

MIL-88A: (a) Serre et al., "Role of solvent-host interactions that lead to very large swelling of hybrid frameworks", Science, 2007, Vol. 315, 1828-1831; (b) Surblé et al., "A new isoreticular class of metal-organic frameworks with the MIL-88 topology", Chem. Comm., 2006, 284-286; (c) Mellot-Draznieks et al., "Very large swelling in hybrid frameworks: a combined computational and power diffraction study", J. Am. Chem. Soc., 2005, Vol. 127, 16273-16278. The structure of a hydrated MIL-88A solid is represented in FIG. 40.

MIL-88B, MIL-88C and MIL-88D: For these structural types, the reader may refer to the publications concerning the MIL-88A type above, namely (a) Serre et al., "Role of solvent-host interactions that lead to very large swelling of hybrid frameworks", Science, 2007, Vol. 315, 1828-1831; (b) Surblé et al., "A new isoreticular class of metal-organic frameworks with the MIL-88 topology", Chem. Comm., 2006, 284-286.

MIL-89: C. Serre, F. Millange, S. Surblé, G. Férey *Angew. Chem. Int. Ed.* 2004, 43, 6286: A new route to the synthesis of trivalent transition metals porous carboxylates with trimeric SBU. The structure of an MIL-89 solid is represented in FIG. 41.

MIL-100: Horcajada et al., "Synthesis and catalytic properties of MIL-100(Fe), an iron(III) carboxylate with large pores", Chem. Comm., 2007, 2820-2822. The structure of an MIL-100 solid is represented in FIGS. 35 and 36.

MIL-101: Férey et al., "A chromium terephthalate-based solid with unusually large pore volumes and surface area", Science, 2005, Vol. 309, 2040-2042. The structure of an MIL-101 solid is represented in FIG. 37.

MIL-102: S. Surblé, F. Millange, C. Serre, T. Düren, M. Latroche, S. Bourrelly, P. L. Llewellyn and G. Férey "MIL-102: A Chromium Carboxylate Metal Organic Framework with Gas Sorption Analysis" *J. Am. Chem. Soc.* 128 (2006), 46, 14890. The structure of an MIL-102 solid is represented in FIG. 38.

MIL-88B_4CH3, MIL-88B_CH3, MIL-88B_2CF3, MIL-88B_2OH, MIL-88B_NO2, MIL-88B_NH2, MIL-88B_Cl, MIL-88B_Br, MIL-88B_4F: For this structural type, the reader may refer to the publications concerning the above MIL-88 type, namely (a) Serre et al., "Role of solvent-host interactions that lead to very large swelling of hybrid frameworks", Science, 2007, Vol. 315, 1828-1831; (b) Surblé et al., "A new isoreticular class of metal-organic frameworks with the MIL-88 topology", Chem. Comm., 2006, 284-286; (c) Mellot-Draznieks et al., "Very large swelling in hybrid frameworks: a combined computational and power diffraction study", J. Am. Chem. Soc., 2005, Vol. 127, 16273-16278. The structure of an MIL-88B_$4CH_3$ solid is represented in FIG. 39.

In particular, the MOF nanoparticle according to the invention may have a unit of formula chosen from the group comprising:

Fe(OH)[$C_6H_4(CO_2)_2$] of flexible structure, for example MIL-53

$Fe_3OX[C_2H_2(CO_2)_2]_3$ of flexible structure, for example MIL-88A $Fe_3OX[C_4H_4(CO_2)_2]_3$ of flexible structure, for example MIL-89

$Fe_3OX[C_6H_4(CO_2)_2]_3$ of flexible structure, for example MIL-88B $Fe_3OX[O_2C—C_6(CH_3)_4—CO_2]_3.nH_2O$ of flexible structure, for example MIL-88Bt $Fe_3OX[C_6H_4(CO_2)_2]_3$ of rigid structure, for example MIL-101

$Fe_3OX[C_6H_3(CO_2)_3]_3$ of rigid structure, for example MIL-100

$Fe_3OX[C_{10}H_6(CO_2)_2]_3$ of flexible structure, for example MIL-88C $Fe_3OX[C_{12}H_8(CO_2)_2]_3$ of flexible structure, for example MIL-88D.

Most particularly, the MOF nanoparticle according to the invention may have a unit of formula chosen from the group comprising:

MIL-101 (Fe) or $Fe_3O[C_6H_4—(CO_2)_2]_3.X.nH_2O$ (X=F, Cl, OH) of rigid structure MIL-101-Cl (Fe) or $Fe_3O[Cl—C_6H_3—(CO_2)_2]_3.X.nH_2O$ (X=F, Cl, OH) of rigid structure MIL-101-$NH_2$ (Fe) or $Fe_3O[NH_2—C_6H_3—(CO_2)_2]_3.X.nH_2O$ (X=F, Cl, OH) of rigid structure MIL-101-$2CF_3$ (Fe) or $Fe_3O[(CF_3)_2—C_6H_2—(CO_2)_2]_3.X.nH_2O$ (X=F, Cl, OH) of rigid structure MIL-88B-$NO_2$ (Fe) or $Fe_3O[C_6H_3NO_2—(CO_2)_2]_3.X.nH_2O$ (X=F, Cl, OH) of flexible structure MIL-88B-2OH (Fe) or $Fe_3O[C_6H_2(OH)_2—(CO_2)_2]_3.X.nH_2O$ (X=F, Cl, OH) of flexible structure MIL-88B-$NH_2$ (Fe) or $Fe_3O[C_6H_3NH_2—(CO_2)_2]_3.X.nH_2O$ (X=F, Cl, OH) of flexible structure MIL-88B-$CH_3$ (Fe) or $Fe_3O[C_6H_3CH_3—(CO_2)_2]_3.X.nH_2O$ (X=F, Cl, OH) of flexible structure MIL-88B-Cl (Fe) or $Fe_3O[C_6H_3Cl—(CO_2)_2]_3.X.nH_2O$ (X=F, Cl, OH) of flexible structure MIL-88B-$4CH_3$ (Fe) or $Fe_3O[C_6(CH_3)_4—(CO_2)_2]_3.X.nH_2O$ (X=F, Cl, OH) of flexible structure MIL-88B-4F (Fe) or $Fe_3O[C_6F_4—(CO_2)_2]_3.X.nH_2O$ (X=F, Cl, OH) of flexible structure MIL-88B-Br (Fe) or $Fe_3O[C_6H_3Br—(CO_2)_2]_3.X.nH_2O$ (X=F, Cl, OH) of flexible structure MIL-88B-$2CF_3$ (Fe) or $Fe_3O[(CF_3)_2—C_6H_2—(CO_2)_2]_3.X.nH_2O$ (X=F, Cl, OH) of flexible structure MIL-88D $4CH_3$ (Fe) or $Fe_3O[C_{12}H_4(CH_3)_4—(CO_2)_2]_3.X.nH_2O$ (X=F, Cl, OH) of flexible structure MIL-88D $2CH_3$ (Fe) or $Fe_3O[C_{12}H_6(CH_3)_2—(CO_2)_2]_3.X.nH_2O$ (X=F, Cl, OH) of flexible structure MIL-88E (Pyr) (Fe) or $Fe_3O[C_4H_3N_2—(CO_2)_2]_3.X.nH_2O$ (X=F, Cl, OH) of flexible structure MIL-88F (Thio) (Fe) or $Fe_3O[C_4H_2S—(CO_2)_2]_3.X.nH_2O$ (X=F, Cl, OH) of flexible structure MIL-53-2OH (Fe) or FeO(OH) $[C_6H_2 (OH)_2—(CO_2)_2].X.nH_2O$ (X=F, Cl, OH) of flexible structure MIL-53-$NH_2$ (Fe) or FeO(OH) $[C_6H_2—NH_2—(CO_2)_2].X.nH_2O$ (X=F, Cl, OH) of, flexible structure MIL-53-Cl (Fe) or FeO(OH) $[C_6H_2—Cl—(CO_2)_2].X.nH_2O$ (X=F, Cl, OH) of flexible structure MIL-53-Br (Fe) or FeO(OH) $[C_6H_2—Br—(CO_2)_2].X.nH_2O$ (X=F, Cl, OH) of flexible structure MIL-53-$2CF_3$ (Fe) or FeO(OH) $[C_6H_2(CF_3)_2—(CO_2)_2].X.nH_2O$ (X=F, Cl, OH) of flexible structure MIL-53-$CH_3$ (Fe) or FeO(OH) $[C_6H_3CH_3—(CO_2)_2].X.nH_2O$ (X=F, Cl, OH) of flexible structure MIL-53-2COOH (Fe) or FeO(OH) $[C_6H_3—(CO_2)_4].X.nH_2O$ (X=F, Cl, OH) of flexible structure MIL-88G (AzBz) (Fe) or $Fe_3O[C_{12}H_8N_2—(CO_2)_2]_3.X.nH_2O$ (X=F, Cl, OH) of flexible structure MIL-88G 2Cl (AzBz-2Cl) (Fe) or $Fe_3O[C_{12}H_6N_2Cl_2—(CO_2)_2]_3.X.nH_2O$ (X=F, Cl, OH) of flexible structure.

In addition, from the same carboxylic acid ligand L and the same iron bases (chains or trimers), the inventors were able to obtain MOF materials of the same general formula (I) but of different structures. This is the case, for example, for the solids MIL-88B and MIL-101. Specifically, the difference between the solids MIL-88B and MIL-101 lies in the mode of connection of the ligands to the octahedral trimers: in the solid MIL-101, the ligands L assemble in the form of rigid tetrahedra, whereas in the solid MIL-88B, they form trigonal bipyramids, enabling spacing between the trimers.

These various materials are presented in the "Examples" section below. The mode of assembly of these ligands may be controlled during the synthesis, for example by adjusting the pH. For example, the solid MIL-88 is obtained in a less acidic medium than the solid MIL-101, as described in the "Examples" section hereinbelow.

In particular, the MOF nanoparticle of the present invention may have a phase chosen from the group comprising: MIL-53, MIL-88, MIL-100, MIL-101, MIL-102 described in the "Examples" section.

Moreover, the inventors have demonstrated the unexpected properties of the MOF nanoparticles according to the invention in imaging. Specifically, besides the magnetic susceptibility of iron(III), the structural characteristics of the iron carboxylate MOF materials of the present invention allow water to be coordinated around the $1^{st}$ coordination sphere and to circulate in the pores, which induces an effect on the longitudinal T1 and transverse T2 relaxation times of water. In particular, the relaxivity r2 of the nanoparticles is sufficient for in vivo use during gradient echo experiments.

For example, the nanoparticle according to the invention may have a transverse relaxivity r2 of at least 18 $mMs^{-1}$, for example at least 8.6 $mMs^{-1}$.

Thus, the invention also relates to the use of MOF nanoparticles according to the invention as contrast agents.

Moreover, research studies conducted by the inventors have enabled them to develop a flexible and modulable synthetic method for obtaining the MOF nanoparticles according to the invention having a particular isoreticular structural organization, in good yields. In addition, the process makes it possible to obtain nanoparticles of desired dimensions and uniform particle size and pore size.

Thus, the invention also relates to a process for preparing nanoparticles as defined in the present invention, comprising at least one reaction step (i) that consists in mixing in a polar solvent:

at least one solution comprising at least one metallic inorganic precursor in the form of iron metal, an iron(III) salt, an iron(II) salt or a coordination complex comprising the metal ion $Fe^{3+}$ or $Fe^{2+}$, at least one ligand L' comprising a radical R bearing q groups *—C(=O)—$R^3$, in which q for the ligands L above and R are as defined;

* denotes the point of attachment of the group to the radical R;

$R^3$ is chosen from the group comprising a radical —OH, a radical —OY in which Y represents an alkali metal cation, a halogen or a radical —$R^4$, —O—C(=O)$R^4$ or —$NR^4R^{4'}$, in which $R^4$ and $R^{4'}$ are $C_{1-12}$ alkyl radicals, so as to obtain said nanoparticles.

The radicals $R^4$ and $R^{4'}$ may be identical or different.

In one embodiment, the ligand L' may represent a di-, tri-, tetra- or hexadentate ligand chosen from the group comprising:

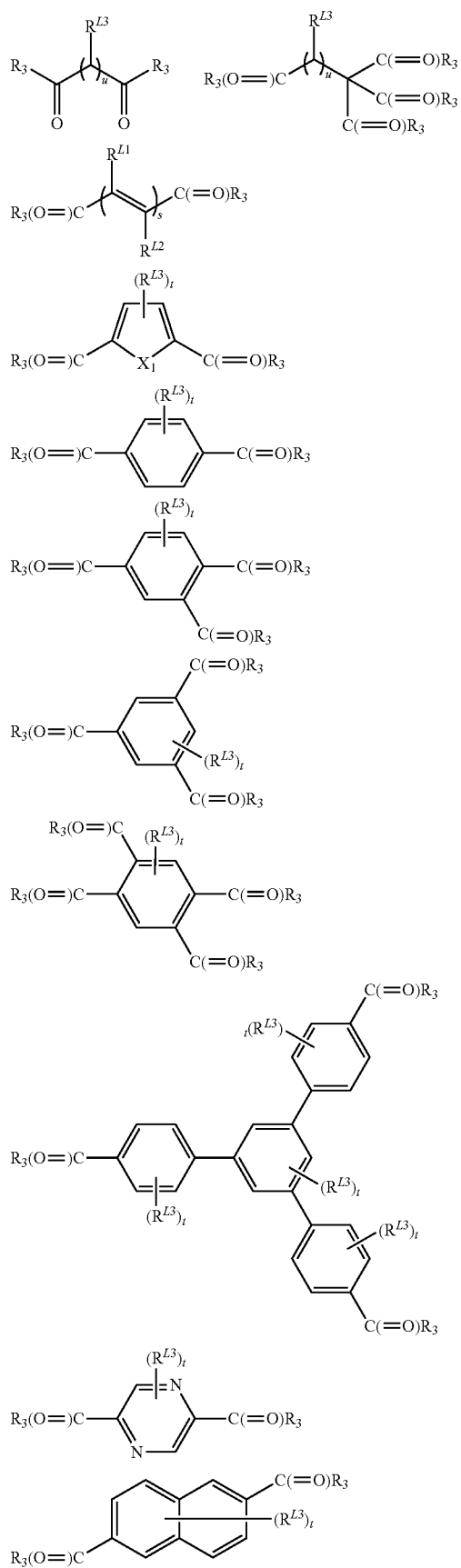
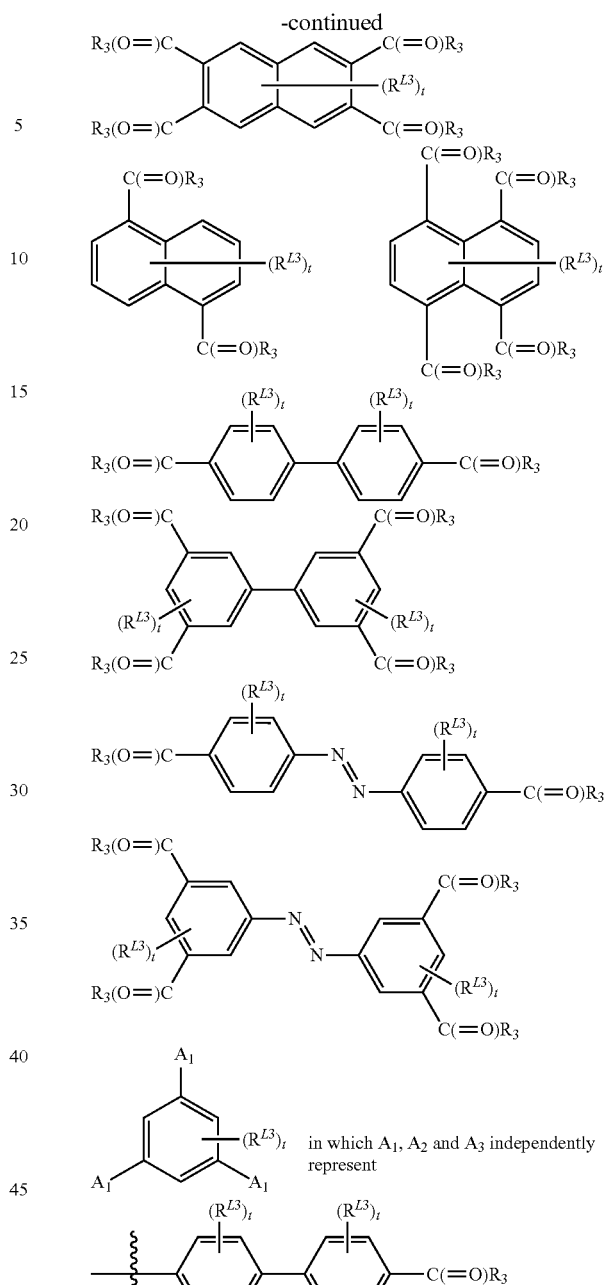

in which:
R³ is as defined above,
X₁ represents O or S,
s represents an integer from 1 to 4,
each occurrence of t independently represents an integer from 1 to 4,
u represents an integer from 1 to 7,
$R^{L1}$ and $R^{L2}$ independently represent H, a halogen or a $C_1$ to $C_6$ alkyl (preferably methyl or ethyl), and
each occurrence of $R^{L3}$ independently represents H, a halogen (preferably F, Cl or Br), OH, $NH_2$, $NO_2$ or a $C_1$ to $C_6$ alkyl (preferably methyl or ethyl).

In one embodiment, each occurrence of the radicals $R^{L1}$, $R^{L2}$ and $R^{L3}$ represents a hydrogen atom.

Preferably, in the reaction step (i), the ligand L' used may be a di-, tri- or tetracarboxylic acid chosen from the group comprising: $C_2H_2(CO_2H)_2$ (fumaric acid), $C_2H_4(CO_2H)_2$ (succinic acid), $C_3H_6(CO_2H)_2$ (glutaric acid), $C_4H_4(CO_2H)_2$ (muconic acid), $C_4H_8(CO_2H)_2$ (adipic acid), $C_7H_{14}(CO_2H)_2$ (azelaic acid), $C_5H_3S(CO_2H)_2$ (2,5-thiophenedicarboxylic acid), $C_6H_4(CO_2H)_2$ (terephthalic acid), $C_6H_2N_2$ $(CO_2H)_2$ (2,5-pyrazinedicarboxylic acid), $C_{10}H_6(CO_2H)_2$ (naphthalene-2,6-dicarboxylic acid), $C_{12}H_8(CO_2H)_2$ (biphenyl-4,4'-dicarboxylic acid), $C_{12}H_8N_2(CO_2H)_2$ (azobenzenedicarboxylic acid), $C_6H_3(CO_2H)_3$ (benzene-1,2,4-tricarboxylic acid), $C_6H_3(CO_2H)_3$ (benzene-1,3,5-tricarboxylate acid), $C_{24}H_{15}(CO_2H)_3$ (benzene-1,3,5-tribenzoic acid), $C_6H_2(CO_2H)_4$ (benzene-1,2,4,5-tetracarboxylic acid), $C_{10}H_4(CO_2H)_4$ (naphthalene-2,3,6,7-tetracarboxylic acid), $C_{10}H_4(CO_2H)_4$ (naphthalene-1,4,5,8-tetracarboxylic acid), $C_{12}H_6(CO_2H)_4$ (biphenyl-3,5,3',5'-tetracarboxylic acid), and modified analogs chosen from the group comprising 2-aminoterephthalic acid, 2-nitroterephthalic acid, 2-methylterephthalic acid, 2-chloro-terephthalic acid, 2-bromoterephthalic acid, 2,5-dihydroxoterephthalic acid, tetrafluoroterephthalic acid, tetramethylterephthalic acid, dimethyl-4,4'-biphenyldicarboxylic acid, tetramethyl-4,4'-biphenyldicarboxylic acid, dicarboxy-4,4'-biphenyldicarboxylic acid, 2,5-pyrazinedicarboxylic acid. The ligand L' used may also be chosen from the group comprising: 2,5-diperfluoroterephthalic acid, azobenzene-4,4'-dicarboxylic acid, 3,3'-dichloroazobenzene-4,4'-dicarboxylic acid, 3,3'-dihydroxoazobenzene-4,4'-dicarboxylic acid, 3,3'-diperfluoroazobenzene-4,4'-dicarboxylic acid, 3,5,3',5'-azobenzenetetracarboxylic acid, 2,5-dimethylterephthalic acid, perfluoroglutaric acid.

It will be understood that, in the implementation of the process, the ligand L' is not necessarily in the form of a carboxylic acid. As indicated previously, the latter may be present in a derived form in which one or more carboxylic functions is/are in the form $—C(=O)—R^3$ in which $R^3$ may represent a radical $—OY$ in which Y represents an alkali metal cation, a halogen or a radical $—OR^4$, $—O—C(=O)R^4$ or $—NR^4R^{4'}$, in which $R^4$ and $R^{4'}$ are independently $C_{1-12}$ alkyl radicals.

The synthesis of MOF materials may preferably be performed in the presence of energy, which may be supplied, for example, by heating, for instance under hydrothermal or solvothermal conditions, but also by microwave, by ultrasound, by grinding, by a process involving a supercritical fluid, etc. The corresponding protocols are those known to a person skilled in the art. Nonlimiting examples of protocols that may be used for hydrothermal or solvothermal conditions are described, for example, in K. Byrapsa, et al. "Handbook of hydrothermal technology", Noyes Publications, Parkridge, N.J., USA, William Andrew Publishing, LLC, Norwich N.Y. USA, 2001 [9]. For the synthesis via microwaves, nonlimiting examples of protocols that may be used are described, for example, in G. Tompsett, et al. *Chem Phys Chem*. 2006, 7, 296 [10]; in S.-E. Park, et al. *Catal. Survey Asia* 2004, 8, 91 [11]; in C. S. Cundy, *Collect. Czech. Chem. Commun*. 1998, 63, 1699 [12]; or in S. H. Jhung, et al. *Bull. Kor. Chem. Soc*. 2005, 26, 880 [13]. For the conditions in the presence of a roll mill, reference may be made, for example, to the publications A. Pichon et al., *Cryst. Eng. Comm*. 8, 2006, 211-214 [14]; D. Braga et al., *Angew. Chem. Int. Ed*. 45, 2006, 142-246 [15]; D. Braga et al., *Dalton Trans*. 2006, 1249-1263 [16].

The hydrothermal or solvothermal conditions, the reaction temperatures of which may range between 0 and 220° C., are generally performed in glass (or plastic) containers when the temperature is below the boiling point of the solvent. When the temperature is higher or when the reaction is performed in the presence of fluorine, Teflon bodies inserted into metal bombs are used [9].

The solvents used are generally polar. The following solvents may especially be used: water, alcohols, dimethylformamide, dimethyl sulfoxide, acetonitrile, tetrahydrofuran, diethylformamide, chloroform, cyclohexane, acetone, cyanobenzene, dichloromethane, nitrobenzene, ethylene glycol, dimethylacetamide, or mixtures of these solvents.

One or more cosolvents may also be added at any step in the synthesis for better dissolution of the compounds of the mixture. They may especially be monocarboxylic acids, such as acetic acid, formic acid, benzoic acid, etc.

When the cosolvent is a monocarboxylic acid, this acid, besides having a solubilizing effect, also makes it possible to stop the crystal growth of the MOF solid. Specifically, the carboxylic function coordinates with iron, which can no longer bind to another iron atom because of the presence of a second —COOH function on the cosolvent molecule. Thus, the growth of the crystal network is slowed down, and then stopped. The addition of a monocarboxylic cosolvent, such as acetic acid, formic acid, benzoic acid, etc., thus makes it possible to reduce the size of the MOF solid particles obtained. The use of a monocarboxylic cosolvent can thus promote the production of nanoparticles (particle size<1 μm).

In general, control of the size of the nanoparticles may be performed by adding a monocarboxylic molecule. This molecule may be one of the abovementioned cosolvents. It may also be a monocarboxylic organic surface agent. The notion of organic surface agents, and their use in the context of the present invention, are described in detail hereinbelow. For example, a monocarboxylic organic surface agent, such as PEG-COOH, may be added in the course of the synthesis. This has the two fold function of:

stopping the crystal growth of the MOF network (and thus enabling the production of smaller nanoparticles)

modifying the surface of the nanoparticles by grafting PEG groups (organic surface agent function).

One or more additives may also be added during the synthesis so as to modify the pH of the mixture. These additives are chosen from mineral or organic acids or mineral or organic bases. In particular, the additive may be chosen from the group comprising: HF, HCl, $HNO_3$, $H_2SO_4$, NaOH, KOH, lutidine, ethylamine, methylamine, ammonia, urea, EDTA, tripropylamine, pyridine, etc.

Preferably, reaction step (i) may be performed according to at least one of the following reaction conditions:

with a reaction temperature from 0° C. to 220° C., preferably from 50 to 150° C.;

with a stirring speed from 0 to 1000 rpm (or revolutions per minute), preferably from 0 to 500 rpm;

with a reaction time from 1 minute to 96 hours, preferably from 1 minute to 15 hours;

with a pH from 0 to 7, preferably from 1 to 5;

with the addition of at least one cosolvent to the solvent, to the precursor, to the ligand or to the mixture thereof, said cosolvent being chosen from the group comprising acetic acid, formic acid and benzoic acid;

in the presence of a solvent chosen from the group comprising water, alcohols $R^S—OH$ in which $R^S$ is a linear or branched $C_1$ to $C_6$ alkyl radical, dimethylformamide, dimethyl sulfoxide, acetonitrile, tetrahydrofuran, diethylformamide, chloroform, cyclohexane, acetone, cyanobenzene, dichloromethane, nitrobenzene, ethylene glycol, dimethylacetamide, or mixtures of these solvents, which may be miscible or immiscible;

in a supercritical medium, for example in supercritical $CO_2$;
under microwaves and/or under ultrasound;
under electrochemical electrolysis conditions;
under conditions using a roll mill;
in a gas stream.

The synthesis of MOF materials may preferably be performed under experimental conditions that favor the formation of nanoparticles. For example, control of the following parameters may be important for producing MOF solid nanoparticles according to the invention:
reaction temperature,
reaction time,
concentrations of ligand L' and of metallic inorganic precursor, and/or
addition of one or more additives such as pH modifiers (acids, bases), mineralizers, or agents for promoting stoppage of the crystal growth (monocarboxylic acid).

The preferred ranges of values for each of these parameters may vary depending on whether the synthesis of the nanoparticles is performed via the hydro/solvothermal route, via ultrasound or via microwave. For example, a higher reaction temperature will generally be used for the hydro/solvothermal route (about 20-150° C.) than for the ultrasonication route (about 0° C.).

As described in Example 6B, the inventors have demonstrated that the four abovementioned parameters not only have an impact on the production of nanoparticles (i.e. particles smaller than 1 μm in diameter) but also on obtaining good crystallization, a satisfactory yield (e.g. >25% by weight) and the absence of iron oxides.

Optimum conditions were determined empirically by the inventors for each of the prepared MOF solid phases. For illustrative and nonlimiting purposes, examples of operating conditions are detailed in the "Examples" section. It is understood that the operating conditions detailed in the "Examples" are not in any way limiting, since the nanoparticles according to the invention can be obtained in temperature, reaction time and concentration ranges, and with amounts of additives, varying about the operating conditions illustrated in the examples, according to the desired size of the nanoparticles and desired polydispersity.

In general, according to the process for preparing the MOF solid nanoparticles of the invention, the MIL-88A phase is obtained in the form of nanoparticles by using the following parameters:

Solvothermal Route
the reaction temperature is preferably between 20 and 200° C., more particularly between 50 and 100° C. and most particularly between 60 and 70° C.,
the reaction time is between 30 minutes and 72 hours, more particularly between 30 minutes and 12 hours and most particularly between 1 and 4 hours,
the concentration of ligand L' and of metallic inorganic precursor is between 1 and 200 mmol/L, more particularly between 30 and 100 mmol/L and most particularly between 60 and 70 mmol/L,
a monocarboxylic acid is added, preferably acetic acid. It is understood that other additives such as pH modifiers (acids, bases) or mineralizers may also be added.

Ultrasonication Route
the reaction temperature is preferably between −5° C. and 20° C., more particularly between −5° C. and 10° C. and most particularly between −5° C. and 5° C.,
the reaction time is between 15 minutes and 2 hours, more particularly between 15 minutes and 1 hour and most particularly between 15 and 45 minutes,
the concentration of ligand L' and of metallic inorganic precursor is between 10 mol/l and $10^{-2}$ mol/l, more particularly between 1 and $10^{-2}$ mol/l and most particularly between 50 and 200 mol/l,
a monocarboxylic acid is added, preferably acetic acid. It is understood that other additives such as pH modifiers (acids or bases) or mineralizers may also be added.

Microwave Route
the reaction temperature is preferably between 30° C. and 300° C., more particularly between 30° C. and 150° C. and most particularly between 50° C. and 120° C.,
the reaction time is between 1 minute and 3 hours, more particularly between 10 and 50 minutes and most particularly between 1 and 30 minutes,
the concentration of ligand L' and of metallic inorganic precursor is between 200 mol/l and $10^{-2}$ mol/l, more particularly between 100 and $10^{-2}$ mol/l and most particularly between 10 and $10^{-2}$ mol/l,
a pH modifier is added, preferably hydrochloric acid. It is understood that other additives such as pH modifiers (acids or bases), mineralizers or agents for promoting the stoppage of crystal growth (monocarboxylic acid) may also be added.

The other "MIL" phases may be obtained in the form of nanoparticles under similar operating conditions, by using the abovementioned temperature, reaction time and concentration ranges, and with the optional addition of additives such as those mentioned previously.

The preparation process of the invention has the advantage of allowing the production of the desired materials in the form of pure and homogeneous nanoparticles, in a limited number of steps and with high yields. This reduces the synthesis time and the manufacturing costs.

In addition, the iron(III) carboxylates nanoparticles require synthetic conditions that are less harsh than with other metals, for instance chromium(III).

In addition, this process allows access to materials of given structure and allows the particle size to be controlled by modifying one or more of the following parameters: the synthesis time, the pH, the addition of additives, stirring, the nature of the solvent, the use of the microwave route, etc.

Moreover, the inventors have also demonstrated that the particular structural characteristics of the nanoparticles of the present invention, especially in terms of flexibility or pore size, make them adsorbents with a high loading capacity, a high selectivity and high purity. They thus enable the selective adsorption of molecules, for instance pharmaceutical molecules, with a favorable energy cost and a longer release time.

Thus, the research studies conducted by the inventors have enabled them to demonstrate the advantage of MOF materials for adsorbing and carrying active principles.

Thus, the invention also relates to the use of MOF nanoparticles according to the invention, said nanoparticles comprising in their pores or at their surface at least one molecule chosen from the group comprising a pharmaceutically active principle, a compound of cosmetic interest or a marker.

In particular, the invention also relates to the use of MOF nanoparticles according to the invention loaded with pharmaceutically active principle as a medicament. The pharmaceutically active principle may be contained either in the pores or at the surface of the nanoparticle according to the invention. This is what is understood in the rest of this document by the expression "nanoparticle loaded with pharmaceutically active principle".

More generally, the term "nanoparticle loaded with component X" refers to a nanoparticle according to the invention containing in its pores or at its surface the component X. The component X may be adsorbed or bound by covalent bonding, by hydrogen bonding, by Van der Waals bonding, by electrostatic interaction at the surface or in the pores of the nanoparticle. This component X may be, as indicated above, a pharmaceutically active principle. Alternatively, component X may be any molecule with biological activity, a compound of cosmetic interest or a marker.

Specifically, the MOF nanoparticles according to the invention have the advantage of having large adsorption capacities. In addition, they can efficiently adsorb pharmaceutical molecules that have particular encapsulation difficulties, for example on account of their instability, their high reactivity, their poor solubility, their strong tendency to crystallize, their hydrophilic or amphiphilic nature, etc.

For example, the nanoparticle according to the invention may be loaded with at least one pharmaceutically active principle that has one or more of the following characteristics: hydrophilic, amphiphilic, lipophilic, unstable, toxic, strong tendency to crystallize or substantially insoluble.

The term "toxic" refers to a pharmaceutically active principle that has toxic effects liable to hinder its use in medical or veterinary applications. They may be, for example, alkylating agents such as busulfan, cisplatin or nitrosoureas such as lomustine. After metabolization, alkylating agents form covalent bonds with nucleic acids. The formation of these bonds may result in:

DNA transcription and replication disorders,
base substitutions in DNA,
base excisions and DNA chain splitting.

Their main pharmacological activity is manifested during the synthesis phase of DNA. Their toxic effects include: myelosuppression, sterility and non-lymphocytic leukemia.

Cisplatin causes intra-catenary DNA bridging, has low myelotoxicity, but is a powerful emetic and may be nephrotoxic.

The term "strong tendency to crystallize" refers to a pharmaceutically active principle that has a tendency to self-associate in a crystal lattice instead of being included in other structures. Thus, such a compound tends to form crystals during the encapsulation process used, rather than being included in particles. This thus gives at the end of the process a mixture of particles that are poorly loaded with pharmaceutically active principles and crystals thereof. It may be, for example, busulfan. At high dose, it has a serious side effect, namely veno-occlusive liver disease. This probably results from the very strong tendency of this molecule to crystallize. The crystal stacking is governed by strong dipole-dipole interactions between the methylsulfonate groups of this active principle.

The term "substantially insoluble" refers to a pharmaceutically active principle whose solubility is less than 0.1 mg/ml in water. It may be, for example, busulfan.

The term "unstable" refers to a pharmaceutically active principle that can decompose, crystallize and/or react and in so doing lose its structure and its activity. A possible example of this is busulfan.

In addition, the pharmaceutically active principle may be any molecule that has biological activity, for instance a medicament, especially an anticancer agent, an antiviral agent, a modified or unmodified nucleoside analog, a nucleic acid, an antibody, a protein, a vitamin, etc.

Among the hydrophilic active principles that may be mentioned, for example, are AZT, TP, CDV (cidofovir), 5-fluorouracil and citarabine.

Among the amphiphilic active principles that may be mentioned, for example, are busulfan, doxorubicin chloride and imipramine chloride.

Among the lipophilic active principles that may be mentioned, for example, are tamoxifen, docetaxel, paclitaxel, ibuprofen, lidocaine, liposoluble vitamins such as vitamins A (retinol), D (calciferol), E (tocopherol), K1 (phylloquinone) and K2 (menaquinone).

In particular, the nanoparticle according to the invention may be loaded with at least one pharmaceutically active principle chosen, for example, from the group comprising taxotere, busulfan, azidothymidine (AZT), azidothymidine phosphate (AZTP), cidofovir, gemcitabine and tamoxifen.

In one embodiment, the active principle may be a fluorescent molecule. For example, it may be rhodamines, fluorescein, luciferase, pyrene and derivatives thereof, or aminopyrrolidino-7-nitrobenzofurazan.

In one embodiment, the active principle may be a fluoro molecule, i.e. a molecule comprising at least one substituent F. It may be, for example, one of the fluoro molecules mentioned previously. These fluoro molecules are suitable for use in imaging, particularly fluorescence imaging such as the abovementioned PET technique.

Thus, the invention also relates to the use of MOF nanoparticles encapsulating one or more fluoro molecules according to the invention, as marker that may be used in medical imaging, such as PET imaging.

In addition, the nanoparticle according to the invention may be loaded with at least one compound of cosmetic interest.

The term "compound of cosmetic interest" refers to any active substance included in the formulation of a cosmetic preparation, i.e. a preparation intended to be placed in contact with various surface parts of the human body, especially the epidermis, the pilous and hair systems, the external organs, the teeth and mucous membranes, for the purpose, exclusively or mainly, of cleaning, protecting or fragrancing them, maintaining the human body in good condition, modifying its appearance or correcting its odor. The term "active substance" refers to a substance that ensures the efficacy of the cosmetic preparation.

The compound of cosmetic interest may be an active substance included in the preparation of any cosmetic preparation known to those skilled in the art, for example hygiene products (e.g. makeup remover, toothpaste, deodorant, shower gel, soap or shampoo), care products (e.g. anti-wrinkle cream, day cream, night cream, moisturizing cream, floral water, scrub, milk, beauty mask, lip balm or tonic), haircare products (e.g. hair conditioner, relaxer, gel, oil, lacquer, mask or dye), makeup products (e.g. concealer, self-tanning product, eyeliner, makeup powder, foundation, kohl, mascara, powder, skin bleaching product, lipstick or nail varnish), fragrances (e.g. eau de Cologne, eau de toilette or fragrance), antisun products (e.g. after-sun and antisun creams, oils and lotions), shaving products and hair-removing products (e.g. aftershave, hair-removing cream or shaving foam) or bath and shower preparations (e.g. bubble bath, bath oil or bath salts).

According to the invention, the compound of cosmetic interest may be chosen, for example, from the group comprising:

an antioxidant (for example citric acid, beta-carotene, vitamin E, glycolic acid, glutathione, vitamin C, polyphenols, lycopene, flavonoids, tannins, anthocyans, N-acetylcysteine (free-radical scavenger))

a vitamin (for example vitamin A, B3, B5, B6, B2, B1, B9, B8, B12, C, E, D, K, K1, K2)

a liporegulator (for example caffeine or theophylline)

a photoprotective agent (for example benzophenone-3 (2-hydroxy-4-methoxybenzophenone), benzophenone-4 (2-hydroxy-4-methoxybenzophenone-5-sulfonic acid), 2-phenylbenzimidazole-5-sulfonic acid)

a moisturizer (for example urea, hyaluronic acid or sorbitol).

For example, the nanoparticle according to the invention may be loaded with at least one compound of cosmetic interest chosen from the group comprising benzophenone, visnadine, salicylic acid, ascorbic acid, benzophenone and derivatives thereof, caffeine, urea, hyaluronic acid, etc.

In particular, the nanoparticle according to the invention may be loaded with pharmaceutically active principle with a loading capacity from 1% to 200% by weight of dry solid, for example from 1% to 70% by weight of dry solid, i.e. close to 10 to 700 mg per gram of dry solid.

In the context of the present invention, the loading capacity refers to the capacity for storing molecules or the amount of molecules adsorbed into the material. The loading capacity may be expressed as a mass capacity (gram/gram) or as a molar capacity (mol/mol) or in other terms (mol/gram, gram/mol, etc.).

Thus, the nanoparticles according to the invention have the advantage of having unexpected loading capacities, never before achieved in the prior art, especially in the case of busulfan. Specifically, the nanoparticles of the invention have a hydrophobic/hydrophilic internal microenvironment that is favorable especially for the incorporation of amphiphilic molecules such as busulfan.

In addition, another problem of the prior art concerns the rapid and uncontrolled release of the carried molecules in the absence of affinity. The MOF nanoparticles according to the invention have the advantage of allowing longer release times, especially by virtue of the internal microenvironment, but also by virtue of the structure of the compounds. Specifically, the rigid and flexible phases of the MOF structures have an influence on the release kinetics of the molecules. In particular, the flexible phases may allow a longer release of the compounds over time, for example with ibuprofen and the compound MIL-53.

The nanoparticles according to the invention may further comprise, for example on the spacer ligands, functional groups that can modify the interactions between the MOF nanoparticle according to the invention and the molecule of interest. This may make it possible to control the encapsulation and release of the molecules of interest. The MOF materials of the invention may thus be adapted and formulated ("designed") as a function of the molecules of interest to be carried so as to modify the degree of encapsulation, the release of the molecules and/or the degradability of the solid.

Furthermore, the MOF nanoparticles according to the invention underwent very positive toxicity studies, described in the "Examples" section hereinbelow. They also appear to be biodegradable, and the degradability studies are still underway.

Thus, the MOF nanoparticles of the present invention used for carrying active principles make it possible to overcome the prior art problems mentioned previously, especially the problems associated with the toxicity, instability, strong tendency of the active principles to crystallize, their controlled release, etc.

In addition, they make it possible to graft molecules onto their surface so as to satisfy needs associated with the vectorization of compounds toward specific biological targets and/or the furtiveness of particles. This thus makes it possible to improve the biodistribution of the active principles.

Thus, according to one particular embodiment, the MOF nanoparticle according to the invention may further comprise on its surface at least one organic surface agent. This agent may be grafted or deposited on the surface of the nanoparticles, for example adsorbed onto the surface or bonded via covalent bonding, via hydrogen bonding, via Van der Waals bonding or via electrostatic interaction. The surface agent may also be incorporated by entanglement during the manufacture of the nanoparticles.

The surface agent may be, for example, a phosphate-containing surface agent incorporated after the synthesis of the nanoparticles.

According to the invention, the term "surface agent" refers to a molecule that partly or totally covers the surface of the solid, enabling the surface properties of the material to be modified, for example:

to modify its biodistribution, for example to avoid its recognition by the reticuloendothelial system ("furtiveness"), and/or to give it advantageous bioadhesion properties during oral, ocular or nasal administration, and/or to enable it to perform specific targeting of certain diseased organs/tissues, etc.

According to the invention, several surface agents may be used to combine the abovementioned properties.

According to the invention, a surface agent combining at least two of the abovementioned properties may be used.

According to the invention, the organic surface agent may be chosen, for example, from the group comprising:

an oligosaccharide, for instance cyclodextrins, a polysaccharide, for instance chitosan, dextran, fucoidan, alginates, pectin, amylose, starch, cellulose or xylan, a glycosaminoglycan, for instance hyaluronic acid or heparin, a polymer, for instance polyethylene glycol (PEG), polyvinyl alcohol or polyethyleneimine, a surfactant, for instance pluronic or lecithin, vitamins, for instance biotin, coenzymes, for instance lipoic acid, antibodies or antibody fragments, amino acids or peptides.

The surface agent may also be a targeting molecule, i.e. a molecule that recognizes or is specifically recognized by a biological target. The combination of the MOF solids of the invention with a targeting molecule thus makes it possible to direct the nanoparticles according to the invention, and thus to vectorize the active principles, toward this biological cell, tissue or organ target.

Preferably, the nanoparticle according to the invention may comprise at least one targeting molecule, as organic surface agent, which may be chosen from the group comprising: biotin, avidin, folic acid, lipoic acid, ascorbic acid, an antibody or antibody fragment, a peptide or a protein.

Thus, the organic surface agent may be a targeting molecule chosen from the group comprising biotin, chitosan, lipoic acid, an antibody or antibody fragment, and a peptide.

For example, the presence of biotin at the surface may be exploited in order easily to couple ligands, for example by simple incubation. To do this, it is possible to use protocols described in the publications S. Balthasar et al., *Biomaterials*, Volume 26, Issue 15, May 2005, 2723-2732 [17] and R. Gref et al., *Biomaterials*, Volume 24, Issue 24, November 2003, 4529-4537 [18].

Another ligand may be used instead of biotin, for example folic acid. This ligand is of certain interest in the field of cancer, as shown by the abovementioned publications [17] and [18].

This surface-modification method has the advantage of not disturbing the core of the MOF solid particles, in particular when they contain gas, and of being able to do so during or after the synthesis of the MOF solids, and thus offering a variety of possible coatings.

It is also possible to use a mixture of polymers comprising functions that are capable of interacting with the particle (MOF) as surface agent so as to satisfy precise specifications, for example bioadhesion, specific recognition, etc.

Among the surface agents that enable specific targeting of certain diseased organs/tissues, examples that may be mentioned include vitamins (biotin, folic acid, lipoic acid or ascorbic acid), antibodies or antibody fragments, peptides and proteins.

In addition, the grafting of a surface agent onto the surface of the MOF solid according to the invention makes it possible to satisfy needs associated with the vectorization of the compound toward specific biological targets and/or the furtiveness of the material. This makes it possible to modify the biodistribution of the material.

According to the invention, the surface agent may be grafted or deposited onto the surface of the solid according to the invention, for example adsorbed onto the surface or bonded via covalent bonding, via hydrogen bonding, via Van der Waals bonding or via electrostatic interaction. The surface agent may also be incorporated by entanglement during the manufacture of the solid.

The surface agent may be, for example, a phosphate-containing surface agent incorporated during or after the synthesis of the solid.

According to the invention, the organic surface agent may be chosen, for example, from the group comprising an oligosaccharide, a polysaccharide, chitosan, dextran, hyaluronic acid, heparin, fucoidan, alginate, pectin, amylose, cyclodextrins, starch, cellulose, xylan, a polymer or a copolymer, for instance polyethylene glycol (PEG), pluronic, polyvinyl alcohol, polyethylene imine, etc.

In addition, the MOF nanoparticles according to the invention make it possible to incorporate markers into these materials, which is also an advantage.

Thus, according to one particular embodiment, the nanoparticle according to the invention may be loaded with at least one molecule of interest, which may be a pharmaceutically active principle and/or a compound of cosmetic interest and/or a marker. The molecule of interest may be contained either in the pores or at the surface of the nanoparticle according to the invention.

Thus, the MOF nanoparticles according to the invention may be used for the manufacture of medicaments, cosmetic compositions and/or markers that may be used in medical imaging.

Thus, a process is provided for treating an individual suffering from a disease, said process comprising administering to said individual MOF solid nanoparticles according to the invention comprising in their pores or at their surface at least one active principle known for treating said disease.

In particular, the MOF nanoparticle according to the invention may be loaded with at least one marker chosen from the group comprising a medical imaging marker, a contrast agent, a tracer, a radioactive marker, a fluorescent marker and a phosphorescent marker.

For example, the inventors describe in the "Examples" section hereinbelow a surface modification using a fluorescent compound, in particular dextran marked with fluorescein. This modification allows the detection of particles using a confocal microscope. A confocal laser scanning microscope (CLSM) is an optical microscope that has the property of producing images of very low field depth (about 600 nm) known as "optical sections". By positioning the focal plane of the lens at different depth levels in the sample, it is possible to produce series of images from which a three-dimensional representation of the object may be obtained. A few possible applications are:

i) study of the interactions with cell lines;
ii) if the particles have relaxivities that are compatible with their observation in medical imaging, they can be used in multimodal imaging, as suggested in the publication by Mulder W. J. et al. *Nanomed.* 2007 June, 2(3), 307-324 [21].

In particular, the nanoparticle according to the invention may be loaded with at least one marker chosen from the group comprising: a fluorescent compound, an iron oxide, a gadolinium complex, gadolinium ions directly present in the structure, for example in the form of a complex with the organic ligand, etc. The protocols for loading with marker are those known to a person skilled in the art. Nonlimiting examples that may be used are described, for example, in A. K. Gupta, et al., *Nanomed.* 2007 2(1), 23-39 [22]; in P Caravan, *Chem. Soc. Rev.*, 2006, 35, 512-523 [23]; or in Yan-Ping Ren, et al., *Angew, Chem. Int. Ed.* 2003, 42, No. 5, 532 [24].

Thus, the MOF nanoparticles according to the invention may be used for manufacturing, carrying and/or vectorizing markers.

In addition, the nanoparticles of the invention may be used for vectorizing medicaments when they are loaded with pharmaceutically active principle and/or for detecting and monitoring diseases involving biological targets (such as cancer) when they are used as a marker.

In addition, by cumulating these two uses, the nanoparticles of the present invention advantageously make it possible to visualize the biodistribution of a medicament. This is of great interest, especially for monitoring a therapeutic treatment and for studying the biodistribution of a medicament.

According to one particular embodiment of the invention, the process for preparing the nanoparticles according to the invention may further comprise a step (ii) of introducing into said nanoparticle at least one molecule of interest, which may be a pharmaceutically active principle and/or a compound of cosmetic interest and/or a marker.

Said introduction step may be performed during the reaction step (i) or thereafter so as to obtain a solid loaded with the molecule of interest.

Any method known to those skilled in the art may be used during the introduction step (ii). The molecule of interest may be introduced, for example, into the MOF material of the present invention:

via impregnation, by immersing the material in a solution of the molecule of interest;
by sublimation of the molecule of interest, and the gas is then adsorbed by the material; or
via rotary roll milling, which consists in mechanically mixing the material and the molecule of interest.

According to one particular mode of the invention, the process for preparing nanoparticles according to the invention may further comprise a step (iii) of binding to said nanoparticle at least one organic surface agent.

This binding step (iii) may be performed during or after the reaction step (i) or alternatively after the step (ii) of introducing the molecule of interest. Examples are provided hereinbelow (example 22, example 23, example 24).

A certain number of surface-modified MOF solid nanoparticles are illustrated in the "Examples" section. It is understood that these examples are given as illustrations and are not limiting. The methods for modifying the surface of the MOF solid nanoparticles illustrated in the Examples are applicable and/or adaptable to all of the MOF solid nanoparticles according to the present invention (e.g. the MOF solids with different ligands L, and/or optionally encapsulating at least one active principle, a compound of cosmetic interest and/or a marker). For example, these methods may be used without difficulty for modifying the surfaces of all of the MOF solid nanoparticles described in the present patent application.

Other advantages may also emerge to those skilled in the art on reading the examples below, with reference to the attached figures, which are given as nonlimiting illustrations.

BRIEF DESCRIPTION OF THE FIGURES

FIG. 13a concerns the control test, FIG. 13b is obtained 7 days after the injection of 200 mg/kg of the material MIL-88A and FIG. 13c is obtained 7 days after the injection of 200 mg/kg of the material MIL-88Bt.

EXAMPLES

I. Preliminary Syntheses

Figure 1:
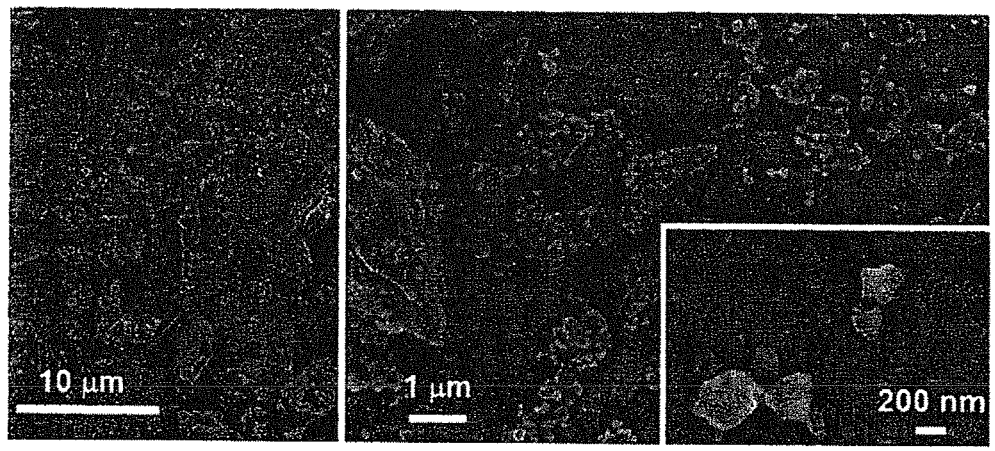
FIG. 1 represents SEM (Scanning Electron Microscopy) images of the material MIL-53nano synthesized according to example 2.

Example 1: Synthesis of Iron(III) Acetate, Precursor Used and Ligand Syntheses a) Synthesis A: Iron(III) Acetate For the synthesis A of the iron(III) acetate, used in the syntheses of MOF materials according to the invention described in the following examples, reference may be made to the publication C. T. Dziobkowski, et al. *Inorg. Chem.*, 1982, 21, 671 [25].

The synthesis A is as follows: 6.72 g of metallic iron powder (Riedel-de Haën, 99%), 64 ml of deionized water and 33.6 mL of 70% perchloric acid in water (Riedel-de Haën) are mixed together with magnetic stirring and heated at 50° C. for 3 hours. After stopping the heating, the solution is stirred for 12 hours. The residual iron metal is removed by settling, and the container is then changed. 20.6 ml of aqueous hydrogen peroxide solution (Alfa Aesar, 35%) are added dropwise with stirring, the mixture being maintained in an ice bath at 0° C. 19.7 g of sodium acetate (Aldrich, 99%) are added to the blue solution with stirring, while maintaining the solution at 0-5° C. The solution is allowed to evaporate for 3 days under a fume cupboard in a glass crystallizing dish (volume=0.5 l). Finally, the red crystals of iron acetate are recovered by filtration and washed very quickly with ice-cold deionized water. The crystals are then air-dried.

b) Synthesis B: 2,5-diperfluoro-1,4-benzenedicarboxylic acid

The synthesis is performed according to the operating protocol described by Kim et al., *Chem. Commun.*, 2005, 372-374.

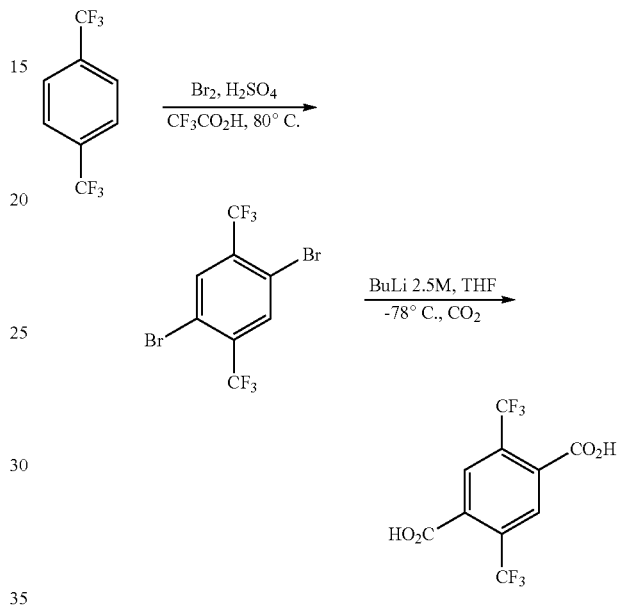

Synthesis of 2,5-dibromo-1,4-bis(trifluoromethyl)-benzene 1,4-Bis(trifluoromethyl)benzene (19 g, 88.7 mmol, ABCR), trifluoroacetic acid (250 ml, SDS) and 99% sulfuric acid (60 ml, Acros) are successively added to a one-liter round-bottomed flask equipped with a condenser and a magnetic bar. N-Bromosuccinimide (47.4 g, 267 mmol, Aldrich) is added portionwise at 60° C. over a period of 5 hours. Stirring is continued for 48 hours at this temperature and the medium is then poured into ice (500 ml). The precipitate thus formed is filtered off and dried under vacuum (1 mmHg) for 24 hours and then purified by sublimation to give 30 g (91%) of a white solid.

Melting point: 65±0.2° C.; 1H NMR (200 MHz, CDCl$_3$): 8.01 (2H, s); 19F NMR (188 MHz, CDCl$_3$): −64.1 (2×CF3, s).

Synthesis of 2,5-bis(trifluoromethyl)terephthalic acid

A solution of 2,5-dibromo-1,4-bis(trifluoromethyl)-benzene (16 g, 43 mmol) in THF (100 ml, Acros) is added dropwise to a solution at −78° C. of butyllithium BuLi (2.5 M in hexane, 38.4 ml, 67.2 mmol, Aldrich) in THF (75 ml) in a one-liter two-necked flask equipped with a dropping funnel and a magnetic bar. After stirring for 30 minutes at this temperature, finely ground cardice (200 g) is introduced into the reaction medium. The temperature is allowed to return to room temperature and the medium is extracted with a sodium hydroxide solution (2M, 3×100). The aqueous phases are combined and acidified with 2M hydrochloric acid solution. The precipitate thus formed is filtered off and dried under vacuum (1 mmHg) for 24 hours to give 11 g (84%) of a white solid.

Melting point: decomposition at 230° C.; 1H NMR (200 MHz, acetone-$d_6$): 8.31 (2H, s, aromatic); 19F NMR (188 MHz, acetone-$d_6$): −55.9 (2×CF3, s).

c) Synthesis C: 2-methylterephthalic acid

2-Methylterephthalic acid is obtained according to the synthetic method described by L. Anzalone, J. A. Hirsch. *J. Org. Chem.* 1985. 50. 2128-213:

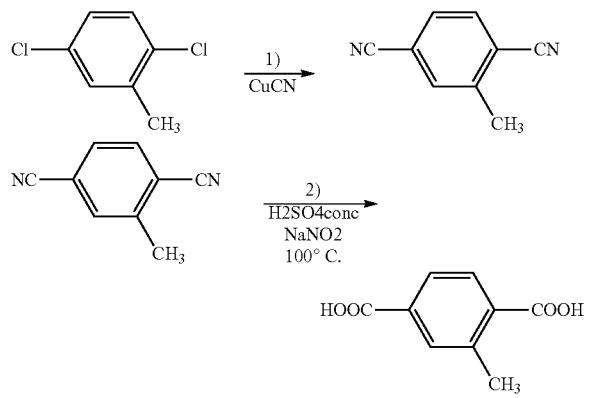

1) 10 g of CuCN (111.6 mmol) and 4.2 ml of 2,5-dichlorotoluene (30.5 mmol) in 26 ml of N-methylpyrrolidinone are placed in a round-bottomed flask. The mixture is refluxed (200° C.) for 24 hours so as to substitute the Cl atoms with nitrile groups.

After stopping the heating, 50 ml of aqueous 20% $NH_4OH$ solution and 35 ml of toluene are added to the reaction medium. The mixture is stirred, and once it has cooled to room temperature, 100 ml of ether and 50 ml of 20% $NH_4OH$ solution are added thereto. The two phases thus obtained are separated by successive additions of ether (250 ml) and finally centrifuged (difficult separation). The organic phase is then washed successively with 10% $NH_4OH$ solution (4×50 ml, until the basic aqueous phase no longer has a blue coloration), then with $H_2O$ and finally with 10% HCl solution and with saturated NaCl solution. After drying over $MgSO_4$, filtering through paper and evaporating off the solvent, 2.9 g of a yellow product are obtained (Yield of 67%).

2) The 2-methylterephthalonitrile thus obtained is then added to 70 ml of 95% $H_2SO_4$, the mixture is maintained at 100° C. overnight, and after stopping the heating, 35 ml of $H_2O$ are added thereto and, once at room temperature, 6.6 g of $NaNO_2$ dissolved in 30 ml of $H_2O$ are added. The whole is maintained at 110° C. overnight. Finally, after adding 200 ml of $H_2O$ with stirring, filtering through a Büchner funnel, washing with water and drying under vacuum at 50° C. overnight, 2.13 g of 2-methylterephthalic acid are obtained in the form of a whitish powder (Yield of 58%).

d) Synthesis D: 3,5,3',5'-tetramethylbiphenyl-4,4'-dicarboxylic acid

The reaction scheme of this synthesis is represented below:

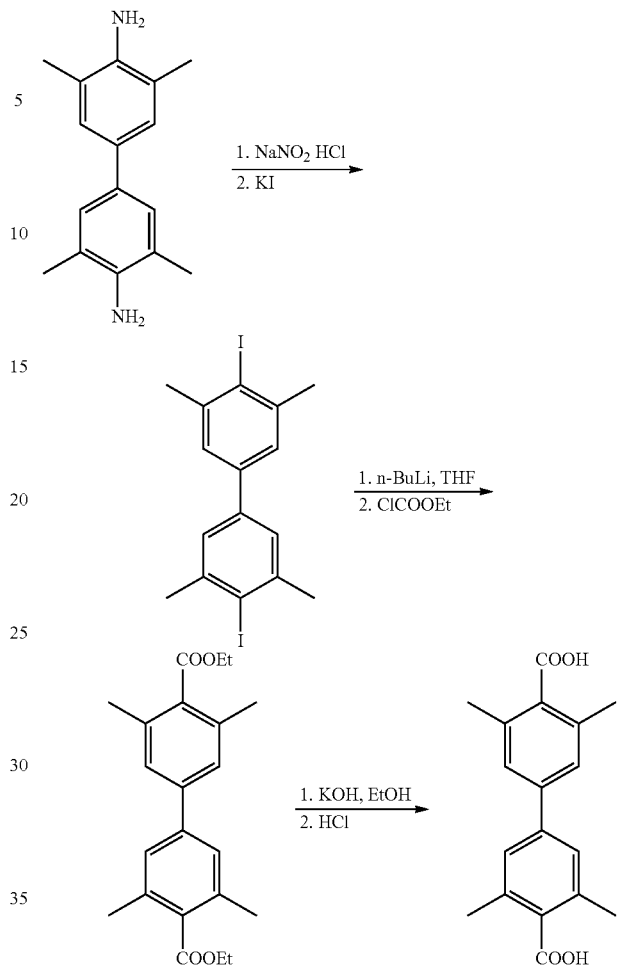

1st Step:

10.2 g of tetramethylbenzidine (98%, Alfa Aesar) are suspended in 39 ml of concentrated hydrochloric acid (37%, sold by the company Aldrich) at 0° C. The diazotization was performed by adding a sodium nitrite solution (6 g in 50 ml of water). After stirring for 15 minutes at 0° C., a potassium iodide solution (70 g in 200 ml of water) was added slowly to the resulting violet solution. Once the addition is complete, the mixture is stirred for 2 hours at room temperature. The resulting black suspension is filtered to recover a black precipitate, which is washed with water. The solid is suspended in dichloromethane (DCM, 98%, sold by the company SDS) and a saturated sodium thiosulfate solution is added, causing decolorization. After stirring for 1 hour, the organic phase is separated out by settling and the aqueous phase is extracted with DCM. The organic phase is dried over sodium sulfate and then evaporated to give the diiodo intermediate in the form of a grayish solid. Elution with pure pentane on a column of silica (sold by the company SDS) gives a mixture of the monoiodo and diiodo compounds. The mixture of these compounds was used directly in the following step.

2nd Step:

7.2 g of the crude iodo compound are dissolved in 100 ml of tetrahydrofuran (THF, distilled over sodium). After cooling to −78° C., 35 ml of n-butyllithium in cyclohexane (2.5 M, sold by the company Aldrich) are added. The solution is allowed to warm to room temperature, and a white suspension appears after 2 hours. It is again cooled to −78° C. and 12 ml of ethyl chloroformate are added. The mixture is left at room temperature, and a clear yellow solution is obtained after 1 hour. Partition between water and dichloromethane, followed by extraction with dichloromethane gives the crude diester. This product is purified by chromatography on silica gel, eluting with a 1/9 Et$_2$O/pentane mixture (front ratio: Rf=0.3). 6.3 g of diester are obtained in the form of a colorless solid (yield of 42% starting from benzidine).

Characterization of the diester obtained: 1H NMR (300 MHz, CDCl3): δ (ppm): 1.29 (t, J=7.2 Hz, 6H), 2.29 (s, 13H); 4.31 (q, J=7.2 Hz, 4H); 7.12 (s, 4H). 13C NMR (75 MHz, CDCl3): δ (ppm): 14.3 (CH3), 19.9 (CH3), 61.0 (CH2), 126.5 (CH), 133.2 (Cq), 135.5 (Cq), 141.4 (Cq), 169.8 (Cq).

3rd Step:

Finally, the diester is saponified with 9.7 g of potassium hydroxide (sold by the company VWR) in 100 ml of 95% ethanol (sold by the company SDS) at reflux for 5 days. The solution is concentrated under vacuum and the product is dissolved in water. Concentrated hydrochloric acid is added to pH 1, and a white precipitate is formed. It is recovered by filtration, washed with water and dried. 5.3 g of diacid are thus obtained in the form of a white solid (quantitative yield).

e) Synthesis E: 3,3'-dimethylbiphenyl-4,4'-dicarboxylic acid

The reaction scheme for this synthesis is represented below:

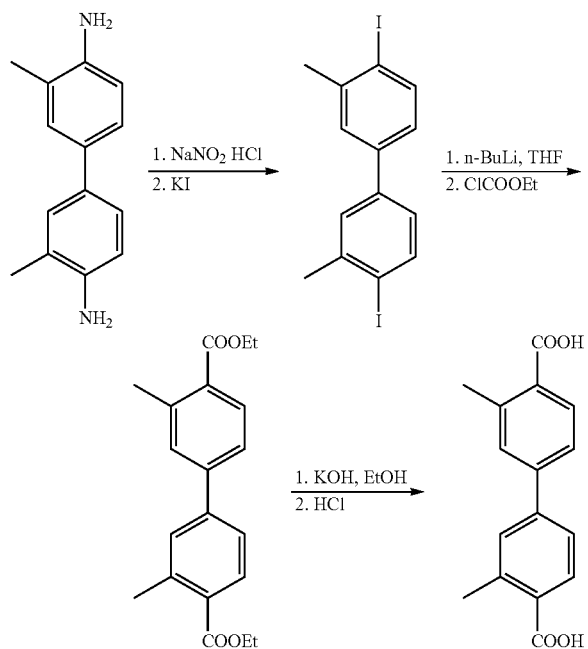

The same procedure as that described for synthesis D was used, starting with 12.1 g of dimethylbenzidine. After the first step, 18.4 g of 3,3'-dimethyl-4,4'-diiodobiphenyl are obtained (yield: 74%).

Characterization of the diiodo compound obtained: 1H NMR (300 MHz, CDCl3): δ (ppm): 2.54 (s, 6H), 7.10 (dd, J=2.2 and 8.1 Hz, 2H), 7.46 (d, J=2.2 Hz, 2H), 7.90 (d, J=8.1 Hz, 2H). 13C NMR (75 MHz, CDCl3): δ (ppm): 28.3 (CH3), 100.3 (Cq), 126.0 (CH), 128.3 (CH), 139.4 (CH), 140.4 (Cq), 141.9 (Cq).

After the second and third steps, 6.9 g of 3,3'-dimethylbiphenyl-4,4'-dicarboxylic acid are obtained starting with the 18.4 g of diiodo compound.

Characterization of the compounds obtained: the diester obtained after the second step and the diacid obtained after the third step have spectroscopic signatures identical to those described in the literature (Shiotani Akinori, Z. Naturforsch. 1994, 49, 12, 1731-1736).

f) Synthesis F: 3,3'-dichloro-4,4'-azobenzenedicarboxylic acid 15 g of o-chlorobenzoic acid (Aldrich, 98%) and 50 g of sodium hydroxide are placed in 225 ml of distilled water and heated to 50° C. with stirring. A solution of 100 g of glucose (Aldrich, 96%) dissolved in 150 ml of water is added. The mixture is stirred for 15 minutes and is then sparged with air for 3 hours at room temperature. The disodium salt is recovered by filtration, washed with ethanol and then dissolved again in 120 ml of water. Hydrochloric acid (Aldrich VWR, 37%) is added to obtain a pH equal to 1. The solid is recovered by filtration and dried under vacuum at 90° C.

g) Synthesis G: 3,5,3',5'-azobenzenetetracarboxylic acid 19 g of 5-nitroisophtalic acid (Aldrich, 98%) and 50 g of sodium hydroxide are placed in 250 ml of distilled water and heated to 50° C. with stirring. A solution of 100 g of glucose (Aldrich, 96%) dissolved in 150 ml of water is added. The mixture is stirred for 15 minutes and then sparged with air for 3 hours at room temperature. The resulting disodium salt is recovered by filtration and dissolved in 300 ml of water at room temperature. Hydrochloric acid (VWR, 37%) is added to obtain a pH equal to 1. The solid is recovered by filtration and dried under vacuum at 90° C.

h) Synthesis H: Chloroterephthalic Acid 6 g (0.043 mol) of chloroxylene (sold by the company Aldrich, >99%), 16 ml of nitric acid (sold by the company VWR, 70%) and 60 ml of distilled water are introduced into a 120 ml Teflon body. This body is placed in a Paar metal bomb and heated at 170° C. for 12 hours. The product is recovered by filtration and then washed thoroughly with distilled water. A yield of 75% is obtained.

1H NMR (300 MHz, d6-DMSO): δ (ppm): 7.86 (d, J=7.8 Hz), 7.93 (dd, J=7.8; 1.2 Hz), 7.96 (d, J=1.2 Hz).

II. Nanoparticles According to the Invention and Processes for Preparing the Nanoparticles According to the Invention Example 2: Synthesis of Iron Carboxylate Nanoparticles a) Synthesis of MIL-53Nano Nanoparticles The solid MIL-53nano was obtained in the form of nanoparticles starting with 270 mg of FeCl$_3$.6H$_2$O (1 mmol; Alfa Aesar, 98%) and 166 mg of terephthalic acid (1 mmol; 1,4-BDC; Aldrich, 98%) in 5 ml of dimethylformamide (DMF; Fluka, 98%), the whole introduced into a Teflon body placed in a metal body (autoclave) of Paar brand. The whole is heated at 150° C. for 2 or 4 hours. After cooling to room temperature, the solid is recovered by centrifugation at 5000 rpm (revolutions per minute) for 10 minutes.

200 mg of the solid are then suspended in 100 ml of distilled water with stirring for 15 hours to remove the residual solvent present in the pores. Next, the solid is recovered by centrifugation at 5000 rpm for 10 minutes. The particle size measured by light scattering is about 350 nm.

The scanning electron microscopy (SEM) images of the material MIL-53 of the present invention are presented in FIG. 1 and show the presence of two populations of particles, one of large size (about 5 μm) and others that are smaller (about 350 μm). The large particles are rather rhombohedric, undoubtedly recrystallized carboxylic acid; on the other hand, the morphology of the small particles is rather spherical, and is in the form of aggregates.

b) Synthesis of MIL-89nano Nanoparticles

The synthesis of MIL-89nano is performed starting with 210 mg of iron acetate (0.33 mmol; synthesized in the laboratory according to synthesis A described above) and 142 mg of muconic acid (1 mmol; Fluka, 97%) in the presence of 5 ml of ethanol (Riedel-de Haën, 99.8%) with addition of 0.25 ml of 2M sodium hydroxide (Alfa Aesar, 98%), the whole introduced into a Teflon body placed in a metal body (autoclave) of Paar brand. The whole is heated at 100° C. for 12 hours.

After cooling to room temperature, the product is recovered by centrifugation at 5000 rpm for 10 minutes. 200 mg of the solid are then suspended in 100 ml of distilled water with stirring for 15 hours to remove the residual solvent present in the pores. The solid is then recovered by centrifugation at 5000 rpm for 10 minutes.

Figure 2:
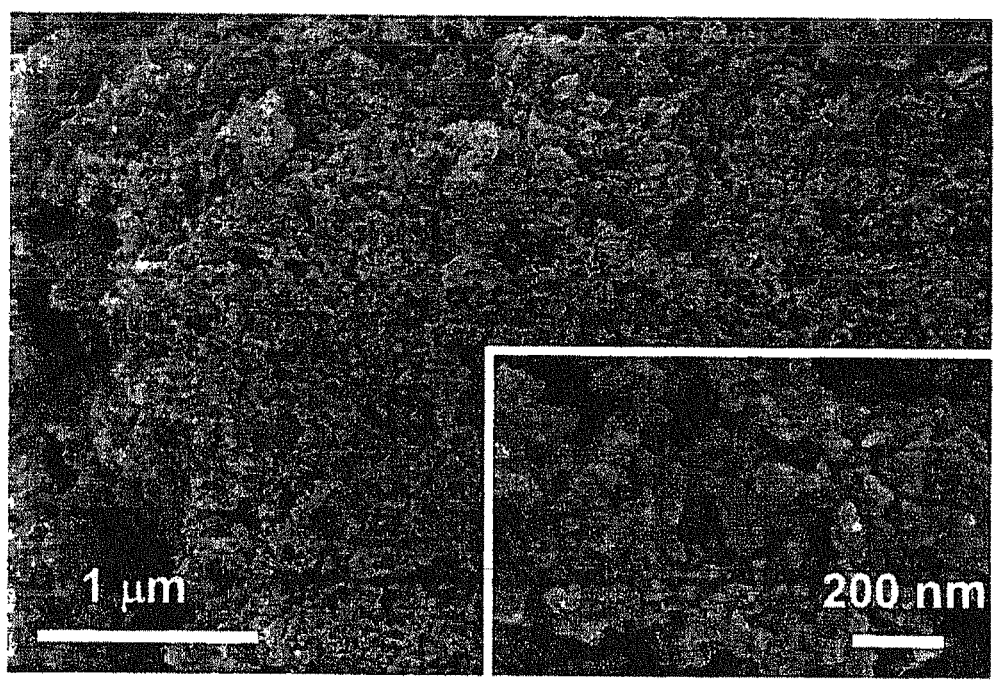
FIG. 2 represents the SEM (Scanning Electron Microscopy) images of the material MIL-89nano synthesized according to example 2.

The particle size measured by light scattering is 400 nm. The nanoparticles show a rounded and slightly elongated morphology, with a very homogeneous particle size, measured by scanning electron microscopy, of 50-100 nm (FIG. 2). It is thus clear that the 400 nm objects measured by light scattering correspond to aggregates of MIL-89nano particles.

c) Synthesis of MIL-88Anano Nanoparticles

In order to obtain the material MIL-88Anano, 270 mg of $FeCl_3.6H_2O$ (1 mmol; Alfa Aesar, 98%) and 112 mg of fumaric acid (1 mmol; Acros, 99%) are mixed in 15 ml of ethanol (Riedel-de Haën, 99.8%) and 1 ml of acetic acid (Aldrich, 99.7%). The solution is placed in a glass flask and heated at 65° C. for 2 hours. The solid is recovered by centrifugation at 5000 rpm for 10 minutes.

200 mg of the solid are suspended in 100 ml of distilled water with stirring for 15 hours to remove the residual solvent present in the pores. The solid is then recovered by centrifugation at 5000 rpm for 10 minutes.

Figure 3:
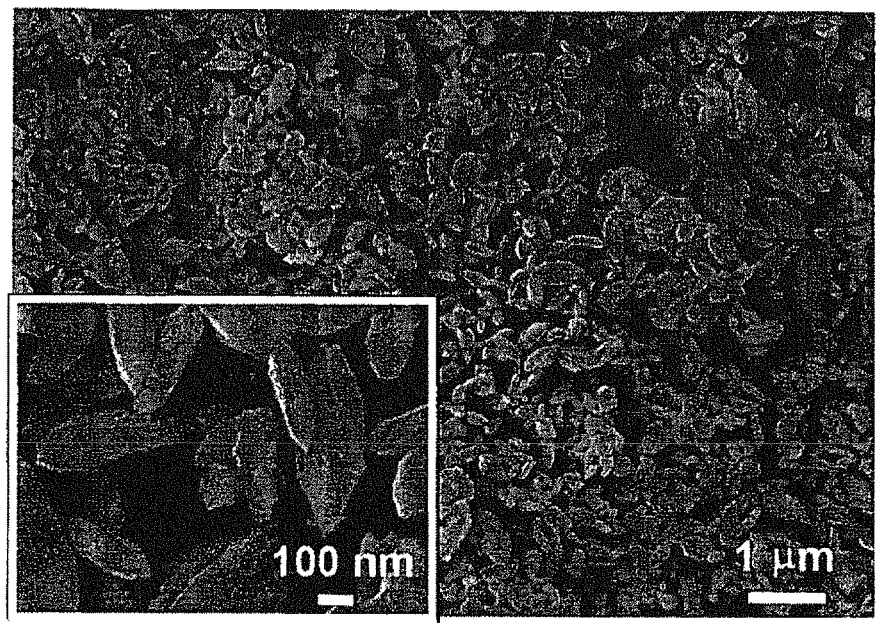
FIG. 3 represents the SEM images of the material MIL-88Anano synthesized according to example 2.

The particle size measured by light scattering is 250 nm. Scanning electron microscopy (FIG. 3) shows elongated particles with edges. There are two particle sizes, about 500 nm and 150 nm. The size measured by light scattering thus corresponds to an average size of MIL-88Anano.

d) Synthesis of MIL-100nano Nanoparticles

The synthesis of MIL-100nano is performed starting with 270 mg of $FeCl_3.6H_2O$ (1 mmol; Alfa Aesar, 98%) and 210 mg of 1,3,5-benzenetricarboxylic acid (1,3,5-BTC; 1 mmol; Aldrich, 95%) in 3 ml of distilled water. The whole is introduced into a Teflon body placed in a metal body (autoclave) of Paar brand. The whole is heated for 12 hours at 100° C. The product is recovered by centrifugation at 5000 rpm for 10 minutes.

200 mg of solid are suspended in 100 ml of distilled water with stirring at reflux for 3 hours to remove the residual acid present in the pores. The solid is then recovered by centrifugation at 5000 rpm for 10 minutes.

Figure 4:
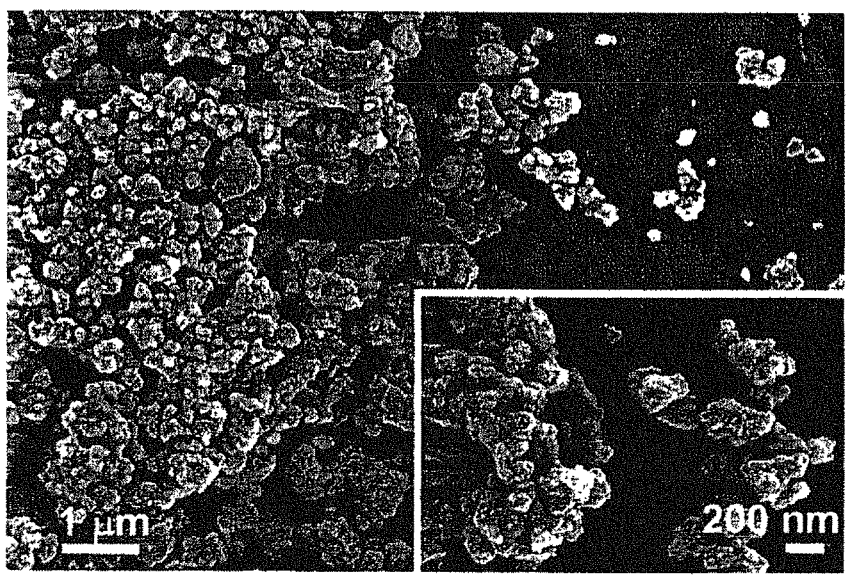
FIG. 4 represents the SEM images of the material MIL-100nano synthesized according to example 2.

The particle size measured by light scattering is 535 nm. Scanning electron microscopy (FIG. 4) shows strong aggregation of the particles. These particles are rather spherical, with an approximate size of 40 to 60 nm.

e) Synthesis of MIL-101nano Nanoparticles

To produce the solid MIL-101nano, 270 mg of $FeCl_3.6H_2O$ (1 mmol; Alfa Aesar, 98%) and 250 mg of 1,4-benzenedicarboxylic acid (1.5 mmol; 1,4-BDC Aldrich, 98%) are mixed in 10 ml of dimethylformamide (Fluka, 98%), and the whole is placed in a Paar bomb and heated at 100° C. for 15 hours. The solid is recovered by centrifugation at 5000 rpm for 10 minutes.

To remove the residual acid present in the pores, the product is heated at 200° C. under vacuum for 1 day. It should be noted that it should be kept under vacuum or under an inert atmosphere, since the product is not stable in air or in the presence of water. The particle size measured by light scattering is 310 nm.

f) Synthesis of MIL-88Btnano Nanoparticles

The solid MIL-88Btnano is synthesized from 270 mg of $FeCl_3.6H_2O$ (1 mmol; Alfa Aesar, 98%), 222 mg of 1,4-benzenetetramethyldicarboxylic acid (1 mmol; Chem Service) and 10 ml of dimethylformamide (Fluka, 98%) in the presence of 0.4 ml of aqueous 2M NaOH solution. The whole is introduced into a Teflon body placed in a metallic body (autoclave) of Paar brand, and then heated at 100° C. for 2 hours. After cooling to room temperature (the metal bomb is cooled in cold water), the product is recovered by centrifugation at 5000 rpm for 10 minutes.

200 mg of the solid are then suspended in 100 ml of distilled water with stirring for 15 hours to remove the residual solvent present in the pores. The solid is recovered by centrifugation at 5000 rpm for 10 minutes.

The particle size measurement by light scattering shows two populations of nanoparticles of 50 and 140 nm.

Figure 5:
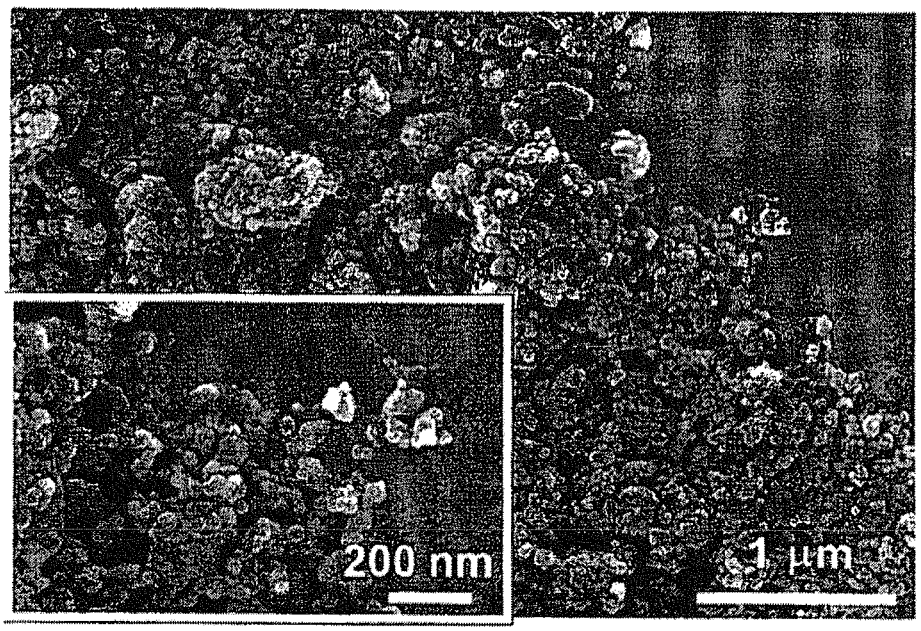
FIG. 5 represents the SEM images of the material MIL-88Btnano synthesized according to example 2.

Scanning electron microscopy (FIG. 5) shows that the particles have a spherical morphology with a size of about 50 nm. Only a minor fraction has a size of about 200 nm. Agglomerates of small particles may also be observed therein.

g) Synthesis of MIL-88Bnano Nanoparticles

The solid MIL-88Bnano is synthesized from 240 mg of iron acetate (0.33 mmol, synthesized in the laboratory according to synthesis A described above) and 166 mg of 1,4-benzenedicarboxylic acid (1 mmol; 1,4-BDC Aldrich, 98%) introduced into 5 ml of methanol (Aldrich, 99%). The whole is introduced into a Teflon body placed in a metal body (autoclave) of Paar brand, and heated at 100° C. for 2 hours. After cooling to room temperature (the metal bomb is cooled in cold water), the product is recovered by centrifugation at 5000 rpm for 10 minutes.

200 mg of the solid are suspended in 100 ml of distilled water with stirring for 15 hours to remove the residual solvent. The solid is then recovered by centrifugation at 5000 rpm for 10 minutes.

The particle size measurement by light scattering shows a bimodal distribution of nanoparticles of 156 and 498 nm.

Figure 6:
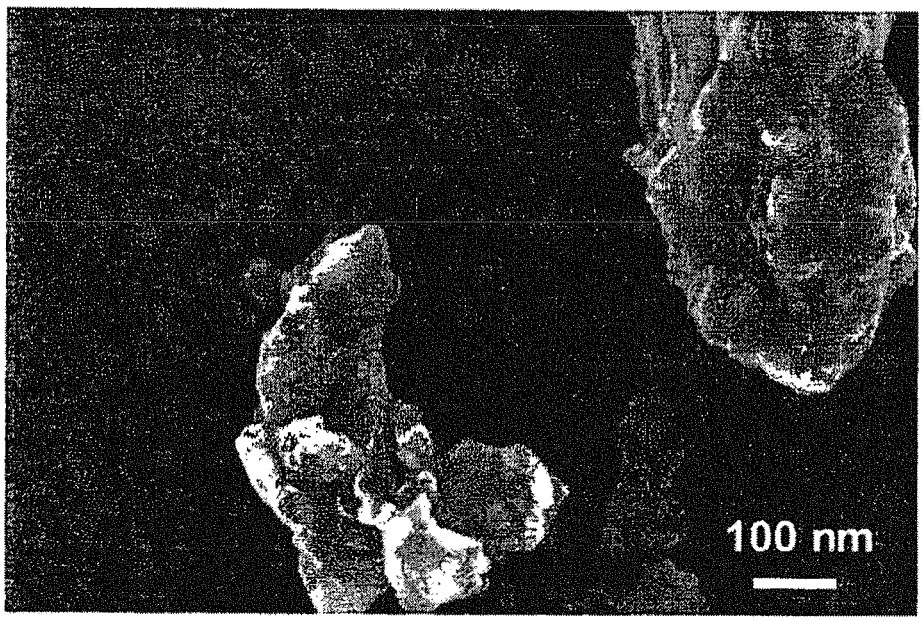
FIG. 6 represents the SEM images of the material MIL-88Bnano synthesized according to example 2.

The particle morphology observed by microscopy is very irregular, with a mean size close to 300 nm (FIG. 6).

The particle size determination by light scattering was performed with a Malvern Zetasizer Nano series—Nano-ZS machine; Zen 3600 model; serial No. 500180; UK.

Scanning electron microscopy was performed using a Topcon microscope (Akashi) EM 002B ultra-high resolution 200 kV.

The differences between the values obtained from these two techniques are explained, on the one hand, by the orange coloration of iron carboxylate particles, which is not ideal given the red color of the laser beam of the light scattering apparatus, and, on the other hand, by a more or less pronounced tendency of the particles to agglomerate.

h) MIL-102 (Fe) or $Fe_6O_2X_2[C_{10}H_2-(CO_2)_4]_3 \cdot nH_2O$ (X=F, Cl ... )

Synthesis of the Non-Fluoro Solid MIL-102(Fe):

270 mg (1 mmol) of $FeCl_3 \cdot 6H_2O$ (Alfa Aesar, 98%) and 268 mg (1 mmol) of 1,4,5,8-naphthalenetetracarboxylic acid are dispersed in 5 ml of distilled water. The mixture is left in a 23 ml Teflon body placed in a Paar metallic bomb for 15 hours at 100° C. The solid is recovered by filtration.

Characteristic Data for the Solid MIL-102(Fe):

This compound has a low specific surface area (Langmuir surface area: 101 m²/g) with nitrogen at 77 K.

Production of the Fluoro Solid MIL-102(Fe):

0.2 g of non-fluoro solid MIL-102(Fe) of formula $Fe_6O_2Cl_2[C_{10}H_4(CO_2)_4]_3 \cdot nH_2O$ obtained according to the procedure described previously is placed in contact with 1 g of sodium fluoride NaF in 100 ml of distilled water. The mixture is stirred in a 125 ml Teflon body for 15 hours at room temperature. The solid is recovered by filtration and washed five times with distilled water to remove the traces of NaF. Semi-quantitative analysis by EDX indicates a fluorine content of 0.17 fluorine per iron. The solid thus treated has an approximate formula of the type $Fe_6O_2F(OH)[C_{10}H_4(CO_2)_4]_3 \cdot nH_2O$.

i) Analytical Data for the Iron Carboxylate Nanoparticles

The particle size is measured with a Coulter N4MD light scattering machine (Coulter Electronics, Margency, France) using aqueous suspensions of the material at 0.5 mg/ml.

The potential Z is measured using aqueous 0.5 mg/ml suspensions in a 0.1 M NaCl medium on a Malvern Zetasizer Nano series machine—Nano-ZS equipment, model Zen 3600.

The particle size is measured on the Z potential machine using aqueous 0.5 mg/ml solutions of material.

Table 1 below presents the characteristics of the various MOF materials obtained, especially the size of the nanoparticles, estimated by quasi-elastic light scattering or by electron microscopy, the pore size and the zeta potential.

TABLE 1

"MIL" structures of a number of iron(III) carboxylates according to the invention.

| MIL-n nanosolid | Organic fraction | Formula |
|---|---|---|
| MIL-53 | 1,4-benzenedicarboxylic acid (terephthalic acid or 1,4-BDC acid) | $Fe(OH)[O_2C-C_6H_4-CO_2] \cdot H_2O$ |
| MIL-88A | Fumaric acid | $Fe_3OX[O_2C-C_2H_2-CO_2]_3 \cdot nH_2O$ |
| MIL-88B | Terephthalic acid | $Fe_3OX[O_2C-C_6H_4-CO_2]_3 \cdot nH_2O$ |
| MIL-88BT | Tetramethyl-terephthalic acid | $Fe_3OX[O_2C-C_6(CH_3)_4-CO_2]_3 \cdot nH_2O$ |
| MIL-89 | Muconic acid | $Fe_3OCl[O_2C-C_4H_4-CO_2]_3 \cdot nH_2O$ |
| MIL-100 | 1,3,5-benzenetricarboxylic acid (1,4-BTC acid) | $Fe_3OX[C_6H_3-[CO_2]_3] \cdot nH_2O$ |
| MIL-101 | Terephthalic acid | $Fe_3OX[O_2C-C_6H_4-CO_2]_3 \cdot nH_2O$ |

TABLE 2

Characteristics of the "MIL" structures of iron(III) carboxylates

| MIL-n | % of Iron* | Pore diameter (Å)** | Particle size (diffusion) (nm) | Particle size (microscopy) (nm) | Z pot.*** (mV) | Flex.**** | Metallic base |
|---|---|---|---|---|---|---|---|
| MIL-53 | 23.6% | 8.6 | 350 | 350 and 5000 | 6 | yes | Octahedral chain |
| MIL-88A | 30.8% | 6 | 250 | 150 and 500 | 13-34 | yes | Octahedral trimer |
| MIL-88B | 24.2% | 9 | 150 and 500 | 300 | 14 | yes | Octahedral trimer |
| MIL-88BT | 19.4% | 8 | 50 and 140 | 50 and 200 | 19 | yes | Octahedral trimer |
| MIL-89 | 26.2% | 11 | 400 | 50-100 | 7 | yes | Octahedral trimer |
| MIL-100 | 27.3% | 25-29 | 530 | 40-60 | −25 | no | Octahedral trimer |

TABLE 2-continued

Characteristics of the "MIL" structures of iron(III) carboxylates

| MIL-n | % of Iron* | Pore diameter (Å)** | Particle size (diffusion) (nm) | Particle size (microscopy) (nm) | Z pot.*** (mV) | Flex.**** | Metallic base |
|---|---|---|---|---|---|---|---|
| MIL-101 | 24.2% | 29-34 | 310 | — | 29 | no | Octahedral trimer |

*Theoretical % of iron in the dry phase
**Pore size calculated from the crystallographic structures
***Z potential
****Flexibility

Example 3: Synthesis of MOF Materials Based on Functionalized Ligands a) MIL-101-Cl (Fe) or $Fe_3O[Cl\text{---}C_6H_3\text{---}(CO_2)_2]_3 \cdot X \cdot nH_2O$ (X=F, Cl, OH)

The synthetic conditions are as follows: 0.27 g (1 mmol) of $FeCl_3 \cdot 6H_2O$ and 210 mg of chloro-1,4-benzenedicarboxylic acid (1.0 mmol, Cl-1,4-BDC, synthesized according to synthesis H described in Example 1) are dispersed in 10 ml of DMF (dimethylformamide, Fluka, 98%). The whole is left for 12 hours at 100° C. in a 23 ml Teflon body placed in a Paar metallic bomb. The solid is then filtered off and washed with acetone.

Optimization of the pore emptying conditions is underway.

Mesh parameters of the solid MIL-101(Fe) at 298 K: a=89.0 Å and V=707 000 Å$^3$, space group Fd-3m (No. 227).

The monodisperse particle size (polydispersity index, PDI=0.225) measured by light scattering is 400 nm.

b) MIL-101-NH$_2$(Fe) or $Fe_3O[NH_2\text{---}C_6H_3\text{---}(CO_2)_2]_3 \cdot X \cdot nH_2O$ (X=F, Cl, OH)

2.25 g (0.92 mmol) of $FeCl_3 \cdot 6H_2O$ and 0.75 mg of amino-1,4-benzenedicarboxylic acid (0.41 mmol, NH$_2$-1,4-BDC, Aldrich, 99%) are dispersed in 50 ml of DMF (dimethylformamide, Fluka, 98%). The whole is left for 24 hours at 110° C. in a 23 ml Teflon body placed in a Paar metallic bomb. The solid is then filtered off and washed with acetone. The solid is heated at 120° C. under vacuum for 16 hours to remove the acid remaining in the pores. On the other hand, optimization of these pore-emptying conditions is still underway.

Mesh parameters of the solid MIL-101(Fe) at 298 K: a=89.0 Å and V=707 000 Å$^3$, space group Fd-3m (No. 227).

The monodisperse particle size (PDI=0.086) measured by light scattering is 391 nm.

c) MIL-101-2CF$_3$ (Fe) or $Fe_3O[(CF_3)_2\text{---}C_6H_2\text{---}(CO_2)_2]_3 \cdot X \cdot nH_2O$ (X=F, Cl, OH)

135 mg (0.5 mmol) of $FeCl_3 \cdot 6H_2O$ and 151 mg of 2,5-diperfluoro-1,4-benzenedicarboxylic acid (0.5 mmol, 2CF$_3$-1,4-BDC, synthesized according to synthesis B described in Example 1) are dispersed in 5 ml of DMF (Fluka, 98%). The whole is left for 12 hours at 90° C. in a 23 ml Teflon body placed in a Paar metallic bomb. The solid is then recovered by centrifugation at 10 000 rpm for 10 minutes.

Optimization of the pore-emptying conditions is underway.

Mesh parameters of the solid MIL-101(Fe) at 298 K: a=89.0 Å and V=707 000 Å$^3$, space group Fd-3m (No. 227).

The monodisperse particle size (PDI=0.145) measured by light scattering is 340 nm.

d) MIL-88B-NO$_2$ (Fe) or $Fe_3O[C_6H_3NO_2\text{---}(CO_2)_2]_3 \cdot X \cdot nH_2O$ (X=F, Cl, OH)

0.27 g of $FeCl_3 \cdot 6H_2O$ (1 mmol, Alfa Aesar, 98%) and 211 mg (1 mmol) of 1,4-nitroterephthalic acid (Acros, 99%) are dispersed in 5 ml of distilled water. The whole is left in a 23 ml Teflon body placed in a Paar metallic bomb for 12 hours at 100° C. The solid is recovered by filtration.

200 mg of the solid are suspended in 10 ml of absolute ethanol in a 23 ml Teflon body placed in a Paar metallic bomb for 12 hours at 100° C. to remove the acid remaining in the pores. Next, the solid is recovered by filtration and dried at 100° C.

TABLE 3

Elemental analysis (CNRS, Vernaison)

| | mass % | | |
|---|---|---|---|
| Element | % iron | % carbon | % nitrogen |
| MIL-88B NO$_2$ | 20.6 | 39.3 | 4.6 |

The monodisperse particle size (PDI=0.005) measured by light scattering is 345 nm.

e) MIL-88B-2OH (Fe) or $Fe_3O[C_6H_2(OH)_2\text{---}(CO_2)_2]_3 \cdot X \cdot nH_2O$ (X=F, Cl, OH)

354 mg of $Fe(ClO_4)_3 \cdot xH_2O$ (1 mmol, Aldrich, 99%) and 198 mg (1 mmol) of 1,4-dihydroxyterephthalic acid (obtained by hydrolysis of the corresponding diethyl ester, Aldrich, 97%) are dispersed in 5 ml of DMF (Fluka, 98%). The whole is left in a 23 ml Teflon body placed in a Paar metallic bomb for 12 hours at 85° C. The solid is recovered by filtration and then calcined at 150° C. under vacuum for 15 hours to remove the acid remaining in the pores.

TABLE 4

Elemental analysis (CNRS, Vernaison)

| | mass % | |
|---|---|---|
| Element | % iron | % carbon |
| MIL-88B 2OH | 15.4 | 36.5 | f) MIL-88B-NH$_2$ (Fe) or Fe$_3$O[C$_6$H$_3$NH$_2$—(CO$_2$)$_2$]$_3$.X.nH$_2$O (X=F, Cl, OH)

0.27 g of FeCl$_3$.6H$_2$O (1 mmol, Alfa Aesar, 98%) and 180 mg (1 mmol) of 1,4-aminoterephthalic acid (Fluka, 98%) are dispersed in 5 ml of absolute ethanol. The whole is left in a 23 ml Teflon body in a Paar metallic bomb for 3 days at 100° C. The solid is recovered by filtration and then calcined at 200° C. for 2 days to remove the acid remaining in the pores.

The monodisperse particle size (PDI=0.268) measured by light scattering is 102 nm.

g) MIL-88B-CH$_3$ (Fe) or Fe$_3$O[C$_6$H$_3$CH$_3$—(CO$_2$)$_2$]$_3$.X.nH$_2$O (X=F Cl, OH)

354 mg of Fe(ClO$_4$)$_3$.xH$_2$O (1 mmol, Aldrich, 99%) and 180 mg (1 mmol) of 1,4-methylterephthalic acid (prepared according to synthesis C) are dispersed in 5 ml of methanol (Fluka, 99%). The whole is left in a 23 ml Teflon body placed in a Paar metallic bomb for 3 days at 100° C. The solid is recovered by filtration.

200 mg of the solid are suspended in 10 ml of DMF with stirring at room temperature to exchange the remaining acid with DMF, and the DMF is then removed by evaporation at 150° C. under vacuum for 12 hours.

The monodisperse particle size (PDI=0.231) measured by light scattering is 430 nm.

h) MIL-88B-Cl (Fe) or Fe$_3$O[C$_6$H$_3$Cl—(CO$_2$)$_2$]$_3$.X.nH$_2$O (X=F, Cl, OH)

354 mg of Fe(ClO$_4$)$_3$.xH$_2$O (1 mmol, Aldrich, 99%) and 200 mg (1 mmol) of 1,4-chloroterephthalic acid (prepared according to the synthesis described in Example 1) are dispersed in 10 ml of DMF with 0.1 ml of 5M HF (hydrofluoric acid, SDS, 50%) and 0.1 ml of 1M HCl (hydrochloric acid, Aldrich, 37%). The whole is left in a 23 ml Teflon body placed in a Paar metallic bomb for 5 days at 100° C. The solid is recovered by filtration and then calcined at 150° C. under vacuum.

The particle size measured by light scattering is 255 nm, with a second population of more than 1 micron.

i) MIL-88B-4CH$_3$ (Fe) or Fe$_3$O[C$_6$(CH$_3$)$_4$—(CO$_2$)$_2$]$_3$.X.nH$_2$O (X=F, Cl, OH)

0.27 g of FeCl$_3$.6H$_2$O (1 mmol, Alfa Aesar, 98%) and 222 mg (1 mmol) of 1,4-tetramethylterephthalic acid (Chem Service, 95%) are dispersed in 10 ml of DMF (Fluka, 98%) with 0.4 ml of 2M NaOH (Alfa Aesar, 98%). The whole is left in a 23 ml Teflon body placed in a Paar metallic bomb for 12 hours at 100° C. The solid is recovered by filtration.

200 mg of the solid are suspended in 100 ml of water with stirring at room temperature for 12 hours to remove the acid remaining in the pores. The solid is then recovered by filtration.

The monodisperse particle size (PDI=0.005) measured by light scattering is 549 nm.

j) MIL-88B-4F (Fe) or Fe$_3$O[C$_6$F$_4$—(CO$_2$)$_2$]$_3$.X.nH$_2$O (X=F, Cl, OH)

270 mg of FeCl$_3$.6H$_2$O (1 mmol, Alfa Aesar, 98%) and 230 mg (1 mmol) of 1,4-tetrafluoroterephthalic acid (Aldrich, 98%) are dispersed in 10 ml of distilled water. The whole is left in a 23 ml Teflon body placed in a Paar metallic bomb for 12 hours at 85° C. The solid is recovered by filtration.

200 mg of the solid are suspended in 20 ml of water with stirring at room temperature for 2 hours, to remove the acid remaining in the pores. The solid is then recovered by filtration.

The slightly polydisperse particle size (PDI=0.289) measured by light scattering is 399 nm.

k) MIL-88B-Br (Fe) or Fe$_3$O[C$_6$H$_3$Br—(CO$_2$)$_2$]$_3$.X.nH$_2$O (X=F, Cl, OH)

270 mg of FeCl$_3$.6H$_2$O (1 mmol, Alfa Aesar, 98%), 250 mg (1 mmol) of 1,4-bromoterephthalic acid (Fluka, 95%) are dispersed in 10 ml of DMF (Fluka, 98%) with 0.2 ml of 5M HF (SDS, 50%), the whole left in a 23 ml Teflon body placed in a Paar metallic bomb for 12 hours at 150° C. The solid is recovered by filtration and then calcined at 150° C. under vacuum for 15 hours to remove the acid remaining in the pores.

The monodisperse particle size (PDI=0.005) measured by light scattering is 1127 nm.

l) MIL-88B-2CF$_3$ (Fe) or Fe$_3$O[(CF$_3$)$_2$—C$_6$H$_2$—(CO$_2$)$_2$]$_3$.X.nH$_2$O (X=F, Cl, OH)

135 mg of FeCl$_3$.6H$_2$O (0.5 mmol, Alfa Aesar, 98%) and 151 mg (0.5 mmol) of 2,5-difluoro-1,4-terephthalic acid (synthesized according to synthesis B described in Example 1) are dispersed in 5 ml of DMF (Fluka, 98%) with 0.2 ml of 2M NaOH (Alfa Aesar, 98%). The whole is left in a 23 ml Teflon body placed in a Paar metallic bomb for 16 hours at 100° C. The solid is recovered by filtration.

The particle size measured by light scattering is >1 micron.

m) MIL-88D 4CH$_3$ (Fe) or Fe$_3$O[C$_{12}$H$_4$(CH$_3$)$_4$—(CO$_2$)$_2$]$_3$.X.nH$_2$O (X=F, Cl, OH)

354 mg of Fe(ClO$_4$)$_3$.xH$_2$O (1 mmol, Aldrich, 99%) and 298 mg (1 mmol) of tetramethylbiphenyl-4,4'-dicarboxylic acid (prepared according to synthesis D) are dispersed in 5 ml of DMF (Fluka, 98%) with 0.2 ml of 2M NaOH (Alfa Aesar, 98%). The mixture is left in a 23 ml Teflon body placed in a Paar metallic bomb for 12 hours at 100° C. The solid is recovered by filtration.

200 mg of the solid are suspended in 10 ml of DMF with stirring at room temperature for 2 hours to exchange the acid remaining in the pores. The solid is then recovered by filtration and then calcined at 150° C. under vacuum for 15 hours to remove the DMF remaining in the pores.

This compound does not have a surface (greater than 20 m$^2$/g) that is accessible to nitrogen at 77 K, since the dry structure has a pore size that is too small to incorporate nitrogen N$_2$.

The particle size measured by light scattering is >1 micron (2032, PDI=0.005).

n) MIL-88D 2CH$_3$ (Fe) or Fe$_3$O[C$_{12}$H$_6$(CH$_3$)$_2$—(CO$_2$)$_2$]$_3$.X.nH$_2$O (X=F, Cl, OH)

270 mg of FeCl$_3$.6H$_2$O (1 mmol, Alfa Aesar, 98%) and 268 mg (1 mmol) of dimethylbiphenyl-4,4'-dicarboxylic acid (prepared according to synthesis E) are dispersed in 5 ml of DMF (Fluka, 98%) with 0.25 ml of 5M HF (SDS, 50%). The whole is left in a 23 ml Teflon body placed in a Paar metallic bomb for 12 hours at 150° C. The solid is recovered by filtration and then calcined at 150° C. under vacuum for 15 hours to remove the acid remaining in the pores.

The monodisperse particle size (PDI=0.005) measured by light scattering is 458 nm.

o) MIL-88E (Pyr) (Fe) or $Fe_3O[C_4H_3N_2-(CO_2)_2]_3.X.nH_2O$ (X=F, Cl, OH)

270 mg of $FeCl_3.6H_2O$ (1 mmol, Alfa Aesar, 98%) and 204 mg (1 mmol) of 2,5-pyrazinedicarboxylic acid (Aldrich, 98%) are dispersed in 5 ml of DMF (Fluka, 98%) with 0.05 ml of 5M HF (SDS, 50%). The whole is left in a 23 ml Teflon body placed in a Paar metallic bomb for 3 days at 100° C. The solid is recovered by filtration.

The particle size measured by light scattering is >1 micron (2 µm).

p) MIL-88F (Thio) (Fe) or $Fe_3O[C_4H_2S-(CO_2)_2]_3.X.nH_2O$ (X=F, Cl, OH)

354 mg of $Fe(ClO_4)_3.xH_2O$ (1 mmol, Aldrich, 99%) and 258 mg (1 mmol) of thiophene dicarboxylic acid (Aldrich, 99%) are dispersed in 2.5 ml of DMF (Fluka, 98%) with 0.1 ml of 5M HF (SDS, 50%). The whole is left in a 23 ml Teflon body placed in a Paar metallic bomb for 3 days at 100° C. The solid is recovered by filtration.

200 mg of the solid are suspended in 100 ml of water with stirring at room temperature for 12 hours to remove the acid remaining in the pores. The solid is then recovered by filtration.

The particle size measured by light scattering is 449 nm, with a second minor population of more than 1 micron.

q) MIL-53-2OH (Fe) or $FeO(OH) [(C_6H_2(OH)_2-(CO_2)_2].X.nH_2O$ (X=F, Cl, OH)

354 mg of $Fe(ClO_4)_3.xH_2O$ (1 mmol, Aldrich, 99%) and 297 mg (1.5 mmol) of 1,4-dihydroxyterephthalic acid (prepared according to synthesis C described in Example 1) are dispersed in 5 ml of DMF (Fluka, 98%) with 0.2 ml of 5M HF (SDS, 50%) and 1 ml of 5M $HClO_4$ (Aldrich, 70%). The mixture is left in a 23 ml Teflon body placed in a Paar metallic bomb for 3 days at 150° C. The solid is recovered by filtration and then calcined at 150° C. for 15 hours to remove the acid remaining in the pores.

TABLE 5

Elemental analysis (CNRS, Vernaison)

| Element | mass % | |
|---|---|---|
| | % iron | % carbon |
| MIL-88B 2OH | 15.4 | 36.5 |

The particle size measured by light scattering is >1 micron.

r) MIL-53-$NH_2$(Fe) or $FeO(OH) [(C_6H_2-NH_2-(CO_2)_2].X.nH_2O$ (X=F, Cl, OH)

270 mg of $FeCl_3.6H_2O$ (1 mmol, Alfa Aesar, 98%) and 180 mg (1 mmol) of 1,4-aminoterephthalic acid (Fluka, 98%) are dispersed in 10 ml of water. The mixture is left in a 23 ml Teflon body placed in a Paar metallic bomb for 3 days at 150° C. The solid is recovered by filtration.

To remove the free acid in the pores, 200 mg of the solid are suspended in 15 ml of absolute ethanol in a 23 ml Teflon body placed in a Paar metallic bomb for 2 days. The solid is recovered by filtration and washed a second time. Finally, the solid is recovered by filtration and dried at 150° C.

The particle size measured by light scattering shows two populations (PDI=0.296), a major population at 172 nm and another minor one at 728 nm.

s) MIL-53-Cl (Fe) or $FeO(OH) [C_6H_2Cl-(CO_2)_2].X.nH_2O$ (X=F, Cl, OH)

354 mg of $Fe(Cl_4)_3.xH_2O$ (1 mmol, Aldrich, 99%) and 200 mg (1 mmol) of 1,4-chloroterephthalic acid (prepared according to the synthesis described in Example 1) are dispersed in 5 ml of DMF. The mixture is left in a 23 ml Teflon body placed in a Paar metallic bomb for 2 days at 150° C. with a heating ramp of 12 hours. The solid is recovered by filtration and then calcined at 150° C. for 3 days.

The particle size measured by light scattering is greater than 1 micron.

t) MIL-53-Br(Fe) or $FeO(OH) [C_6H_2Br-(CO_2)_2].X.nH_2O$ (X=F, Cl, OH)

270 mg of $FeCl_3.6H_2O$ (1 mmol, Alfa Aesar, 98%) and 250 mg (1 mmol) of 1,4-bromoterephthalic acid (Fluka, 95%) are dispersed in 10 ml of DMF (Fluka, 98%) with 0.4 ml of 5M HF (SDS, 50%). The mixture is left in a 23 ml Teflon body placed in a Paar metallic bomb for 12 hours at 150° C. The solid is recovered by filtration and then calcined at 150° C. under vacuum for 15 hours to remove the acid remaining in the pores.

The particle size measured by light scattering is 196 nm, with the very minor presence of particles >1 micron.

u) MIL-53-$2CF_3$ (Fe) or $FeO(OH) [(C_6H_2(CF_3)_2-(CO_2)_2].X.nH_2O$ (X=F, Cl, OH)

135 mg of $FeCl_3.6H_2O$ (0.5 mmol, Alfa Aesar, 98%) and 151 mg (0.5 mmol) of 2,5-diperfluoro-1,4-terephthalic acid (synthesized according to synthesis B described in Example 1) are dispersed in 5 ml of water. The whole is left in a 23 ml Teflon body placed in a Paar metallic bomb for 16 hours at 100° C. The solid is recovered by filtration.

The particle size measured by light scattering is >1 micron.

v) MIL-53-$CH_3$ (Fe) or $FeO(OH) [C_6H_3-CH_3-(CO_2)_2].X.nH_2O$ (X=F, Cl, OH)

177 mg (0.5 mmol, Aldrich, 99%) of iron perchlorate and 90 mg (0.5 mmol) of 2-methylterephthalic acid (prepared according to synthesis C described in Example 1) and 0.05 ml of HF (5M) (0.25 mmol) are introduced into 2.5 ml of DMF (Fluka, 98%). The whole is left in a 23 ml Teflon body placed in a Paar metallic bomb for 16 hours at 150° C. The solid is recovered by filtration and calcined at 200° C. for 72 hours to remove the DMF remaining in the pores.

The particle size measured by light scattering is >1 micron.

w) MIL-53-2COOH(Fe) or $FeO(OH) [C_6H_3-(CO_2)_4].X.nH_2O$ (X=F, Cl, OH)

354 mg (1 mmol, Aldrich, 99%) of iron perchlorate and 254 mg (1 mmol) of 1,2,4,5-benzenetetracarboxylic acid (Aldrich, 99%) are introduced into 5 ml of distilled water. The whole is left in a 23 ml Teflon body placed in a Paar metallic bomb for 16 hours at 150° C. The solid is recovered by filtration.

To remove the acid remaining in the pores, 200 mg of solid are suspended in 100 ml of distilled water overnight. The solid is recovered by filtration.

The particle size measured by light scattering is >1 micron.

Example 4: Synthesis of MOF Materials Based on Fluoro Ligands a) MIL-53 (HF)

The solid MIL-53(HF) was obtained in its nanoparticle form from $FeCl_3.6H_2O$ (1 mmol; Alfa Aesar, 98%) and terephthalic acid (1 mmol; 1,4-BDC; Aldrich, 98%) in 5 ml of dimethylformamide (DMF; Fluka, 98%) with 0.1 ml of 5M hydrofluoric acid (Prolabo, 50%), the whole placed in an autoclave of "Paar bomb" type at 150° C. for 15 hours. The solid is recovered by centrifugation at 5000 rpm for 10 minutes.

200 mg of the solid are then suspended in 100 ml of distilled water with stirring for 15 hours to remove the residual solvent. The solid is then recovered by centrifugation at 5000 rpm for 10 minutes.

The particle size is finally measured by light scattering, and is 625 nm.

b) MIL-100(HF)

The solid MIL-100(HF) was obtained from $FeCl_3.6H_2O$ (1 mmol; Alfa Aesar, 98%) and ethyl trimesate (0.66 mmol; 1,3,5-BTC; Aldrich, 98%) in 5 ml of water and 0.1 ml of 5M hydrofluoric acid (Prolabo, 50%), and the whole is placed in an autoclave of "Paar bomb" type at 130° C. for 15 hours. The solid is recovered by centrifugation at 5000 rpm for 10 minutes.

200 mg of the solid are then suspended in 100 ml of refluxing distilled water with stirring for 3 hours to remove the residual acid. The solid is then recovered by centrifugation at 5000 rpm for 10 minutes.

The particle size is finally measured by light scattering, and is 1260 nm.

c) MIL-88Bx4F

The solid MIL-88Bx4F was obtained from $FeCl_3.6H_2O$ (1 mmol; Alfa Aesar, 98%) and tetrafluoroterephthalic acid (1 mmol; 4xF-BDC; Aldrich, 98%) in 10 ml of water, the whole placed in an autoclave of "Paar bomb" type at 85° C. for 15 hours. The solid is recovered by centrifugation at 5000 rpm for 10 minutes.

200 mg of the solid are finally suspended in 100 ml of distilled water with stirring for 2 hours to remove the residual acid. The solid is then recovered by centrifugation at 5000 rpm for 10 minutes.

The particle size was measured by light scattering, and is 850 nm.

Reference may be made, for example, to the syntheses described in Example 3 (Example 3c: MIL101-2CF3, Example 3F=MIL88B-4F, Example 3L-MIL88B-2CF3, Example 3u=MIL53-2CF3) and in Example 7 (Example 7d=MIL88B-2CF3, Example 7f=MIL53-2CF3).

The hybrid solids may also be synthesized via these processes and using the F18 radioisotope for PET (positron emission tomography) imaging.

These syntheses are based on ligands modified with perfluoro groups. For the modification with 18F, the ion-exchange method with 18F will preferably be used, given:

the short average half-life of 18F,
the difficulty in synthesizing fluoro ligands based on 18F,
that the PET imaging does not require much fluorine, and so the amount attached as counterion will be sufficient.

d) MOF Materials with Fluorine-18

MOFs comprising fluoride ions as counteranions may also serve in imaging.

For example, for PET (positron emission tomography) imaging, fluorine-18 is definitely the radioisotope of choice on account of its favorable radiophysical characteristics. The PET technique makes it possible to obtain very detailed images of living tissue. The fluorine-18 radioisotope (t1/2=110 minutes) is a positron emitter; the emitted positrons are immediately annihilated by the electrons of the surrounding material, and it is the resulting gamma rays that are detected.

Fluorine-18 is produced in a synchrotron line. Thus, for the synthesis of porous hybrid materials with the F18 radioisotope, the installation must be placed close to a synchrotron line since its average lifetime is very short (110 minutes).

There are two possible methods for obtaining porous hybrid solids with F18:

Method 1:

The hybrid solids are obtained in the presence of HF (F18) or of F18 fluoro ligands via the microwave route to reduce the synthesis time to a few minutes (3-30 min). The nanoparticles are recovered by centrifugation at 10 000 rpm for 5 minutes.

To obain a small particle of porous hybrid solids, it is preferable to use very short synthesis times, via the hydrosolvothermal route. Thus, a few iron carboxylates may also be synthesized via the solvothermal route when the synthesis time does not exceed 30 minutes.

Method 2:

0.1 mmol of porous hybrid solid nanoparticles already synthesized via the solvothermal route or the microwave route and activated are suspended in 1 ml of a 0.01 and 0.001 M solution of HF (F18) to perform the exchange of the OH anion with fluorine, with stirring for 15 minutes. The fluoro solid is recovered by centrifugation at 10 000 rpm for 5 minutes.

Example 5: Synthesis of MOF Materials Based on Bioactive Ligands

The use of ligands with biological activity is of interest for:

the release of an active compound by degradation of the MOF material,
the encapsulation of other active molecules for combined therapies.

Tests of antimicrobial activity, and also degradation in physiological media and the activity on cells, will be performed on porous iron carboxylates of flexible structure of the MIL-88 type using 4,4'-azobenzenedicarboxylic acid and 3,3'-dichloro-4,4'-azobenzenedicarboxylic acid, inter alia.

In the syntheses that follow, various bioactive molecules are used to prepare the MOF materials of the present invention, and especially: azobenzene, azelaic acid and nicotinic acid.

Azobenzene (AzBz), of formula $C_6H_5$—N=N—$C_6H_5$, may be incorporated into polymer matrices as stabilizer. Furthermore, the rigid structure of azo molecules allows them to behave as liquid-crystal mesogens in many materials. Moreover, azobenzene may be photoisomerized (cis or trans isomer), resulting in its use for photo-modulating the affinity of a ligand (for example a medicament) for a protein. Specifically, azobenzene may act as a photoswitch between a ligand and a protein by allowing or preventing protein-medicament binding according to the cis or trans isomer of azobenzene (one end of the azobenzene may be substituted, for example, with a group that binds to the target protein, whereas the other end is connected to a ligand (medicament) for the protein).

Azelaic acid ($HO_2C$—$(CH_2)_7$—$CO_2H$) is a saturated dicarboxylic acid with antibacterial, keratolytic and comedolytic properties. It is used especially in the treatment of acne and rosacea.

Nicotinic acid ($C_5H_4N$—$CO_2H$) is one of the two forms of vitamin B3, with nicotinamide. Vitamin B3 is especially necessary for the metabolism of carbohydrates, fats and proteins.

e) MIL-88G(AzBz) (Fe) or $Fe_3O[C_{12}H_8N_2$—$(CO_2)_2]_3.X.nH_2O$ (X=F, Cl, OH)

118 mg of $Fe(ClO_4)_3.xH_2O$ (0.33 mmol, Aldrich, 99%) and 90 mg (0.33 mmol) of 4,4'-azobenzenedicarboxylic acid (synthesized according to the method described by Ameerunisha et al., *J. Chem. Soc. Perkin Trans.* 2, 1679, 1995) are dispersed in 15 ml of DMF (Fluka, 98%). The whole is left in a 23 ml Teflon body placed in a Paar metallic bomb for 3 days at 150° C. The solid is recovered by filtration.

200 mg of the solid are suspended in 10 ml of DMF with stirring at room temperature for 2 hours to exchange the acid remaining in the pores. The solid is then recovered by filtration and then calcined at 150° C. under vacuum for 15 hours to remove the DMF remaining in the pores.

The particle size measured by light scattering is >1 micron.

f) MIL-88G-2Cl (AzBz-2Cl)(Fe) or $Fe_3O[C_{12}H_6N_2Cl_2$—$(CO_2)_2]_3.X.nH_2O$ (X=F, Cl, OH)

177 mg of $Fe(ClO_4)_3.xH_2O$ (0.5 mmol, Aldrich, 99%) and 169 mg (0.5 mmol) of dichloro-4,4'-azobenzenedicarboxylic acid (prepared according to synthesis F described in Example 1) are dispersed in 15 ml of DMF (Fluka, 98%). The whole is left in a 23 ml Teflon body placed in a Paar metallic bomb for 12 hours at 150° C. The solid is recovered by filtration.

200 mg of the solid are suspended in 10 ml of DMF with stirring at room temperature for 2 hours to exchange the acid remaining in the pores. The solid is then recovered by filtration and then calcined at 150° C. under vacuum for 15 hours to remove the DMF remaining in the pores.

The particle size measured by light scattering is >1 micron.

g) Iron azobenzene-3,3',5,5'-tetracarboxylate 1

118 mg of $Fe(ClO_4)_3.xH_2O$ (0.3 mmol, Aldrich, 99%) and 119 mg (0.3 mmol) of 3,3',5,5'-azobenzenetetracarboxylic acid (prepared according to synthesis G described in Example 1) are dispersed in 15 ml of DMF (Fluka, 98%) with 0.1 ml of 5M HF (SDS, 50%). The whole is left in a 23 ml Teflon body placed in a Paar metallic bomb for 3 days at 150° C. The solid is recovered by filtration and washed with acetone.

The solid obtained has a rigid cubic structure.

The particle size measured by light scattering is >1 micron.

h) Iron azobenzene-3,3',5,5'-tetracarboxylate 2

118 mg of $Fe(ClO_4)_3.xH_2O$ (0.3 mmol, Aldrich, 99%) and 119 mg (0.3 mmol) of 3,3',5,5'-azobenzenetetracarboxylic acid (prepared according to synthesis G described in Example 1) are dispersed in 15 ml of distilled water with 0.1 ml of 5M HF (SDS, 50%). The whole is left in a 23 ml Teflon body placed in a Paar metallic bomb for 3 days at 150° C. The solid is recovered by filtration and washed with acetone.

The particle size measured by light scattering is 498 nm, with a second minor population of 1100 nm.

i) Iron Azelate 1

270 mg of $FeCl_3.6H_2O$ (1 mmol, Aldrich, 99%) and 188 mg (1 mmol) of azelaic acid (Aldrich, 99%) are dispersed in 5 ml of distilled water. The whole is left in a 23 ml Teflon body placed in a Paar metallic bomb for 3 days at 100° C. The solid is recovered by filtration and washed with acetone.

200 mg of solid are suspended in 50 ml of absolute ethanol with stirring for 5 hours to activate it. The solid is recovered by filtration.

The particle size measured by light scattering is >1 micron (1500 nm).

j) Iron Nicotinate 1

The synthetic conditions in water are as follows:

135 mg of $FeCl_3.6H_2O$ (1 mmol, Aldrich, 99%) and 62 mg (1 mmol) of nicotinic acid (Aldrich, 99%) are dispersed in 5 ml of distilled water with 0.1 ml of 2M NaOH. The whole is left in a 23 ml Teflon body placed in a Paar metallic bomb for 16 hours at 100° C. The solid is recovered by filtration and washed with acetone.

The synthetic conditions in DMF are as follows:

135 mg of $FeCl_3.6H_2O$ (1 mmol, Aldrich, 99%) and 62 mg (1 mmol) of nicotinic acid (Aldrich, 99%) are dispersed in 5 ml of DMF (Fluka, 98%). The whole is left in a 23 ml Teflon body placed in a Paar metallic bomb for 16 hours at 100° C. The solid is recovered by filtration and washed with acetone.

The monodisperse particle size (PDI=0.241) measured by light scattering is 662 nm.

III. Modulable Process for Preparing Nanoparticles

Example 6: Control of the Particle Size, Influence of the Various Parameters

In this example, control of the particle size may be obtained by changing one or more of the following parameters during the synthesis:
the synthesis time
the pH
the addition of an additive (monoacid of acetic acid, etc. type)
the stirring the nature of the solvent
microwave synthesis
ultrasonication synthesis.

After the synthesis, the nanoparticles are washed with solvents, recovered by centrifugation and dried under vacuum, in air or under a controlled atmosphere, optionally with heating.

The nanoparticles are then analyzed by a combination of techniques that make it possible to determine the structures and composition of the phases: X-rays, IR spectroscopy, X-ray thermodiffraction, thermogravimetric analysis, elemental analysis, electron microscopy, measurement of the zeta potential and measurement of the particle size.

The X-ray powder diagrams are collected on a conventional high-resolution X-ray diffractometer (θ-2θ) D5000 Siemens X'Pert MDP ($\lambda_{Cu}$, K$\alpha_1$, K$\alpha_2$) typically between 5 and 30° (2θ) using an interval of 0.02° and a counting time of 4 seconds in continuous mode.

The X-ray thermodiffractometry is performed in a Siemens D-5000 X-ray diffractometer in θ-θ mode in air.

The specific surface area measurements are obtained with a Micromeritics ASAP 2010 adsorption machine using $N_2$ as gas (porosity calculation of BJH type).

The IR spectra are acquired with a Nicolet-Magma IR550 spectrometer.

The thermogravimetric analyses are performed with a machine of TA 2050 brand between 25 and 600° C., with a heating rate of 2° C. min$^{-1}$.

The particle size and zeta potential measurements are taken with a Malvern Zetasizer Nano series—Nano-ZS machine; Zen 3600 model; serial No. 500180; UK.

The scanning electron microscopy was performed with an ultra-high resolution 200 kV Topcon EM 002B machine (Akashi).

a) Influence of the Synthesis Time, Application to the Synthesis of MIL-53(Fe) Nanoparticles A mixture of a solution of $FeCl_3.6H_2O$ (1 mmol; Alfa Aesar, 98%), terephthalic acid (1 mmol; 1,4-BDC; Aldrich, 98%) in 5 ml of dimethylformamide (DMF; Fluka, 98%) is placed in a Teflon insert placed in an autoclave at a temperature of 150° C. for 72 hours with a heating ramp of 12 hours and cooling for 24 hours to room temperature. After the reaction, the precipitate is filtered off and washed with deionized water. The solid MIL-53(Fe) is obtained in the form of crystals several hundred microns in size.

Decreasing the synthesis time (without a heating ramp or cooling) leads to smaller particle sizes (Table 6), with, for example, a size of 335 nm for a 4-hour synthesis at 150° C. Next, to remove the solvent from the pores of the solid, typically 200 mg of solid are dispersed in 100 ml of deionized water overnight with stirring, followed by filtration or centrifugation (depending on the particle size).

Table 6 below collates the sizes of the nanoparticles obtained. It shows that short synthesis times promote the presence of small particles.

TABLE 6

Size of MIL-53(Fe) particles as a function of the synthesis time

| Synthesis time (in hours) | Particle diameter Dp (in nm) |
|---|---|
| 24 | 6220 |
| 12 | 2460 |

TABLE 6-continued

Size of MIL-53(Fe) particles as a function of the synthesis time

| Synthesis time (in hours) | Particle diameter Dp (in nm) |
|---|---|
| 6 | 720 |
| 5 | 800 |
| 4 | 335 |
| 2 | 380 | b) Influence of the pH, Application to the Synthesis of MIL-89(Fe) Nanoparticles Iron(III) acetate (1 mmol; synthesized according to synthesis A described above) is mixed with stirring with muconic acid (1 mmol; Fluka, 97%) in methanol medium (5 ml; Aldrich, 99.9%) or ethanol medium (5 ml; Riedel-de Haën, 99.8%). The whole is maintained without stirring at 100° C. for 12 hours in the presence of 0.25 ml of aqueous sodium hydroxide solution at 2 mol/l (Alfa Aesar, 98%) to give smaller particle sizes.

Table 7 below collates the sizes of the nanoparticles obtained as a function of the addition or otherwise of base, and shows that the addition of base promotes the presence of small particles.

TABLE 7

Size of MIL-89(Fe) particles as a function of the addition of base

| Solvent | Volume of aqueous 2M NaOH solution added (ml) | Dp (nm) |
|---|---|---|
| methanol | 0 | 585 |
| methanol | 0.25 | 471 |
| ethanol | 0 | 493 |
| ethanol | 0.25 | 398 |

Thus, an increase in pH brings about easier deprotonation of the carboxylic ligand, which accelerates the reaction rate.

c) Influence of the Addition of an Additive, Application to the Synthesis of MIL-88A(Fe) Nanoparticles MIL-88A iron fumarate is obtained from 270 mg of $FeCl_3.6H_2O$ (1 mmol; Alfa Aesar, 98%), 112 mg of fumaric acid (1 mmol; Acros, 99%) introduced into 15 ml of ethanol (Riedel de Haën, 99.8%) and variable amounts of acetic acid (Aldrich, 99.7%) are added. The solution is then heated for 2 or 4 hours at 65° C.

TABLE 8

Sizes of the MIL-88A(Fe) particles obtained in the presence of variable amounts of acetic acid at two different synthesis times (2 or 4 hours)

| Volume of acetic acid introduced (ml) | Dp (nm) t = 2 h | Dp (nm) t = 4 h |
|---|---|---|
| 0 | 417 | 532 |
| 0.25 | 381 | 592 |
| 0.5 | 433 | 587 |
| 1 | 256 | 301 |

These results clearly show that the addition of a monocarboxylic acid slows down the crystal growth and thus makes it possible to obtain nanoparticles of smaller size. Acetic acid may be added at any point in the reaction.

d) Influence of Stirring

The influence of stirring was studied during the synthesis of the compound MIL-88A.

The method used to prepare the nanoparticles of the compound MIL-88A consists in introducing 1 mmol of iron(III) chloride hexahydrate (270 mg) and 1 mmol of fumaric acid (112 mg) into 4.8 ml of DMF, and adding 0.4 ml of 2M NaOH solution. The whole is heated at 150° C. for 2 hours, with or without stirring.

Figure 11:
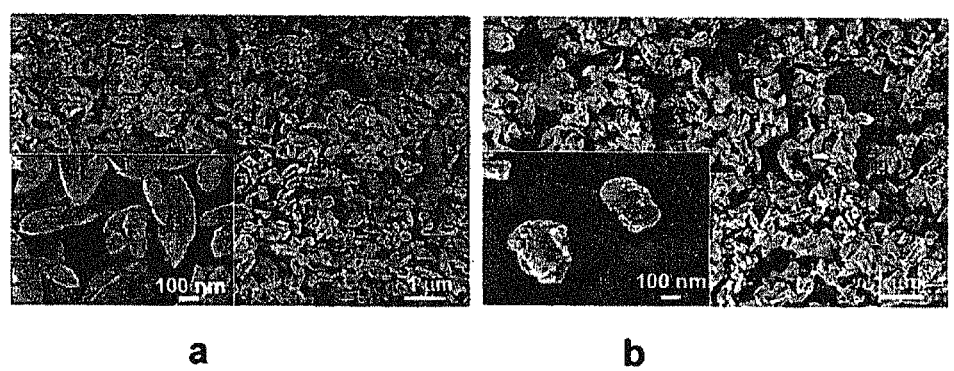
FIG. 11 represents the SEM images of the material MIL-88A synthesized according to example 6, without stirring (FIG. 11a) or with stirring (FIG. 11b).

Electron microscopy shows that particles obtained in the absence of stirring have a different morphology from those obtained with stirring, as shown by FIG. 11. Stirring thus brings about a reduction in particle size, but also changes the morphology, which might have an effect on the toxicity of the solids.

e) Influence of the Solvent, Application to the Synthesis of MIL-88A(Fe) Nanoparticles The synthesis of the solid MIL-88A was performed, on the one hand, in water, and, on the other hand, in methanol. A mixture containing iron chloride (1 mmol), fumaric acid (1 mmol) in 15 ml of solvent (methanol or deionized water) is placed in contact with variable amounts of acetic acid, used as cosolvent, without stirring at 65° C. for 2 or 4 hours. The particle sizes obtained are listed in Table 9.

TABLE 9

Sizes of the MIL-88A(Fe) particles as a function of the solvent, of the amount of acetic acid for two synthesis times

| Solvent | Volume of acetic acid introduced (ml) | Dp (nm) t = 2 h | Dp (nm) t = 4 h |
|---|---|---|---|
| methanol | 0 | 417 | 532 |
| methanol | 0.25 | 381 | 592 |
| methanol | 0.5 | 433 | 587 |
| methanol | 1 | 256 | 301 |
| water | 0 | 328 | 451 |
| water | 0.25 | 265 | 364 |
| water | 0.5 | 336 | 535 |
| water | 1 | 198 | 238 |

The MIL-88A particles obtained in water are smaller than those obtained in methanol. Thus, the nature of the solvent used during the synthesis has a strong influence on the particle size.

Example 6B

Control of the Size of MIL-88A Particles, Influence of 4 Parameters: Temperature, Reaction Time, Concentration of Reagents and Addition of a Monocarboxyl Compound a) Synthesis of Iron Fumarate without Monocarboxyl Additive 5 ml of an aqueous solution of iron fumarate hexahydrate ($FeCl_3.6H_2O$, 1 mmol; Alfa Aesar, 98%) and of fumaric acid (1 mmol; Acros, 99%) are placed in a 23 ml Teflon body placed in a Paar metallic bomb. The whole is placed in an autoclave at a temperature of 65, 100 or 150° C., for times ranging from 30 minutes to 3 days. Next, the precipitate obtained is recovered by centrifugation at 5000 rpm for 10 minutes. It is dried at 100° C. in an oven and weighed to determine the synthetic yield. The particle diameter is determined by quasi-elastic light scattering. The X-ray diffractograms are obtained as described previously.

We sought to find optimum operating conditions (temperature, reaction times) for simultaneously obtaining: i) good crystallization (+++); ii) a diameter of less than 1000 nm (nanoparticles); iii) a satisfactory yield (>25 wt %) and iv) the absence of iron oxides.

The table below collates the results obtained during the various syntheses. The yields are considered unsatisfactory when they are less than 25 wt %. The absence of crystallization is indicated by –, good crystallization by +++, and insufficient crystallization by + or ++.

| Temperature | Time (h) | Diameter (nm) | Crystallinity | Yield (mass %) |
|---|---|---|---|---|
| 65° C. | 2 | 300-400 | – | <1% |
|  | 6 | 300-600 | ++ | <5% |
|  | 16 | 300-600 | +++ | >25% |
|  | 72 | 300-600 | +++ | >50% |
| 100° C. | 0.5 | 400-500 | + | <10% |
|  | 2 | 500-600 | + | <10% |
|  | 6 | 500-800 | +++ | >50% |
|  | 16 | 600-1000 | +++ | >75% |
|  | 72 | 600-2000 | +++ | >75% |
| 150° C. | 0.5 | 500-700 | – | <10% |
|  | 2 | 400-500* | + | <10% |
|  | 6 | 600-1000* | +++ | >50% |
|  | 16 | 800-2000* | +++ | >75% |
|  | 72 | 800-2000* | +++ | >75% |

*Presence of iron oxides

At 65° C., the reaction should be continued for at least 16 hours to obtain conditions i-iv, whereas at 100° C., 6 hours of reaction are sufficient, but the diameters are larger (500-800 nm). At 150° C., it was impossible to combine all the necessary conditions i to iv, since, within 2 hours of reaction, there is formation of iron oxides to the detriment of the formation of a crystal framework.

The best results were obtained at 65° C., with a reaction time of 16 hours, allowing the production of the finest particles (300-600 nm).

b) Synthesis of Iron Fumarate (MIL 88A) by Ultrasonication

MIL-88A nanoparticles were synthesized in water, via ultrasonication at 0° C. by modifying the reaction time (between 30 and 120 minutes) using fumaric acid ($C_4H_4O_4$, Acros, 99%) and iron(III) chloride hexahydrate ($FeCl_3.6H_2O$, Acros, 97%).

The two solid reagents are weighed out separately on a precision balance, and the solvent (water) is then added for each of the solids: 5.4 g of $FeCl_3$+distilled water in a 200 ml flask and 2.32 g of fumaric acid+distilled water in a 200 ml flask.

Two solutions of concentrations 27 mg/ml and 11.6 mg/ml of iron(III) chloride and of fumaric acid, respectively, are thus obtained. The fumaric acid solution is brought to 70° C. with stirring for about 120 minutes to dissolve the product. The iron chloride is added using a magnetic stirrer for 30 minutes.

5 ml of each solution are mixed in 20 ml glass flasks (vials). The vials are placed at the same time in a sonication bath at 0° C. (Labo-moderne TK 52H serial No.: 164046192 Sonoclean) for times of 30 to 120 minutes.

The size of the particles obtained (measured by light scattering (Nanosizer)) exceeded one micron, irrespective of the sonication time.

A second test was performed, this time adding 30 µl of acetic acid 15 minutes before the end of the synthesis (corresponding to removal from the sonication bath). The particle diameter was about 500 nm after 30 minutes of synthesis, 800 nm after 60 minutes, and then exceeded one micron after 90 minutes of synthesis.

The addition of acetic acid (a monoacid) causes stoppage of the crystal growth, since it coordinates the iron; the iron cannot bind to another iron atom (because of the $2^{nd}$ COOH). In this way, acetic acid allows the production of smaller nanoparticles.

With the aim of obtaining even finer particles, a third test was performed, reducing the concentration of the fumaric acid and iron chloride solutions, the other conditions being the same.

By reducing the concentrations by a factor of 2, in the absence of additives (acetic acid), the diameters remained greater than one micron. However, reducing the concentrations by a factor of ten made it possible to obtain nanoparticles of about 200 nm with a synthesis time of 30 minutes.

It should be noted that increasing the reaction temperature results in an increase in the size of the particles. For example, for a tenfold decrease in concentrations, in the absence of additives, the diameter increases from 200 nm to 240 nm when the synthesis takes place for 30 minutes, at 20° C. instead of 0° C. In all cases, an increase in synthesis time leads to an increase in particle size.

There are thus optimum operating conditions (concentrations, reaction temperature, reaction time, presence of additives) that make it possible to reduce the size of the particles. These particles may be smaller than one micron or even of the order of 200 nm (suitable for intravenous administration).

These optimum operating conditions may be determined empirically on all the MOF solids according to the present invention.

These optimum synthetic conditions (0° C., starting with very dilute solutions of reagents) were used for grafting PEG onto the surface of the nanoparticles.

C) Preparation of PEGylated MIL-88A Nanoparticles

Thus, PEGylated MIL-88A nanoparticles (surface-modified with PEG) were synthesized in water, via ultrasonication at 0° C., starting with fumaric acid ($C_4H_4O_4$, Acros, 99%) and iron(III) chloride hexahydrate ($FeCl_3.6H_2O$, Acros, 97%).

The two solid reagents are weighed out separately on a precision balance and the solvent (water) is then added for each of the solids: 0.54 g of $FeCl_3$+distilled water into a 200 ml flask and 0.232 g of fumaric acid+distilled water into a 200 ml flask. Two solutions at concentrations of 2.7 mg/ml and 1.16 mg/ml of iron(III) chloride and of fumaric acid, respectively, are thus obtained. The fumaric acid solution is maintained at 70° C. with stirring for about 120 minutes to dissolve the product. The iron chloride is stirred using a magnetic stirrer for 30 minutes.

5 ml of each solution are mixed in 20 ml glass flasks (vials). The vials are placed at the same time in a sonication bath (Labo-moderne TK 52H serial No.: 164046192 Sonoclean). After 30 minutes, 5 mg of monomethoxy poly (ethylene glycol) monoacid (MeO-PEG-COOH, Sigma, molar mass 5000 g/mol) are added. The reaction is left to continue under ultrasonication for a further 90 minutes.

The diameter of the nanoparticles (measured by light scattering) was 230 nm and the manufacturing yield was 50% (by weight). In this example, the addition of the monoacid MeO-PEG-COOH also results in stoppage of the crystal growth, since it coordinates the iron; the iron cannot bind to another iron atom (because of the $2^{nd}$ COOH). In this way, MeO-PEG-COOH allows the production of smaller nanoparticles.

Example 7: Process for Synthesizing MOF Materials via the Microwave Route

Figure 12:
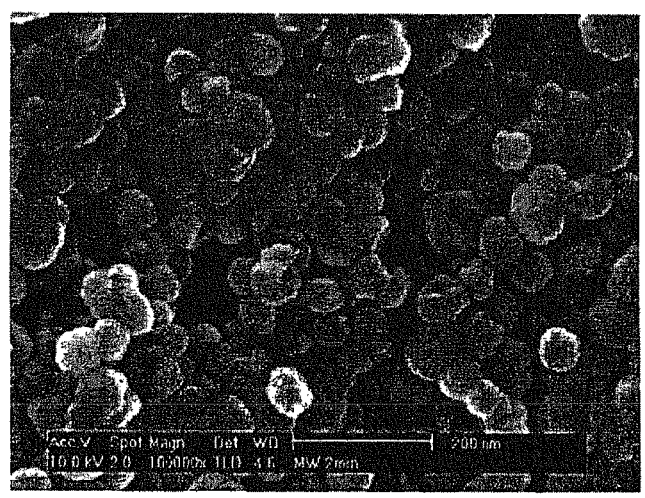
FIG. 12 represents the electron microscopy image of the solid MIL-101(Cr) obtained via synthesis (10 minutes at 220° C.)

Another possible route for synthesizing porous hybrid solid nanoparticles uses microwave energy. This makes it possible to control the nanoparticle size and to obtain monodisperse nanoparticles. Thus, recently, the inventors developed, in collaboration with a Korean group, the microwave synthesis of MIL-101(Cr) chromium carboxylate, as described in Sung Hwa Jhung, et al., *Adv. Mater* (2006), 19(1), 121-124 [32]. This synthesis allowed the production of nanoparticles between 40 and 90 nm in size over a very short synthesis time (1 to 60 minutes) (FIG. 12).

The synthetic method used is as follows: 400 mg of chromium nitrate hydrate (Aldrich, 99%), 166 mg of terephthalic acid (Alfa Aesar, 98%), 0.2 ml of HF solution at 5 mol/l in water, and 4.8 ml of deionized water are mixed together and introduced into a Teflon autoclave. The whole is placed in a microwave oven (Mars-5) and raised to 210° C. over 2 minutes and then maintained at this temperature for 1 to 60 minutes. The resulting mixture is then filtered a first time with a filter paper of porosity 100 µm to remove the recrystallized terephthalic acid. The acid remains on the filter paper and the MIL-101 solid passes through the filter. The filtrate is recovered and the MIL-101 solid is recovered by filtration on a 40 µm filter. In a second stage, a solvothermal treatment in 95% ethanol at 100° C. for 20 hours. The final solid is cooled, filtered off and washed with deionized water and then dried at 150° C. in air.

a) MIL-100 (Fe) or $Fe_3O[C_6H_3—(CO_2)_3]_2.X.nH_2O$ (X=F, Cl, OH)

The conditions of the microwave synthesis without fluorine are as follows:

9.7 g of $Fe(NO_3)_3.9H_2O$ (24 mmol, Aldrich, 98%), 3.38 mg (16 mmol) of 1,3,5-benzenetricarboxylic acid (1,3,5-BTC; Aldrich, 99%) are dispersed in 40 ml of distilled water. The whole is left in a Teflon body at 180° C. for 30 minutes (power 600 W). The solid is recovered by centrifugation at 10 000 rpm for 10 minutes.

200 mg of the solid are suspended in 100 ml of distilled water at reflux with stirring for 3 hours to remove the acid remaining in the pores. The solid is then recovered by centrifugation at 10 000 rpm for 10 minutes.

The monodisperse particle size measured by light scattering is 400 nm.

b) MIL-101 (Fe)—$NH_2$ or $Fe_3O[NH_2—C_6H_3—(CO_2)_2]_3.X.nH_2O$ (X=F, Cl, OH)

The microwave synthesis conditions are as follows:

135 mg (0.5 mmol) of $FeCl_3.6H_2O$ and 90 mg of amino-1,4-benzenedicarboxylic acid (0.5 mmol, $NH_2$-1,4-BDC, Aldrich, 99%) are dispersed in 25 ml of distilled water with 0.25 ml of 1M HCl (Aldrich, 35%; added dropwise). The whole is left in a Teflon body for 5 minutes at 60° C. with a heating ramp of 40 seconds (power 400 W). The dark brown solid is recovered by centrifugation at 10 000 rpm for 10 minutes. The compound is washed with absolute ethanol so as to remove the unconsumed acid, and then centrifuged again.

In order to avoid degradation, the compound is kept moist.

The monodisperse particle size (PDI=0.005) measured by light scattering is 271 nm.

Langmuir surface area=2042.7091 $m^2/g$.

c) MIL-88B-NH$_2$(Fe) or Fe$_3$O[NH$_2$—C$_6$H$_3$—(CO$_2$)$_2$]$_3$.X.nH$_2$O (X=F, Cl, OH)

The microwave synthesis conditions are as follows:

405 mg (1.5 mmol) of FeCl$_3$.6H$_2$O and 534 mg of amino-1,4-benzenedicarboxylic acid (3 mmol, NH$_2$-1,4-BDC, Aldrich, 99%) are dispersed in 25 ml of absolute ethanol (Aldrich). The whole is left in a Teflon body for 5 minutes at 100° C. with a heating ramp of 40 seconds (power 800 W). The dark brown solid is recovered by centrifugation at 10 000 rpm for 10 minutes. The compound is washed with absolute ethanol so as to remove the unconsumed acid, and then centrifuged again.

The monodisperse particle size (PDI=0.069) measured by light scattering is 106 nm.

d) MIL-88B-2CF$_3$(Fe) or Fe$_3$O[(CF$_3$)$_2$—C$_6$H$_2$—(CO$_2$)$_2$]$_3$.X.nH$_2$O (X=F, Cl, OH)

The microwave synthesis conditions are as follows:

675 mg (2.5 mmol) of FeCl$_3$.6H$_2$O, 755 mg of 2,5-bis(tri-fluoromethyl)terephthalic acid (2.5 mmol, synthesis B of Example 1) are dispersed in 25 ml of absolute ethanol (Aldrich). The mixture is left in a Teflon body for 5 minutes at 100° C. with a heating ramp of 30 seconds (power 400 W). The solid is recovered by centrifugation at 10 000 rpm for 10 minutes.

The solid is then calcined under vacuum at 200° C. for 15 hours.

The monodisperse particle size (PDI=0.209) measured by light scattering is 78 nm.

e) MIL-88B-NO$_2$(Fe) or Fe$_3$O[NO$_2$—C$_6$H$_3$—(CO$_2$)$_2$]$_3$.X.nH$_2$O (X=F, Cl, OH)

The microwave synthesis conditions are as follows:

1.35 mg (10 mmol) of FeCl$_3$.6H$_2$O and 1.055 mg of nitroterephthalic acid (10 mmol, Aldrich, 98%) are dispersed in 25 ml of distilled water. The whole is left in a Teflon body for 5 minutes at 100° C. with a heating ramp of 90 seconds (power 400 W). The solid is recovered by centrifugation at 10 000 rpm for 10 minutes.

The monodisperse particle size (PDI=0.005) measured by light scattering is 408 nm.

f) MIL-53-2CF$_3$(Fe) or FeO(OH)[C$_6$H$_2$—(CF$_3$)$_2$—(CO$_2$)$_2$].X.nH$_2$O (X=F, Cl, OH)

The microwave synthesis conditions are as follows:

675 mg (2.5 mmol) of FeCl$_3$.6H$_2$O and 755 mg of 2,5-bis(trifluoromethyl)terephthalic acid (2.5 mmol, synthesis B) are dispersed in 25 ml of distilled water. The whole is left in a Teflon body for 20 minutes at 100° C. with a heating ramp of 90 seconds (power 400 W). The pale yellow solid is recovered by centrifugation at 10 000 rpm for 10 minutes. The compound is then calcined under vacuum at 250° C. for 15 hours.

The particle size (PDI=0.245) measured by light scattering is 330 nm.

g) MIL-88A (Fe) or Fe$_3$O[(C$_4$H$_2$—(CO$_2$)$_2$]$_3$.X.nH$_2$O (X=F, Cl, OH)

The microwave synthesis conditions are as follows:

270 mg (1 mmol) of FeCl$_3$.6H$_2$O, 116 mg of fumaric acid (1.0 mmol, Acros, 99%) are dispersed in 30 ml of distilled water. The whole is left in a Teflon body for 2 minutes at 100° C. with a heating ramp of 1 minute (power 1600 W).

The solid is recovered by centrifugation at 10 000 rpm for 10 minutes.

200 mg of the product are suspended in 100 ml of distilled water to exchange the remaining fumaric acid. The hydrated solid is recovered by centrifugation at 10 000 rpm for 10 minutes.

The monodisperse particle size measured by light scattering is 120 nm.

Example 8: Process for Synthesizing MOF Materials Via the Ultrasonication Route

The solid MIL-88A is synthesized via the ultrasonication route at 0° C. with several different reaction times (30, 60, 90 and 120 minutes).

The synthesis is performed starting with fumaric acid and iron(III) chloride hexahydrate in water. The two solid reagents are weighed out and dissolved separately in water in the proportions given in the table below. The fumaric acid solution is maintained at 70° C. with stirring for 120 minutes to dissolve the product. The iron chloride is stirred using a magnetic stirrer for 30 minutes.

TABLE 10

| Fumaric acid and iron(III) chloride solutions | | | |
| --- | --- | --- | --- |
| Reagent | Formula | Supplier | Amount |
| Iron(III) chloride | FeCl$_3$•6H$_2$O | Acros, 97% | 0.54 g in 200 ml of water (i.e. 2.7 mg/ml) |
| Fumaric acid | C$_4$H$_4$O$_4$ | Acros, 99% | 0.232 g in 200 ml of water (i.e. 1.16 mg/ml) |

5 ml of each of the above 2 solutions are added to a 20 ml flask. 8 flasks are prepared in total:
  4 flasks in which the reactions are performed for the 4 synthesis times: 30, 60, 90 and 120 minutes,
  4 flasks in which acetic acid (30 μl) is added 15 minutes before the end of each of the syntheses of duration 30, 60, 90 and 120 minutes (the end of the synthesis corresponding to removal from the ultrasonication bath). The addition of the monoacid (acetic acid) produces stoppage of the crystal growth, since it does not allow two iron atoms to be connected (in contrast with fumaric acid, which is a dicarboxylic acid). In this way, acetic acid allows the production of smaller nanoparticles and more stable suspensions of these particles (avoids the sedimentation of large particles and particle aggregation).

The 8 flasks are placed at the same time in a sonication bath at 0° C., for the corresponding times t (30, 60, 90 and 120 minutes).

After the synthesis, a volume of 0.1 ml of solution is removed from each flask in order to determine the particle size by light scattering using a Dynamic Light Scattering machine (DLS, Nanosizer). The rest of the solution is then centrifuged at 10 000 rpm at 0° C. for 15 minutes in order to separate the supernatant from the solid formed. The supernatant is removed using a Pasteur pipette and the recovered pellet is placed in a fume cupboard at room temperature.

Figure 28:
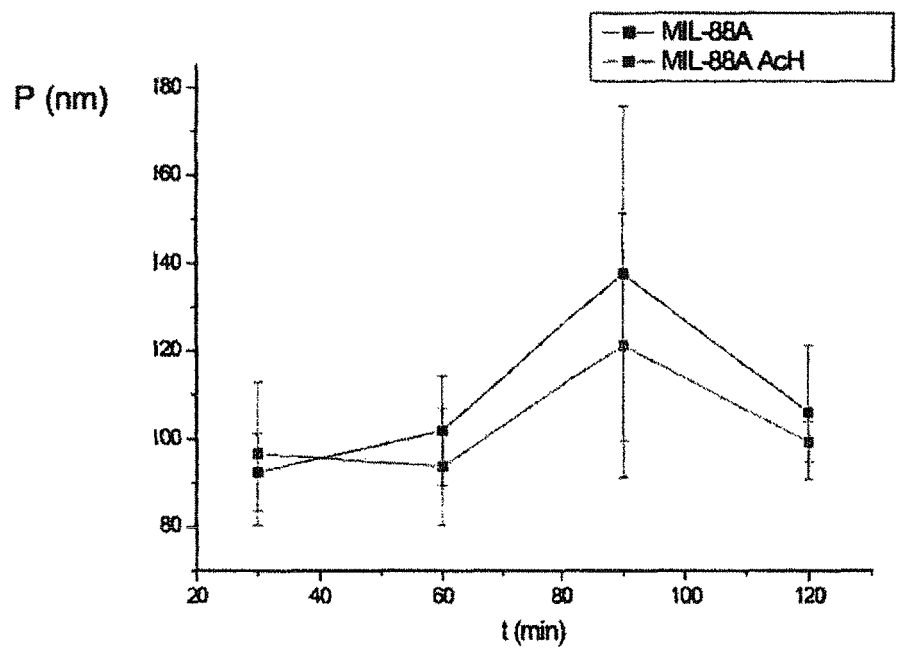
FIG. 28 represents the change in particle size (P in nm) as a function of the synthesis time (t in min) via the ultrasonication route (0° C. in the presence or absence of acetic acid) (example 8).

Apparatus used:
Sonication bath: Labo-moderne TK 52H serial No.: 164046192 Sonoclean
Centrifuge: Jouan MR 1812
Nanosizer: Coulter N4 Plus USA; Malvern The change in particle size (P in nm) as a function of time (t in minutes) is represented in FIG. 28. It is possible to observe a decrease in the particle size in the presence of fumaric acid.

The addition of acetic acid produces a reduction in crystallinity, which is more pronounced at shorter times. However, it is possible to distinguish characteristic reflections of the MIL-88A phase. These reflections are very broad as a consequence of the nanometric size of the crystallite.

At longer synthesis times, there is no significant difference in crystallinity between the synthesis without acetic acid and that performed in the presence of this monoacid.

IV. Characteristics and Properties of the Nanoparticles Obtained

Example 9: Analytical and Crystallographic Data for the Iron Carboxylates a) Phases MIL-53(Fe) or Fe(OH)[$O_2C$—$C_6H_4$—$CO_2$].$H_2O$ The synthetic conditions are as follows:

0.27 g (1 mmol) of $FeCl_3.6H_2O$ and 166 mg (1 mmol) of 1,4-benzenedicarboxylic acid (1,4-BDC) are dispersed in 5 ml of dimethylformamide (DMF), the whole left for 12 hours at 150° C. in a 23 ml Teflon body placed in a Paar metallic bomb. The solid is then filtered off and washed with acetone.

The mesh parameters of different forms of the flexible phase MIL-53(Fe) in its dry form (dry; empty pores), hydrated form ($H_2O$; water in the pores), crude synthetic product (crude; DMF in the pores) and containing busulfan (forms Bu1 and Bu2):

TABLE 11

Mesh parameters of different forms of the flexible phase MIL-53(Fe)

| Phase | a (Å) | b (Å) | c (Å) | Beta (°) | Volume (Å$^3$) | Space group |
|---|---|---|---|---|---|---|
| MIL-53dry | 21.312 | 6.633 | 6.871 | 115.22 | 878.77 | C2/c |
| MIL-53($H_2O$) | 21.12 | 7.66 | 6.83 | 114.87 | 1003.0 | C2/c |
| MIL-53crude | 19.07 | 11.29 | 6.87 | 108.92 | 1398.3 | C2/c |
| MIL-53Bu1 | 17.61 | 6.75 | 10.25 | 112.97 | 1122.2 | C2/m |
| MIL-53Bu2 | 18.10 | 9.46 | 7.17 | 119.70 | 1202.5 | C2/c |

Figure 18:
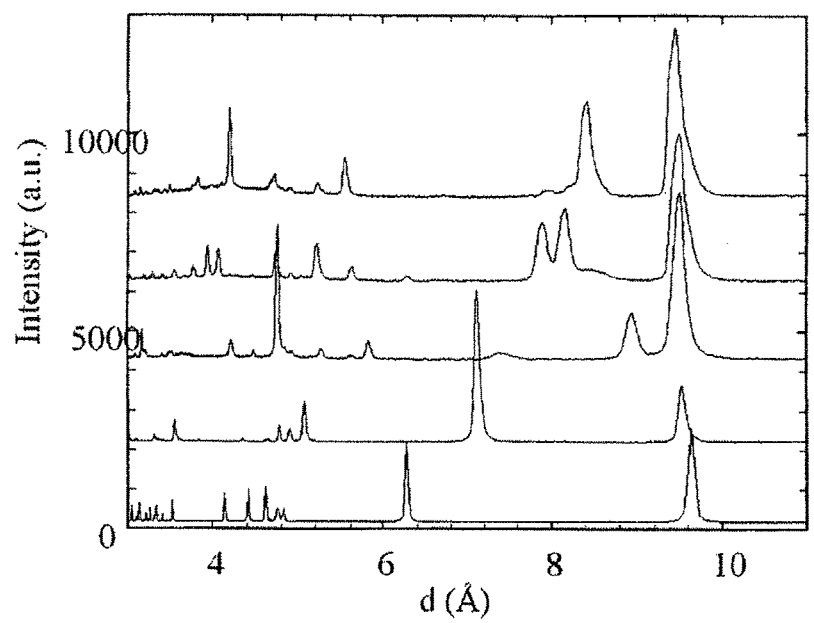
FIG. 18 represents the X-ray diffractograms of the various forms of the solid MIL-53 (from bottom to top: dry form, hydrated form, synthetic crude product, MIL-53Bu1 and MIL-53Bu2).
Figure 19:
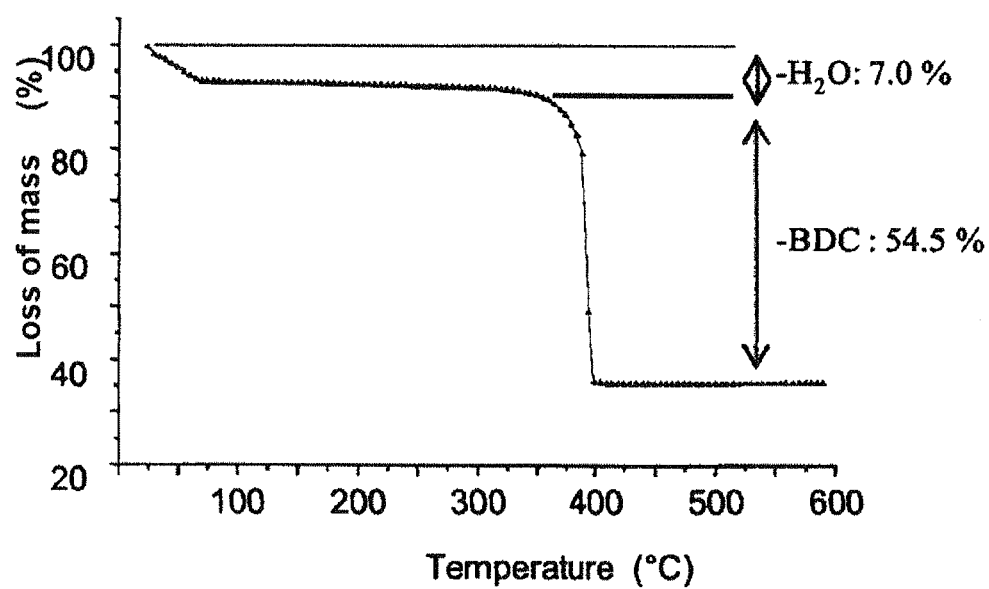
FIG. 19 represents the thermogravimetric analysis (in air) of the hydrated compound MIL-53(Fe) (heating rate of 5° C./minute).

FIG. 18 and FIG. 19 represent, respectively, the X-ray diffractograms of the various forms of solid MIL-53 and the thermogravimetric analysis of the hydrated compound MIL-53(Fe).

The solid iron MIL-53 does not have a specific surface area of greater than 20 m$^2$/g, since the pore structure is closed in the dry form (adsorption of nitrogen by vacuum)

TABLE 12

Elemental analysis

| Element/mass % | % iron | % carbon | % hydrogen |
|---|---|---|---|
| MIL-53(Fe) | 21.11 | 37.60 | 2.75 | b) Phase MIL-88A or $Fe_3O[O_2C$—$C_2H_2$—$CO_2]_3.X.nH_2O$ (X=F, Cl, OH)

The synthetic conditions are as follows:

0.27 g (1 mmol) of $FeCl_3.5H_2O$ and 116 mg (1 mmol) of fumaric acid are dispersed in 5 ml of water. The whole is left for 12 hours at 100° C. in a 23 ml Teflon body placed in a Paar metallic bomb. The solid is then filtered off and washed with acetone.

TABLE 13

Mesh parameters of the solid MIL-88A, dry and hydrated

| Phase | a (Å) | c (Å) | Volume (Å$^3$) | Space group |
|---|---|---|---|---|
| dry MIL-88A | 9.25 | 15.30 | 1135 | P-62c |
| hydrated MIL-88A | 13.9 | 12.66 | 2110 | P-62c |

Figure 20:
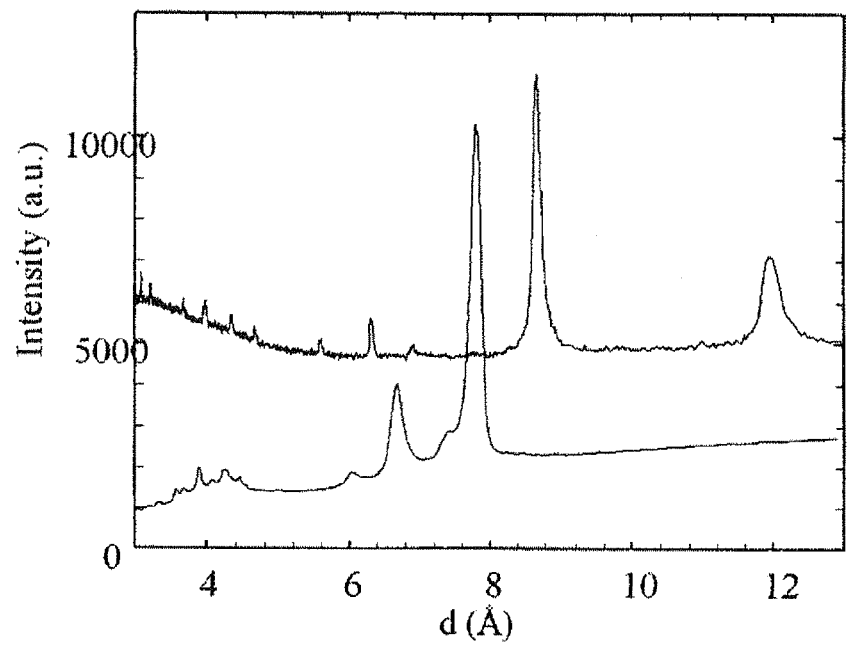
FIG. 20 represents the X-ray diffractograms of the solids MIL-88A dry (bottom) and hydrated (top).

FIG. 20 represents the X-ray diffractograms of the dry and hydrated solids MIL-88A.

Figure 21:
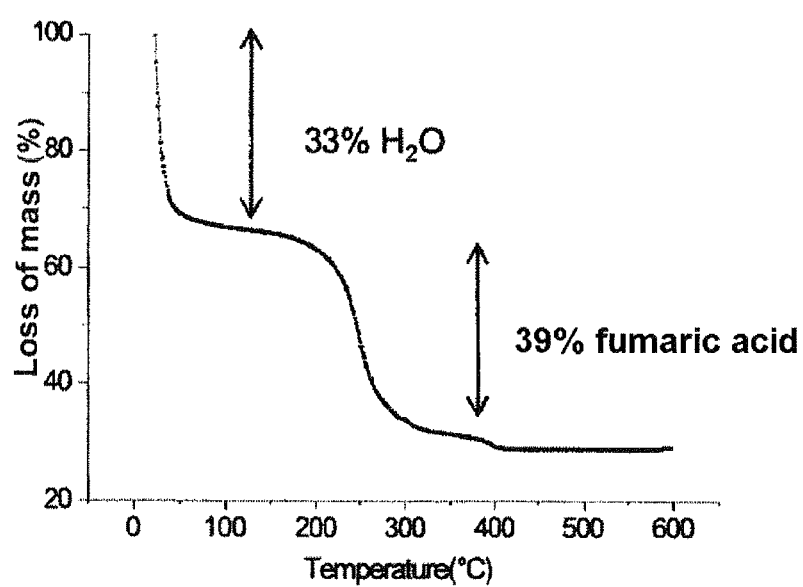
FIG. 21 represents the thermogravimetric analysis (in air) of the hydrated compound MIL-88A (heating rate of 5° C./minute).

FIG. 21 represents the thermogravimetric analysis of the hydrated compound MIL-88A.

This compound does not have a surface (greater than 20 m$^2$/g) that is accessible to nitrogen at 77 K, since the dry structure is not porous.

TABLE 14

Elemental analysis

| Element/mass % | % iron | % carbon |
|---|---|---|
| MIL-88A (crude) | 21.8 | 24.0 | c) MIL-100(Fe) or $Fe_3O[C_6H_3$—$(CO_2)_3]_2.X.nH_2O$ (X=F, Cl, OH)

The mesh parameters are a=73.1 Å and V=393000 Å3, space group Fd-3m (No. 227).

Figure 22:
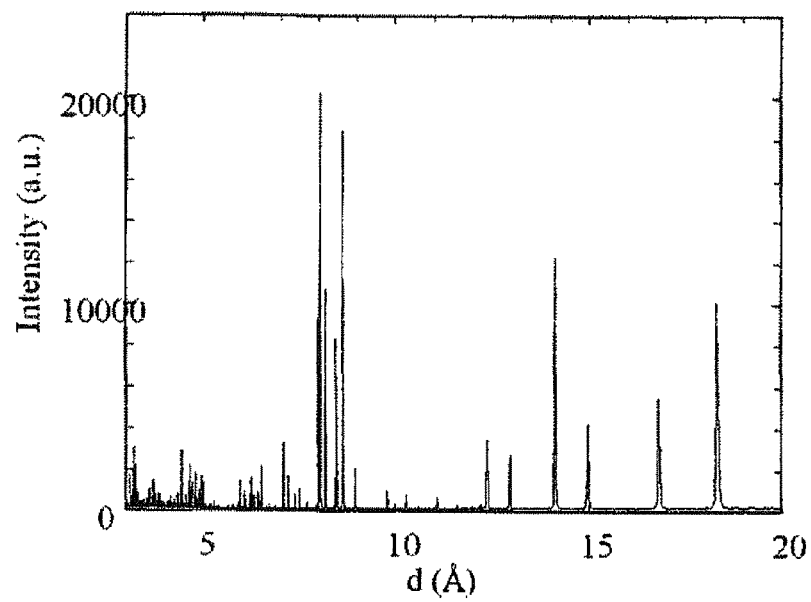
FIG. 22 represents the X-ray diffractogram of the solid MIL-100(Fe).

FIG. 22 represents the X-ray diffractogram of the solid MIL-100(Fe).

Figure 23:
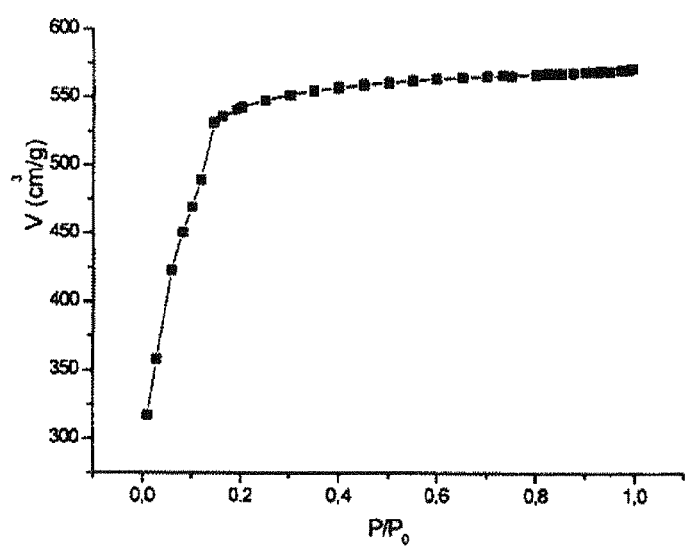
FIG. 23 represents the nitrogen adsorption isotherm at 77 K of the solid MIL-100 (Po=1 atm.).

The specific surface area (Langmuir) for this solid is close to 2900 m$^2 \cdot g^{-1}$. FIG. 23 represents the nitrogen adsorption isotherm at 77 K for the solid MIL-100 (Po=1 atm.).

Figure 24:
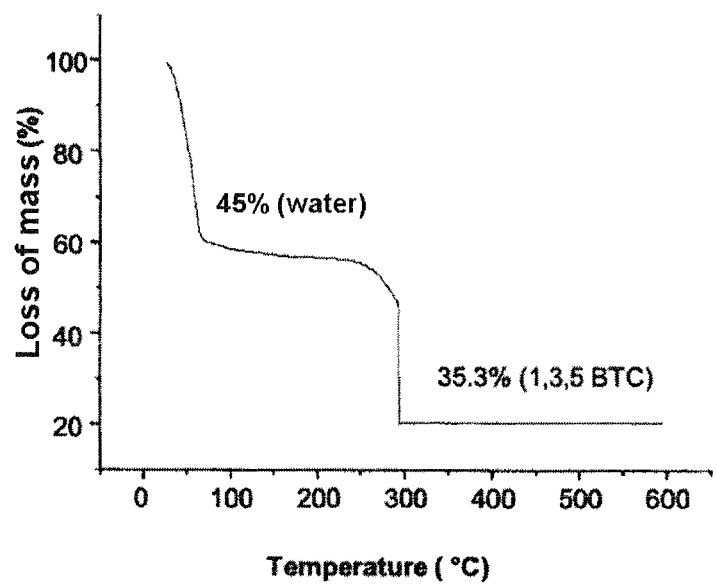
FIG. 24 represents the thermogravimetric analysis (in air) of the crude synthetic compound MIL-100(Fe) (heating rate of 5° C./minute).

FIG. 24 represents the thermogravimetric analysis (in air) for the hydrated compound MIL-100(Fe) (heating rate of 5° C./minute).

TABLE 15

Elemental analysis (CNRS, Vernaison) for the
solid MIL-100(Fe) with X = F

| Element/mass % | % iron | % carbon | % fluorine |
|---|---|---|---|
| MIL-100(Fe) | 13.8 | 23.5 | 1.3% | d) Phase MIL-101(Fe) or $Fe_3O[C_6H_4-(CO_2)_2]_3.X.nH_2O$ (X=F, Cl, OH)

The synthetic conditions are as follows:

0.27 g (1 mmol) of $FeCl_3.5H_2O$ and 249 mg (1.5 mmol) of 1,4-BDC acid dispersed in 10 ml of DMF, the whole left for 12 hours at 100° C. in a 23 ml Teflon body placed in a Paar metallic bomb. The solid is then filtered off and washed with acetone.

The mesh parameters of the solid MIL-101(Fe) at 298 K are: a=89.0 Å and V=707 000 Å3, space group Fd-3m (No. 227).

Figure 25:
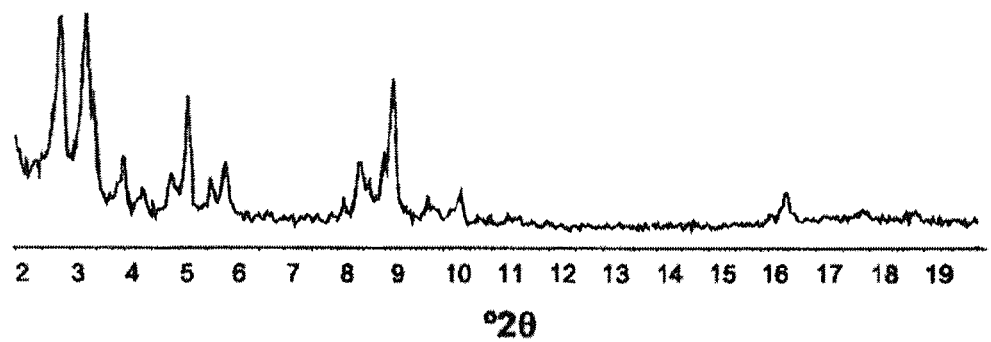
FIG. 25 represents the X-ray diffractogram of the solid MIL-101(Fe) ($\lambda_{Cu}$=1.5406 Å).

FIG. 25 represents the X-ray diffractogram of the solid MIL-101(Fe) ($\lambda_{Cu}$=1.5406 Å).

Optimization of the pore-emptying conditions is underway, and so no specific surface area measurement is available.

Figure 26:
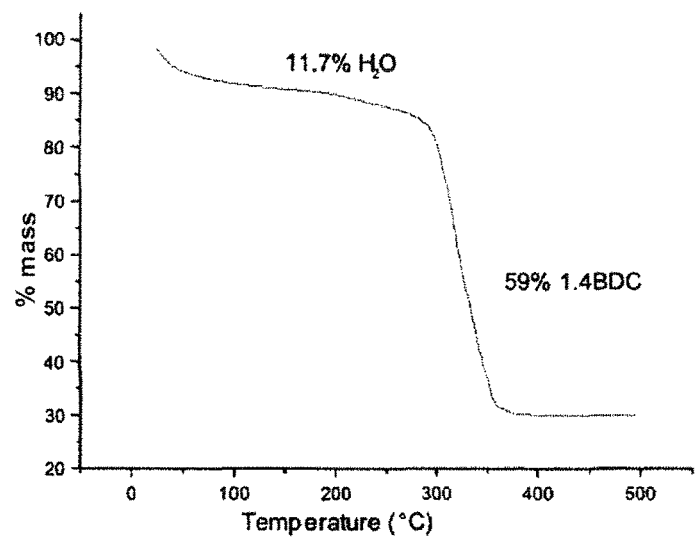
FIG. 26 represents the thermogravimetric analysis (in air) of the hydrated compound MIL-101(Fe) (heating rate of 5° C./minute).
Figure 27:
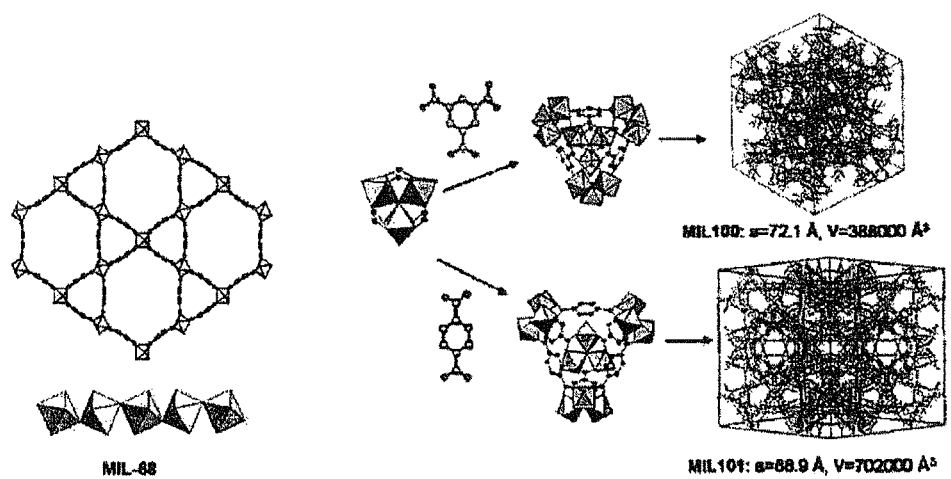
FIG. 27 represents the rigid phases MIL-68 (on the left), MIL-100 (at the top on the right) and MIL-101 (at the bottom on the right).

FIG. 26 represents the thermogravimetric analysis (in air) of the hydrated compound MIL-101(Fe) (heating rate of 5° C./minute).

The theoretical composition of the dry solid (X=F) is as follows: Fe 24.2%; C 41.4%; F 2.7%; H 1.7%.

Example 10: Demonstration of the Flexibility of the Solids

Two types of flexible solid are concerned here. First, the porous metal carboxylates known as MIL-53 and MIL-69, of formulae $Fe(OH)[O_2C-C_6H_4-CO_2]$ and $Fe(OH)[O_2C-C_{10}H_6-CO_2]$, respectively, are formed from octahedral chains linked via dicarboxylate functions, leading to a one-dimensional porous framework, as described in C. Serre et al. *J. Am. Chem. Soc.*, 2002, 124, 13519 [26] and in T. Loiseau et al. *C.R. Acad. Sci.*, 2005, 8, 765 [27]. At room temperature, the solids are hydrated and the pores are closed; when these materials are impregnated with organic solvents, the pores open and substantial porosity (about 8-12 Å) becomes available. The variation in mesh volume between the hydrated forms and the swollen forms ranges between 40% and 110%.

Figure 7:
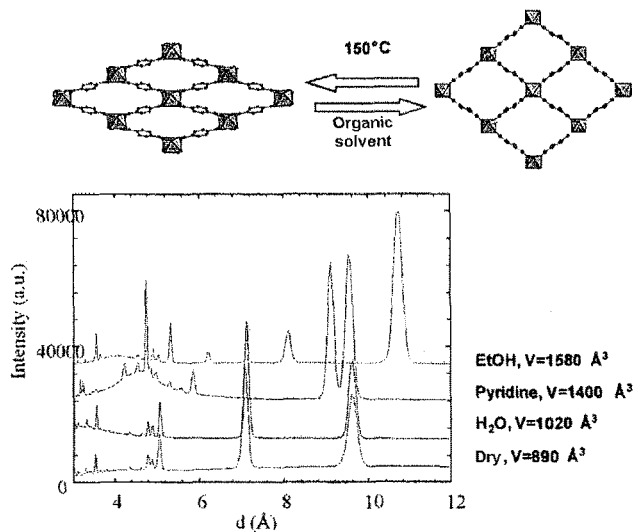
FIG. 7 represents, at the top, the phenomenon of respiration of the compound MIL-53(Fe), and, at the bottom, the X-ray diffractograms of the solid MIL-53(Fe) in the presence of various solvents.

This phenomenon is totally reversible, as represented in the attached FIG. 7. The opening of the pores also depends on the nature of the solvent (FIG. 7). This reflects geometrical adaptation of the structure to the size of the adsorbate, but also optimization of the interactions between the adsorbed molecules and the framework.

The second category of flexible hybrid solids is known as MIL-88. These compounds are constructed from octahedral iron trimers, i.e. three iron atoms connected by a central oxygen and by six carboxylate functions connecting the iron atoms in pairs; a terminal water molecule, coordinated to each iron atom, then completes the octahedral coordinance of the metal. These trimers are then linked together by aliphatic or aromatic dicarboxylic acids to form the solids MIL-88A, B, C, D and MIL-89 from (-A for fumaric acid, -B for terephthalic acid, -C for 2,6-naphthalenedicarboxylic acid, -D for 4,4'-biphenyldicarboxylic acid and MIL-89 for trans,trans-muconic acid), as described in C. Serre et al., *Angew. Chem. Int. Ed.* 2004, 43, 6286 [28] and in C. Serre et al., *Chem. Comm.* 2006, 284-286 [29].

Figure 8:
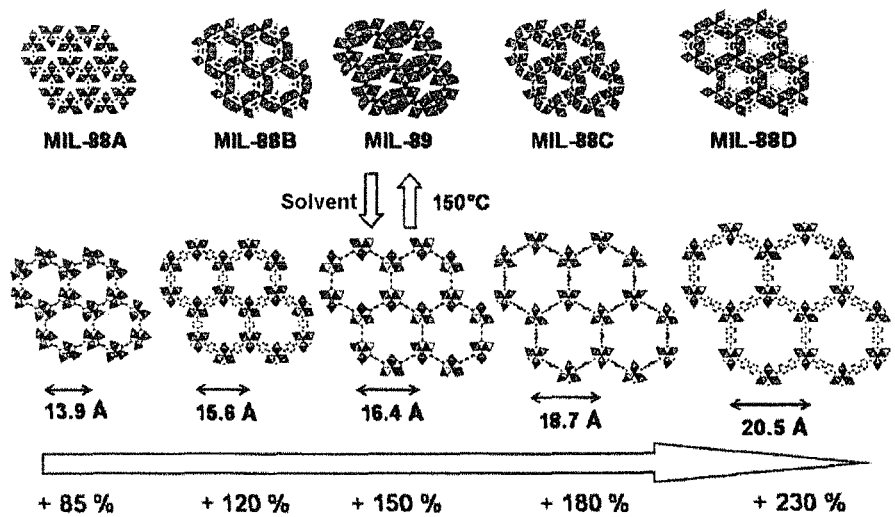
FIG. 8 represents the respiration of the solids MIL-88A, MIL-88B, MIL-88C, MIL-88D and MIL-89. The swelling amplitude between the dry forms (at the top) and open forms (at the bottom) is represented as a percentage at the bottom of the figure.
Figure 9:
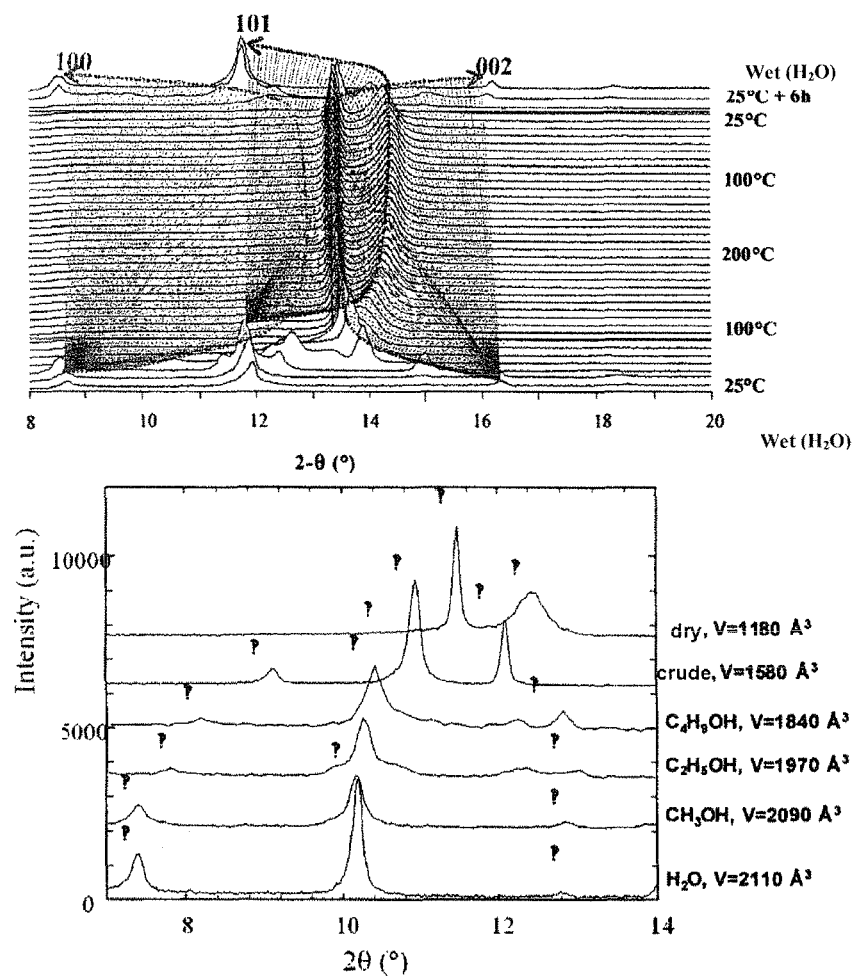
FIG. 9 represents, at the top, the study of the reversibility of swelling of the solid MIL-88A by X-ray diffraction ($\lambda$-1.79 Å), and, at the bottom, the X-ray diffractograms of the solid MIL-88A in the presence of solvents.

Study of the behavior of these solids by X-ray diffraction made it possible to establish that these compounds are flexible, with considerable "respiration" amplitudes between their dry form and their solvated form. This results in mesh volume variations of between 85% and 230% depending on the nature of the organic spacer (FIG. 8), as described in C. Serre et al., *Science*, 2007, 315, 1828 [30]. The inventors have noted that the dry forms are not porous with a more or less identical pore (tunnel) size irrespective of the carboxylic ligand used. On the other hand, the swelling of the hybrid solid in the liquid phase depends on the length of the organic spacer. Thus, the distance between trimers in the swollen form goes from 13.8 Å with fumaric acid (MIL-88A) to 20.5 Å with the biphenyl ligand (MIL-88D). The pore size of the swollen forms thus ranges between 7 Å (MIL-88A) and 16 Å (MIL-88D). The swelling is reversible, as shown by the example of the solid MIL-88A in the presence of water in FIG. 9, and also depends on the nature of the solvent used, as described in C. Serre et al. *J. Am. Chem. Soc.*, 2005, 127, 16273-16278 [31]. Respiration takes place continuously, without apparent breakage of bonds during the respiration. Moreover, on returning to room temperature, the solid swells again by resolvatation, confirming the reversible nature of the respiration.

Figure 10:
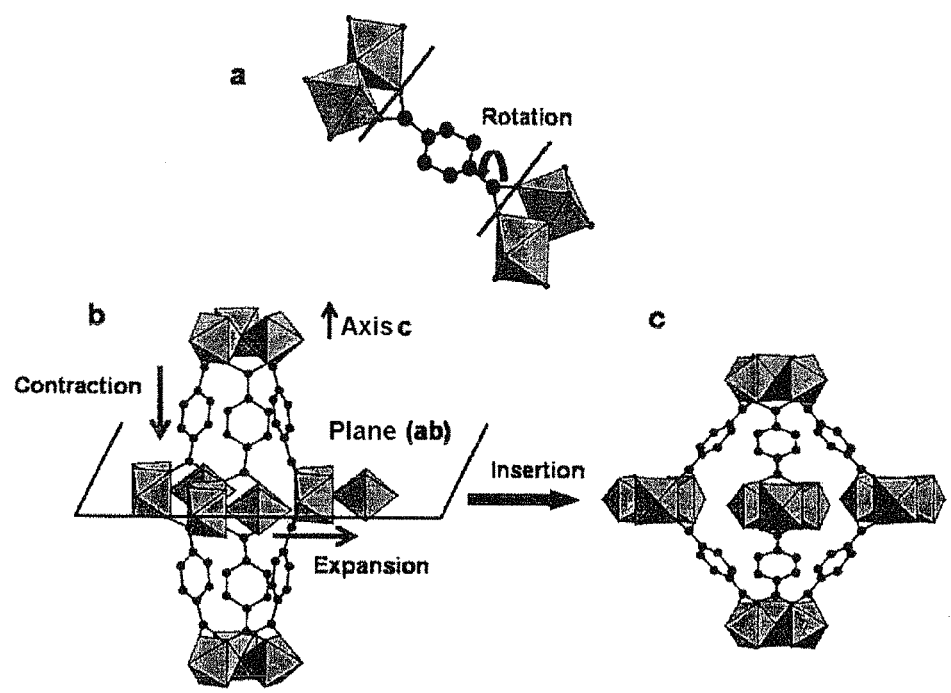
FIG. 10 represents the explanatory scheme of the flexibility in the hybrid phases MIL-53 (a) and MIL-88 (b and c).

How can this flexibility be explained? First, in the case of the solids MIL-53 and MIL-69, they are formed from octahedral chains linked via dicarboxylate bridges (FIG. 10a); examination of the angles between the carboxylate functions connected to the metallic centers and the axis of the inorganic chains is very revealing. If the carboxylate ligand remains flat during respiration, it turns by several degrees about the axis of the chains, thus allowing the structure to change the opening of its pores. Everything takes place as if the axis O—O of the carboxylate functions acted as a ball joint with rotation of the C—C bond of the carboxylate about the aromatic ring to relax the constraints due to the contraction. With respect to compounds MIL-88 and MIL-89, the situation is different (FIGS. 10a and c). Specifically, if we look closely at the arrangement between the constituent trimers of the structure, each trimer is linked to six other trimers, three below and three above, via the dicarboxylates, which leads to the formation of bipyramidal cages of trimers. Within these cages, the connection between trimers is made solely along the axis c and the absence of any bond in the plane (ab) is the origin of the flexibility. Specifically, when a solvent is inserted into the material, the cage becomes deformed, with approach of the trimers along the axis c and distancing in the directions a and b, which causes an overall increase in volume of the cage (FIG. 10). Finally, the flexibility of these hybrid solids is noteworthy, but, however, comparable to that of certain polymers. The main difference concerns the crystallinity of the hybrid solids, polymers being amorphous. Finally, in contrast with polymers, the swelling takes place anisotropically in the hybrid solids.

Example 11: Relaxivity Measurements for an Iron(III) Carboxylate According to the Invention In this example, the relaxivity is measured on the iron(III) fumarate FeTCF MIL-88A.

a) Preparation of Iron(III) Fumarate

A solution of iron chloride (1 mmol) and of fumaric acid (1 mmol) in 4.8 ml of dimethylformamide (DMF) and 0.4 ml of 2M NaOH is placed in a Teflon container with a metallic body and heated at 150° C. for 2 hours. The metallic bomb is then immediately cooled in water. The resulting solid is recovered by centrifugation at 10 000 rpm for 10 minutes. To remove the solvent remaining in the pores, 200 mg of solid are suspended in 100 ml of water with stirring overnight and then recovered by centrifugation (at 10 000 rpm for 10 minutes). 210 nm nanoparticles are obtained.

b) Measurement of the Relaxivity of the Nanoparticles

For each type of nanoparticle, 6 samples containing different concentrations were prepared by suspending them in a water-5% glucose solution (C: 1 mg/ml, 0.5 mg/ml, 0.2 mg/ml, 0.1 mg/ml, 0.05 mg/ml, 0 mg/ml).

The MRI experiments are performed using a 9.4 T horizontal boron magnet (Oxford, UK) guided by Paravision (Bruker, Germany). "Spin-echo" imaging experiments are used for determining the relaxation times T1 and T2 (FOV 15×15 mm; slice thickness: 1 mm; acquisition matrix 32×32). T1 is determined according to a method of reestablishment by saturation (spin-echo sequence: TE=10 ms TR=4000, 2000, 1000, 500, 200, 100 ms) and T2 according to the Carr-Purcell-Meiboom-Gill method (RARE sequence: echo images with a rare factor of 8 and 8; TR/TE=15 000/8 ms). The samples of contrast agent are introduced into the tube. The measurements of T1 and T2 are performed, inducing a total acquisition time of less than 6 minutes. The relaxivity of each type of nanoparticle to a given magnetic field is given by the slope of the line representing the degree of relaxation as a function of the concentration of product.

The ready detection of the MOF nanoparticles makes them good candidates as contrast agents. The efficacy of the contrast agents is directly associated with their relaxivity or their capacity to modify the relaxation times of the protons of water in the surrounding medium when a magnetic field is applied. The greater the amount and mobility of the water molecules in the $1^{st}$ and $2^{nd}$ coordination spheres of the metal, the greater the relaxivity. Thus, the MOF nanoparticles not only have paramagnetic iron atoms, but also a porous structure interconnected with numerous water molecules. Table 16 lists the relaxivity values of the iron fumarate nanoparticles obtained with a magnetic field of 9.4 T. The relaxivity values r1 and r2 of the MIL-88A nanoparticles are of the order of 1 $s^{-1} \cdot M^{-1}$ and 100 $s^{-1} \cdot mM^{-1}$, respectively, which is satisfactory for in vivo use (ref. Roch et al, J Chem Phys 110, 5403-5411, 1999). The relaxivity values are not only related to the iron content, but also to the size of the nanoparticles. PEGylated nanoparticles (whose surface is modified with PEG or polyethylene glycol) have smaller relaxivities r1, but r2 values equal to or slightly higher than those for the non-PEGylated materials. The PEG coating may modify the relaxivities according to two opposite effects: on the one hand, it increases the particle size, and, on the other hand, it reduces their capacity to aggregate.

TABLE 16

Relaxivity of PEGylated or non-PEGylated nanoMIL-88A and nanoMIL-100 nanoparticles, measured at 9.4 T

|  | Fe(mmol/l) | PEG (wt %) | r1 ($s^{-1}mM^{-1}$) | r2 ($s^{-1}mM^{-1}$) |
|---|---|---|---|---|
| MIL88a | 3.75 | 0 | 1.3 | 80 |
| MIL88a with PEG at the surface | 2.91 | 13.6 | 0.86 | 117 |

TABLE 16-continued

Relaxivity of PEGylated or non-PEGylated nanoMIL-88A and nanoMIL-100 nanoparticles, measured at 9.4 T

|  | Fe(mmol/l) | PEG (wt %) | r1 ($s^{-1}mM^{-1}$) | r2 ($s^{-1}mM^{-1}$) |
|---|---|---|---|---|
| MIL 100 | 3.00 | 0 | 0.47 | 60 |
| MIL100 with PEG at the surface | 2.70 | 13.3 | not measured | 53 | c) In Vivo Imaging of the MIL-88A Nanoparticles

The magnetic resonance imaging (MRI) experiments were performed at 300 MHz using a 7 T boron horizontal magnet (Oxford, UK) guided by Paravision (registered trade mark: Bruker, Germany) and equipped with a gradient system (360 mT/m).

Female Wistar rats were injected with doses of 200 mg/kg of MIL-88A(Fe) nanoparticles, the synthesis of which is described previously.

Each rat was sacrificed 30 minutes after injection by an overdose of isoflurane, and then introduced into a probe, equipped with a loop-gap coil 60 mm in diameter. After rapid spatial bearing, a series of proton density weighted images is collected on each animal: RARE sequence [TR/TE=1781.21/8.8 ms; rare factor=4; 4 averages; 39 contiguous slices of 1 mm; FOV 70*70 mm; acquisition matrix 384*384; reconstruction matrix 512*512; resolution in the plane 136 m*136 m; experiment time 8 minutes 32 seconds] and FLASH sequence [TR/TE=564.4/6.7 ms; 2 averages; 39 contiguous slices of 1 mm; FOV 70*70 mm; acquisition matrix 384*384; reconstruction matrix 512*512; resolution in the plane 136 m*136 m; experiment time 7 minutes 13 seconds].

Four slices were analyzed in each region of interest (the liver and the spleen). Furthermore, for each organ, the average values of the RIs were calculated and normalized relative to the region corresponding to the dorsal muscle. The results obtained by MRI clearly show that an injection of nanoparticles leads to large contrast differences in the two organs studied, the liver and the spleen. Moreover, the two sequences FLASH and RARE show that the organs of the rats injected with the nanoparticles appear darker than those of the untreated rats. The good in vivo detection of the iron carboxylate nanoparticles makes them candidates of interest for magnetic resonance imaging.

Example 12: In Vivo Tests of Toxicity of Iron(III) Carboxylates a) Iron Carboxylates Tested The following two iron carboxylate solids (synthesized according to the procedures of Example 1) are respectively tested:
MIL-88A(Fe) of composition $Fe_3O[O_2C-C_2H_2-CO_2]_3 \cdot OH \cdot nH_2O$
MIL-88Bt(Fe) of composition $Fe_3O[O_2C-C_6(CH_3)_4-CO_2]_3 \cdot OH \cdot nH_2O$ b) Toxicity Tests Study of the acute in vivo toxicity is performed on 4-week-old female Wistar rats (~125 g) by intravenously injecting into the rats increasing doses (50, 100 and 200 mg/kg) of MIL-88A (210 nm) and MIL-88Bt (100 nm) nanoparticles suspended in 0.5 ml of a 5% glucose solution.

The nanoparticles are stable in this medium.

The stability time of these suspensions is reduced to a few minutes when the particle concentration is maximal (200 mg/kg, ~25 mg/0.5 ml). For this reason, the samples are withdrawn under gentle stirring of the nanoparticle suspensions. It was not possible to administer doses higher than 200 mg/kg, since the maximum volume injectable into the rats is 0.5 ml.

The results are promising given that no major sign of toxicity is observed after 7 days of test. The serum values for albumin, cholesterol and transaminases (ASAT/ALAT) do not show any significant variation after 7 days of test and the weight of the organs relative to the body weight does not vary significantly (Table 7).

TABLE 17

Seric parameters measured 7 days after the intravenous introduction of the iron carboxylates MIL-88A(Fe) and MIL-88Bt(Fe)

| | Dose (mg/kg) | Albumin (g/L) | CHOL (mmol/L) | ASAT/ ALAT | Organ weight/total weight | | |
|---|---|---|---|---|---|---|---|
| | | | | | liver | kidney | spleen |
| Control | — | 44.2 | 2.5 | 2.5 | 0.041 | 0.009 | 0.004 |
| MIL-88A | 50 | 37.6 | 3 | — | 0.044 | 0.012 | 0.004 |
| MIL-88A | 100 | 46.0 | 2.2 | 2.5 | 0.041 | 0.009 | 0.004 |
| MIL-88A | 200 | 40.2 | 2.9 | 2.6 | 0.048 | 0.008 | 0.004 |
| MIL-88Bt | 50 | 39.5 | 2.5 | — | 0.048 | 0.010 | 0.003 |
| MIL-88Bt | 100 | 42.1 | 2.6 | 2.4 | 0.046 | 0.008 | 0.003 |
| MIL-88Bt | 200 | 38.5 | 2.6 | 2.5 | 0.044 | 0.008 | 0.004 |

Figure 13:
FIG. 13 represents histological rat liver sections revealed by staining with hematoxylin-eosin and a Proust stain.

The histological sections of the liver are observed by Proust staining (iron in blue), and presented in FIG. 13. They show an accumulation of iron in the liver. Although it is necessary to perform a more in-depth study on the long-term effects of these solids in the body, these results are very promising, and make it possible to envision biomedical applications for these materials.

Acute and subacute toxicity studies were performed in greater depth.

The animals used for the experiment are 4-week-old female Wistar rats weighing 161.36±16.1 g.

All the tests were performed in the animal house of the University Pharmacy school under temperature and humidity conditions, and after 3 days of adapting the animals to the animal house (3 days).

For the acute toxicity tests, a single intrajugular injection of the materials MIL-88A (150 and 500 nm), MIL-88Bt (50 and 140 nm) or 5% glucose (control group) is performed on 4 groups (at 1 day, 1 week, 1 month and 3 months, respectively) of 8 rats chosen at random and anesthetized with isoflurane.

The change in weight and the behavior of the animals were monitored.

Blood samples from the jugular vein under anesthesia with isoflurane were also taken at different times: 1 and 3 days, 1 and 2 weeks, 1, 2 and 3 months. The serum was isolated to measure the seric parameters such as IL-6 (interleukin 6), albumin, seric Fe, PAS, GGT, bilirubin, cholesterol and transaminases.

Moreover, each group of animals was sacrificed after 1 day, 1 week, 1 and 3 months, respectively. The animals were anesthetized with isoflurane and the spleen, kidneys, liver and heart were then removed and stored for histological studies. Four livers were also used to perform a microsomal extraction in order to measure the activation of cytochrome P450.

For the subacute toxicity tests, one intrajugular injection per day is performed for 4 consecutive days on 26 rats distributed at random into different groups, in which the animals are sacrificed after 5 or 10 days.

The change in weight of the isolated animals and their eating behavior (measurement of the amounts of water and feed consumed) were monitored. The urine and dejecta were also recovered.

Blood samples from the jugular vein were also taken on different groups of rats at 3 and 5 days, and 8 and 10 days. The blood undergoes the same treatment as for the acute toxicity test, and the serum obtained is intended for the same analyses.

On the days of sacrifice, at 5 and 10 days, the animals are anesthetized with isoflurane and the spleen, kidneys, liver, heart and lungs are then removed and treated in the same way as for the acute toxicity test.

c) Results

Weight Change of the Animals:

The animals were weighed every day for the purpose of comparing the weight change of the various groups. A mean was determined for each day and in each of these groups.

For the subacute toxicity tests, the weight increase observed with the glucose group is slightly reduced when the material is administered. This variation is more obvious when the administered dose is higher.

The acute toxicity studies show that the administration of the materials MIL-88A and MIL-88Bt does not produce a significant variation in weight over time.

Change in Consumption of Water and Feed:

In subacute toxicity, the change is similar overall for the control group and the group which received an injection of 25 mg/kg. A more pronounced difference is observed in the group which received the highest dose and is characterized by smaller consumption of feed during the study. This observation is confirmed and completely agrees with the results obtained for the weight change.

Comparison of the Weight of the Removed Organs:

Subacute toxicity results: no significant difference appears between the weight of the spleen, kidneys and heart for the various groups. The weight of the lungs appears to be slightly increased at 5 days and at 10 days.

Acute toxicity: an increase in the weight of the spleen is observed up to one week after administration, and returns to normal at 1 and 3 months for MIL-88A and MIL-88Bt, respectively. The liver weight increases substantially when the materials are injected, which possibly reflects the accumulation of iron in the liver. It is observed that the situation returns to normal for MIL-88A after 3 months, but not for MIL-88Bt, where the weight remains high.

Cytochrome P450 Assay in Microsomal Suspensions:

Cytochrome P450 is an enzyme associated with the inner face of the smooth endoplasmic reticulum, which is highly involved in the degradation of exogenous molecules. This enzyme has very low substrate specificity and is capable of catalyzing the transformation of newly synthesized compounds such as medicaments. The majority of the P450 cytochromes can be induced or repressed, at the transcriptional level, by various xenobiotics; this is often the cause of side effects of medicaments. Assaying this enzyme makes it possible to determine whether the MOF material used is metabolized by cytochrome P450, in which case it will activate or inhibit its activity.

The amount of cytochrome can be interpreted only on condition that it has been related to the total amount of protein contained in each sample. Assay of the protein contained in the sample was performed by means of a BCA kit supplied by Pierce (batch #HI106096). This method combines the reduction of $Cu^{2+}$ to $Cu^+$ by the proteins in alkaline medium with very sensitive and selective colorimetric detection of the $Cu^+$ cation by means of a reagent containing bicinchoninic acid (BCA).

The relationship between the cytochrome concentration and the total amount of protein gives the cytochrome activity expressed in $mol \cdot g^{-1}$. The acute toxicity results show that there is no major difference in activity between the negative control group (which received glucose) and the "MIL-88A" group, the material of which is not metabolized by Cyp450. The material MIL-88Bt does not appear to be metabolized by Cyp450 either.

Assay of the Interleukin 6 in the Serum:

Interleukin 6 (IL-6) is a multifunctional cytokine that plays an important role in host defense, immune responses, nerve cell functions and hematopoiesis. An elevated level of IL-6 in the serum has been observed, for example, during viral and bacteriological infections, trauma, autoimmune diseases, inflammation or cancer.

The aim of this study is to determine whether there is an inflammatory reaction after administration of the iron carboxylate nanoparticles. Thus, it is possible to see whether the level of IL-6 is increased relative to control groups (injection of glucose, and thus local inflammatory reaction due to the injection).

The assay was performed by using a "Quantikine, Rat IL-6" kit supplied by R&D Systems laboratories.

Subacute toxicity results: the variations are not significant. An increase in the plasmatic level observed (activation of IL-6 production) appears to be a phenomenon due to the injection, which causes a local inflammation, if the various groups are compared in isolation with the control group (glucose).

Acute toxicity results: the variations are not significant and lead to the same conclusions as in the case of the subacute toxicity.

Assay of the Seric Parameters:

All the assays were performed using automatic devices. A few key parameters were determined to evaluate the consequences of injection of nanoparticles into the liver, the levels of transaminases (alanine aminotransferase or ALAT and aspartate aminotransferase or ASAT), alkaline phosphatases (PAS), γ-glutamate transferase (GGT), bilirubin, cholesterol, albumin and seric iron.

The results show that the seric levels of ALAT are entirely normal, as are the levels of bilirubin (<2 µmol/L) and of γ-glutamate transferase (<2 IU/L).

The serum albumin levels were slightly reduced after the first day of injection for the two materials, which is in agreement with a local inflammatory process due to the injection, and with the increase in IL-6 observed previously. After 3 days, the levels return to normal.

The seric levels of ASAT are increased one day after injection, which may indicate a cytolysis process. However, 3 days after administration of the nanoparticles, the values return to normal. Similarly, the alkaline phosphatase is increased after 1 day, indicating a cytolysis process, but the situation returns to normal after 3 days. The return to normal after 3 days indicates that it is a transient rather than permanent cytolysis process. There is therefore no loss of cell function.

The cholesterol levels are normal.

The seric iron levels are decreased in comparison with the control group, and this is more pronounced in the MIL-88A group. This might be explained by complexation of the seric iron by the nanoparticles. The situation returns to normal 3 days after the administration.

The seric parameters were also assayed at 1 week and, from these results, there is no longer any difference between the 3 groups with respect to the seric iron; the rats treated with MIL-88A and MIL-88Bt recovered a seric iron concentration comparable to that of the control group. Moreover, with respect to the levels of the other seric parameters, there is no significant difference in comparison with the control group.

Histological Sections:

Histological sections 5 µm thick are made in a cryostat, dehydrated and stained (hematoxylin/eosin stain and then Proust blue stain: blue coloration of the iron).

By observing the histological sections, it is possible to determine the route of elimination of the compounds of the material or their storage in certain organs: liver, kidneys, spleen and lungs, the heart being used as control.

Acute toxicity results: the liver histological sections show an accumulation of iron in the liver after injection of the materials, which is higher for the solid MIL-88A. The material appears to be in the form of nondegraded nanoparticles. The accumulation is smaller for the material MIL-88Bt, which may mean lesser uptake for the liver or the more rapid reuse of the stored iron. After 1 and 3 months, the iron content in the spleen and the liver returns to normal.

Assay of the Iron in the Injected Suspensions and in the Organs:

The assay of the iron contained in the suspensions of MIL-88A and MIL-88Bt injected into the animals is performed by UV-visible spectrophotometry at a wavelength of 520 nm, by specific colorimetry of the ferrous ions with bipyridine (formation of a red complex), after dissolving the iron oxide in concentrated sulfuric acid, and reducing the ferric ions to ferrous ions with ascorbic acid.

The assay of the iron in the organs is performed in the same way as the iron assay of the suspensions explained previously, after grinding the organ to be tested. This assay makes it possible to determine the route of elimination of the compounds of the material or their storage in certain organs: liver, kidneys, spleen and lungs, the heart being used as control.

d) Conclusion

During the toxicity tests, minute observation of the animals revealed no apparent sign of harmfulness of the injected material. Specifically, the animals maintained entirely normal behavior. During the studies, the animals put on weight well, in comparison with the control group, even though for the subacute toxicity study the weight increase is smaller than for the control group, probably associated with the consecutive administration of higher doses. The water consumption remains normal on the whole in the subacute toxicity test.

A cytochrome P-450 assay made it possible to observe the state of activity of cytochrome P-450 over a long period. This cytochrome is known for its capacity to metabolize certain xenobiotics. The study shows that the activity level, although subject to fluctuation, remains below the values observed on the control rats who received an injection of phenobarbital, a cytochrome P-450 activator, which indicates that the materials are not metabolized via the Cyp450 route, which is in agreement with the high polarity of the dicarboxylic ligands.

The results are very promising and already indicate that the materials MIL-88A and MIL-88Bt do not induce any sign of severe toxicity, although complementary toxicity studies must be performed. The fate and the effects of the nanoparticles in the body are in the course of being studied in order to bring into touch the benefit provided by these materials by vectorizing medicaments that are difficult to encapsulate and that are of great therapeutic potential. Similar studies are also underway with other nanovectors of different structure and/or composition.

Example 13: In Vitro Degradation of MIL-88A Nanoparticles a) Study No. 1

The degradation of MIL-88A nanoparticles was studied during their incubation at 37° C. in a phosphate-buffered solution (PBS) at pH 7.4, with two-dimensional stirring. The concentration of nanoparticles was 50 µg/ml. After various incubation times, the nanoparticle suspensions were centrifuged (10 000 rpm, 15 min, 0° C.). The fumaric acid freed by degradation of the nanoparticles was quantified in the supernatant by reverse-phase HPLC, by means of spectrophotometric detection ($\lambda$=210 nm). We used a reverse-phase C18 Symmetry column (registered trademark) (5 µm, 3.9× 150 mm, Part. No. WAT046980, Waters). The mobile phase was a mixture of methanol (25% by volume) (Aldrich, HPLC grade) and 10 mM phosphoric acid (75% by volume) (Aldrich, HPLC grade). The flow rate of the mobile phase was 0.5 ml·min$^{-1}$ and the column temperature was 25° C. The injection volume was 10 µL. The system was calibrated with standard solutions of fumaric acid. The retention time of this product was about two minutes.

Figure 34:
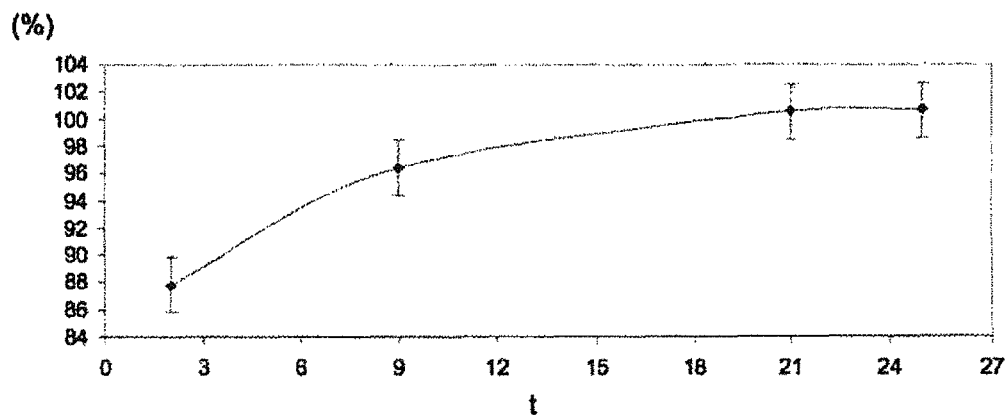
FIG. 34 represents the release of fumaric acid from the solid MIL-88A as a percentage (%) as a function of time t (in days).
Figure 35:
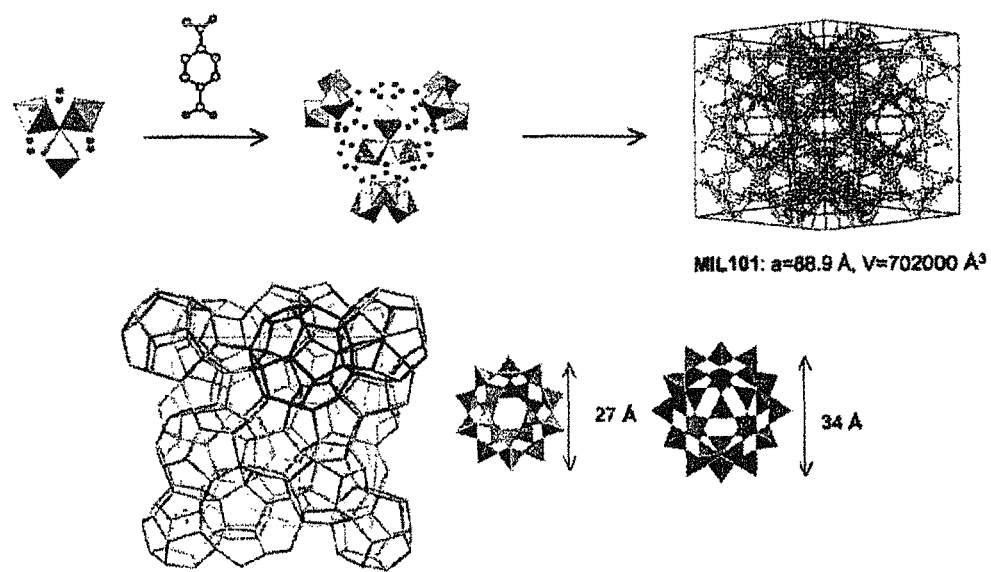
FIG. 35 represents the structure of the solid MIL-100(Fe). (a): octahedral trimer and trimesic ligand; (b): supertetrahedron; (c): 3-D schematic structure; (d): the two types of mesoporous cage.
Figure 36:
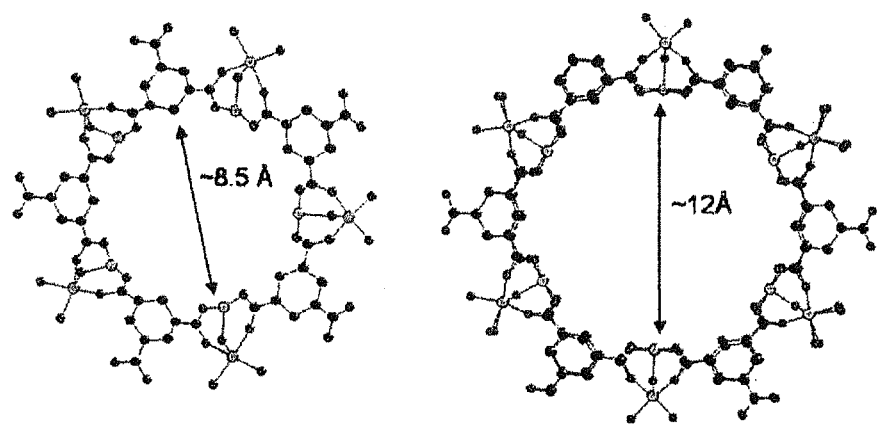
FIG. 36 represents the pentagonal and hexagonal windows of the solid MIL-100(Fe) after activation under vacuum.
Figure 37:
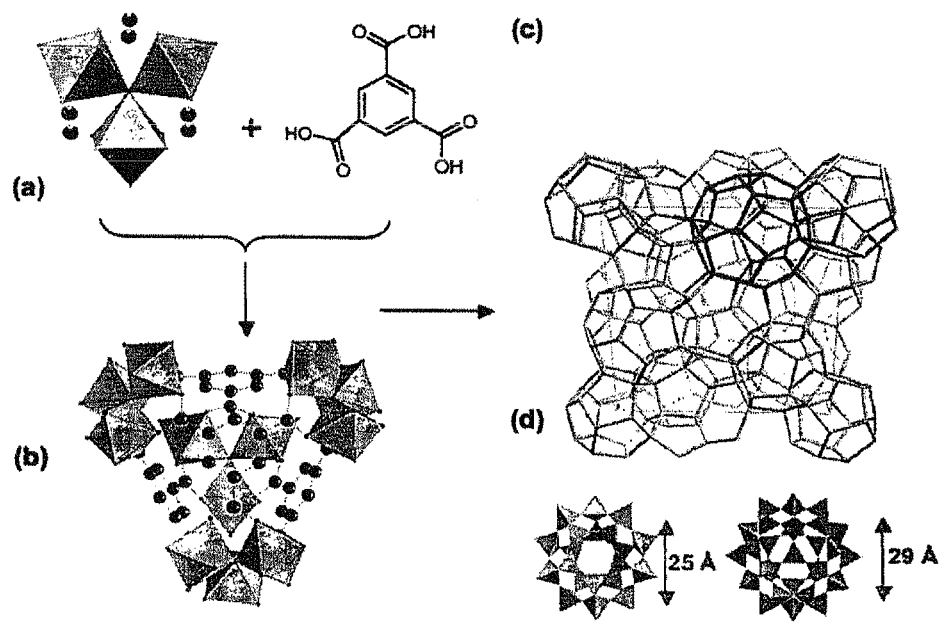
FIG. 37: Top: construction of the solid MIL-101 from octahedral iron trimers, 1,4-benzenedicarboxylic acid, to form a hybrid supertetrahedron and finally a hybrid zeolite structure with a large pore size. Bottom: schematic view of the porous framework and representation of the two types of mesoporous cage, with their free dimensions. The iron octahedra and the carbon atoms are in green and black, respectively.
Figure 38:
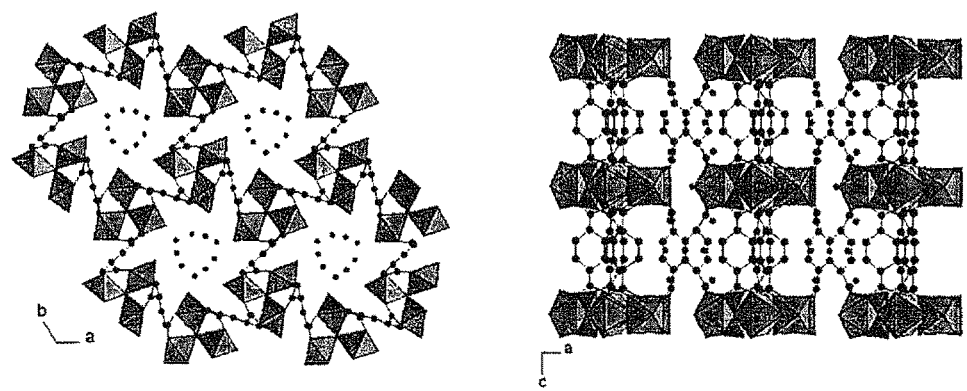
FIG. 38 represents the structure of the MOF solid MIL-102(Fe). Left: view along the axis of the tunnels (axis c); right: view along the axis perpendicular to the tunnels (axis b, similar view along the axis a). The iron and carbon atoms and the water molecules are in green, black and red, respectively.
Figure 39:
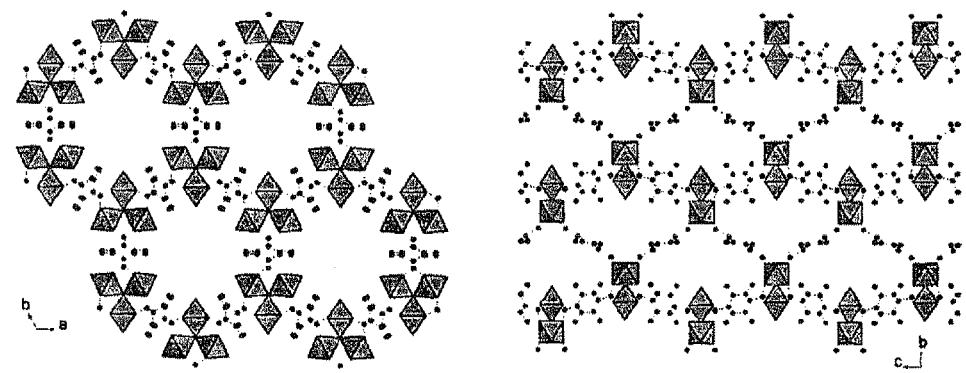
FIG. 39: Structure of the MOF solid MIL-88B_4CH$_3$(Fe). Left: view along the axis of the tunnels (axis c); right: view along the axis of the cages (axes a and b equivalent). The iron octahedra and the carbon atoms are in orange and black, respectively.
Figure 40:
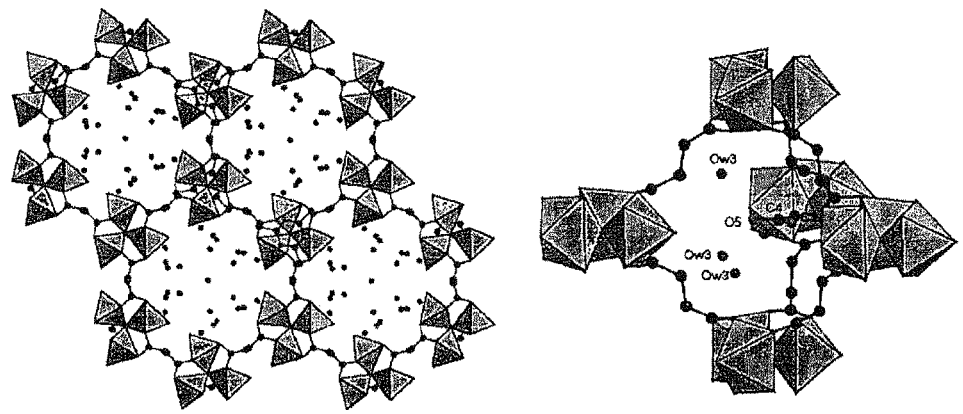
FIG. 40: Structure of the iron carboxylate MIL-88A (hydrated). Left: view along the axis of the tunnels (axis c); right: view along the axis perpendicular to the tunnels (axis b, similar view along axis a). The iron octahedra, the carbon atoms and the water molecules are in green, black and red, respectively.
Figure 41:
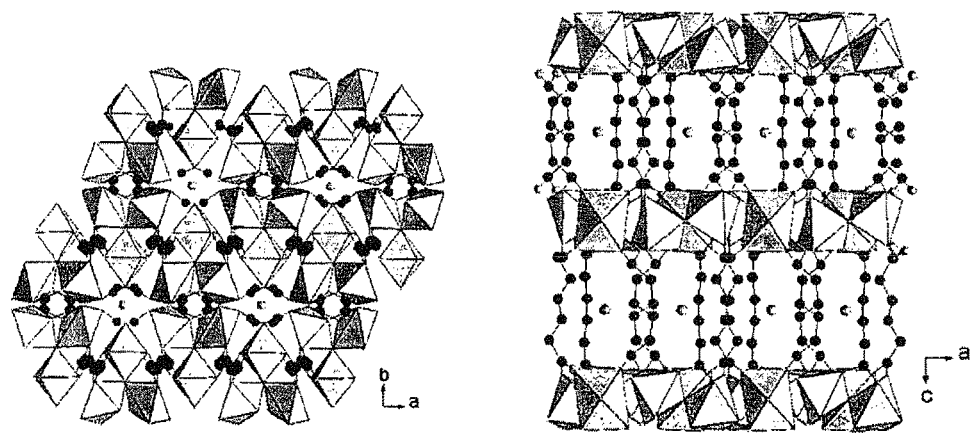
FIG. 41: Structure of the iron carboxylate MIL-89(Fe). Left: view along the axis of the tunnels (axis c); right: view along the axis perpendicular to the tunnels (axis b, similar view along axis a). The iron and carbon atoms and the water molecules are in gray, black and white, respectively.

We observed that after two days of incubation, about 88% of the total amount of fumaric acid included in the nanoparticle composition had been released: FIG. 34 represents the release of fumaric acid from the solid MIL-88A as a percentage (%) as a function of time t (in days). Total degradation (100% fumaric acid released) was observed after three weeks of incubation.

b) Study No. 2

Degradation of the material MIL-88Anano (150 and 500 nm) was studied using a suspension of the nanoparticles (50 mg/ml) in a pH 7.4 PBS solution at 37° C. with two-dimensional stirring. At various times, the supernatant is recovered by centrifugation (10 000 rpm/10 min at 0° C.) and the amount of fumaric acid released is determined by HPLC (reverse phase, Waters 501 HPLC pump, Waters™ 717 plus autosampler, Waters™ 486 detector and UV-visible spectrophotometer at $\lambda$=210 nm). The Symmetry® C18 reverse-phase column (5 µm, 3.9×150 mm, Part No. WAT046980, Waters) is used. The mobile phase is a mixture of methanol (25 vol %) (Aldrich, HPLC grade) and 10 mM phosphoric acid (75 vol %) (Aldrich, HPLC grade). The flow rate is 0.5 ml·min$^{-1}$ and the column temperature is 25° C. The injection volume is 10 µL.

The fumaric acid retention time is two minutes. The fumaric acid concentration is determined using a calibration curve with standards.

88% of the total amount of fumaric acid of the nanoparticles is released after two days of incubation, and about 96% after nine days. Total degradation is produced after three weeks of testing.

V. Nanoparticles Loaded with a Molecule of Interest

Example 14: Formulation of Iron(III) Carboxylate Nanoparticles Loaded with Active Principle: Busulfan Busulfan (1,4-butanediol dimethylsulfonate) is an alkylating agent of the alkylsulfonate class which is of certain therapeutic value for treating cancer. Prescribed in "high-dose" chemotherapy protocols before self-grafting or allografting of hematopoietic stem cells, it constitutes an excellent alternative to full body irradiation and is consequently of particular interest in pediatrics. However, as it is mainly taken up by the liver, it has high toxicity, whence the interest in developing carrier systems.

The busulfan release systems tested up to now pose a real challenge with respect to its encapsulation. The maximum loading obtained with liposomes does not exceed 0.5% (by weight). The use of biodegradable polymers has proven to be more suited, but the degree of encapsulation of busulfan does not exceed 5% (by weight) of busulfan in poly(alkyl cyanoacrylate)-based nanoparticles.

In this example, busulfan is incorporated into various iron(III) carboxylates according to the invention, and especially the materials MIL-53, MIL-88A, MIL-89 and MIL-100.

a) Preparation of the MIL-53 Iron Carboxylate

The MIL-53 solid is synthesized from 270 mg of $FeCl_3.6H_2O$ (1 mmol; Alfa Aesar, 98%), 166 mg of 1,4-dicarboxylic acid (1 mmol; Aldrich, 98%) and 5 ml of dimethylformamide (Fluka, 98%). The whole is introduced into a Teflon body placed in a metallic body (autoclave) of Paar brand, and then heated at 150° C. for 24 hours. After cooling to room temperature, the product is recovered by filtration and washed with water and acetone.

200 mg of the solid are then suspended in 100 ml of distilled water with stirring for 15 hours to remove the residual solvent present in the pores. The solid is recovered by filtration.

The particle size measured by light scattering is 6.2 microns.

b) Preparation of the MIL-88A Iron Carboxylate

To obtain the material MIL-88A, 270 mg of $FeCl_3.6H_2O$ (1 mmol; Alfa Aesar, 98%), 112 mg of fumaric acid (1 mmol; Acros, 99%) in 5 ml of dimethylformamide (Fluka, 98%) are mixed together, and 0.4 ml of 2M NaOH is added. The whole is introduced into a Teflon body placed in a metallic body (autoclave) of Paar brand, and then heated at 100° C. for 15 hours. After cooling to room temperature, the product is recovered by filtration and washed with water and acetone.

200 mg of the solid are suspended in 100 ml of distilled water with stirring for 15 hours to remove the residual solvent present in the pores. The solid is then recovered by filtration.

The particle size measured by light scattering is 2.6 microns.

c) Preparation of the MIL-89 Iron Carboxylate 240 mg of iron acetate (0.33 mmol) and 140 mg of muconic acid (1 mmol) are added to 9 ml of methanol. A solution of 0.35 ml of 2M NaOH is then slowly added to 1 ml of methanol. The whole is placed in a Teflon container with a metallic body and heated at 150° C. for six hours. The metallic bomb is then immediately cooled in water. The resulting solid is recovered by centrifugation at 5000 rpm for 10 minutes. To remove the solvent remaining in the pores, 200 mg of solid are suspended in 100 ml of water with stirring overnight and then recovered by centrifugation (5000 rpm, 10 minutes).

The particle size measurement by light scattering shows two populations of nanoparticles of 1.1 microns.

d) Preparation of the MIL-100 Iron Carboxylate

The synthesis of MIL-100 is performed starting with 56 mg of iron metal (1 mmol; Aldrich, 99%) and 210 mg of 1,3,5-benzenetricarboxylic acid (1,3,5-BTC; 1 mmol; Aldrich, 95%) in 3 ml of distilled water, to which are added 0.4 ml of hydrofluoric acid (HF; 5M) and 0.6 ml of 2N nitric acid. The whole is introduced into a Teflon body placed in a metallic body (autoclave) of Paar brand. The whole is heated with a heating ramp of 12 hours (25 to 150° C.) for six days at 150° C. and with a cooling ramp of 24 hours. The product is recovered by filtration and washed with water and acetone.

200 mg of solid are suspended in 100 ml of distilled water with stirring and refluxing for three hours to remove the residual acid present in the pores. The solid is then recovered by filtration while hot.

The particle size measured by light scattering is 1.7 microns.

e) Introduction of Busulfan into the Iron Carboxylates

The insertion of busulfan into the pores of the materials is performed by adsorption, by suspending 25 mg of dehydrated solid in 2.5 ml of a solution containing the medicament with a concentration equal to 100% or 80% of its saturation in the solvent, the whole being stirred for 16 hours at room temperature. The particles are then recovered by centrifugation (20° C., 5000 rpm, 15 min). The pellet is dried (evaporation under a primary vacuum mmHg, 72 hours) until a constant weight is obtained. Quantification of the busulfan present in the porous solid is performed by radioactive counting ($^3$H-busulfan), thermogravimetric analysis (TGA) and elemental analysis.

The solvents chosen for the impregnation are those in which busulfan has appreciable solubility (acetone, acetonitrile, chloroform, dichloromethane, dimethyl carbonate) (Table 18).

TABLE 18

Solubility of busulfan in various solvents

| Solvent | Busulfan solubility (mg/ml) |
|---|---|
| Acetonitrile | 30 |
| Acetone | 20 |
| Dichloromethane | 10 |
| Chloroform | 8 |
| Dimethyl carbonate | 13 |
| Ethyl acetate | 6.6 |
| Tetrahydrofuran | ~5 |
| Toluene | ~4 |
| Water | 0.1 |
| Ethanol | <<<4 |
| Methanol | <<<4 |
| Hexane | <<<4 |
| Ether | <<<4 |

The first tests of introduction of busulfan into the materials MIL-53, MIL-88A, MIL-89 and MIL-100 are listed in Table 19.

TABLE 19

Hybrid solids used for the busulfan encapsulation tests

| MIL-n | Organic spacer | Symmetry | Flexibility | Pore size (nm) | Dp (nm) |
|---|---|---|---|---|---|
| MIL-53 | 1,4-BDC acid | C2/c | Yes | 0.86 | 6200 |
| MIL-88A | Fumaric acid | P-62c | Yes | 0.6 | 2600 |
| MIL-89 | Muconic acid | Pbnn | Yes | 0.9 | 1100 |
| MIL-100* | 1,3,5-BTC acid | Fd3m | No | 2.5-2.9 | 1700 |

*Note: the MIL-100 solid comprises two types of cage (25 and 29 Å) but these cages are accessible via pentagonal or hexagonal microporous windows of dimensions 4.8 * 5.8 and 8.6 Å.

The busulfan loading capacities obtained are large, up to 122 and 153 mg/g hydrated solid containing the medicament in MIL-53 and MIL-100, respectively (Table 10). The starting solids contain, respectively, 7.3 and 44.5 weight % of water.

Considering the content relative to that of the dry solid, the storage capacity exceeds 25% by weight of active principle, which surpasses by a factor of 60 those obtained with liposomes and by a factor of 4 those obtained with the best polymer-based systems.

TABLE 20

Mass percentage of busulfan (estimated by elemental analysis) present in MIL-53, MIL-88A, MIL-89 and MIL-100 hybrid solids as a function of the impregnation conditions

| | % Busulfan | | | | | | | | | | |
|---|---|---|---|---|---|---|---|---|---|---|---|
| | MIL-53 | | MIL-88A | | | MIL-89 | | | MIL-100 | | |
| Solvents | 2 h* | 14 h** | 2 h* | 16 h* | 14 h** | 2 h* | 16 h* | 14 h** | 2 h* | 16 h* | 14 h** |
| Acetone | 5.0 | 1.8 | 2.4 | 4.4 | 1.2 | — | 3.0 | 2.2 | 1.4 | 4.6 | 2.4 |
| Acetonitrile | 7.6 | 2.3 | 5.8 | 4.7 | 1.9 | 1.9 | 6.0 | 3.9 | 6.2 | 5.3 | 6.8 |
| Chloroform | 1.2 | 1.3 | 1.6 | 1.3 | 1.0 | — | 2.2 | 0.9 | 3.4 | 4.1 | 3.6 |
| Dichloromethane | 12.2 | 1.6 | 7.0 | 1.3 | 1.4 | 2.8 | 2.8 | 1.8 | 13.2 | 9.5 | 15.3 |
| Dimethyl carbonate | 3.6 | | 1.9 | | | 4.8 | | | 2.3 | | |

Figure 14:
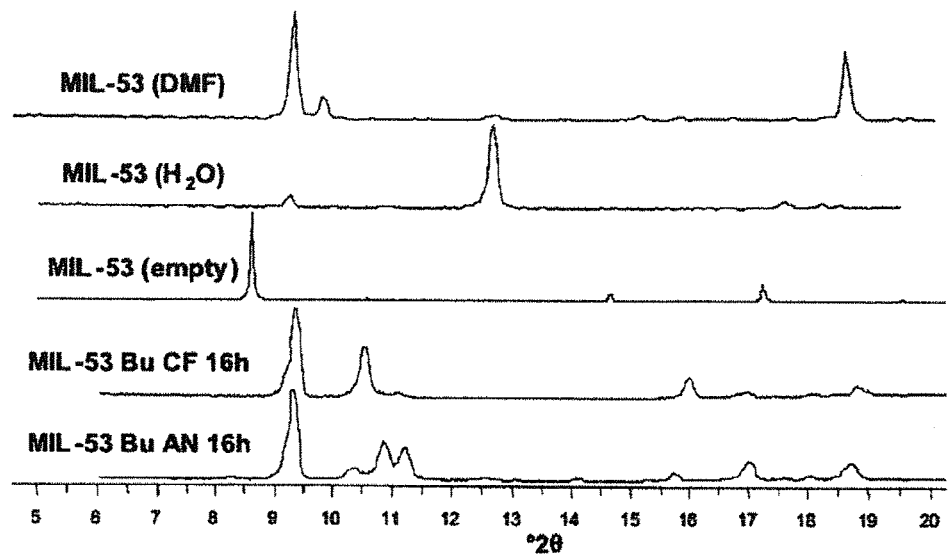
FIG. 14 represents the X-ray powder diffractograms of the solids MIL-53 encapsulating various species: dimethylformamide (DMF), $H_2O$ and busulfan (adsorbed from chloroform or acetonitrile solutions). The X-ray diffractogram of the dry form is also represented ("empty").

*Concentration of busulfan in solvents at 100% saturation
**Concentration of busulfan in solvents at 80% saturation These results are very encouraging, and optimization of the impregnation conditions is underway in order to further increase the degree of encapsulation. It is also pointed out that the amount adsorbed in the flexible hybrid solids of the type MIL-53 or MIL-88 may be monitored qualitatively by X-ray diffraction (FIG. 14) since the opening of the pores of the hybrid solid depends on the content of active principle in the pores.

The encapsulation of busulfan may be optimized by testing:
  Several impregnation cycles
  Different impregnation times
  Encapsulation by sublimation
  Use of several solids with a larger pore volume (MIL-101 biphenyl, MIL-88D modified with different organic groups) and of hybrid solids with modified ligands (NH2, Cl, NO2, COOH, CH3, etc.) to optimize the medicament-solid interactions. At this stage, digital simulation will be used to predict the best function for retaining busulfan in the pores.
As a function of the encapsulation results, we will use solid nanoparticles surface-modified with PEG for encapsulation tests.

Example 15: Formulation of MIL-100 and MIL-101 Iron (III) Carboxylate Nanoparticles Loaded with Pharmaceutically Active Principles: AZTP Encapsulation tests were performed with other medicaments, such as Cidofovir (CDV; antiviral) or azidothymidine triphosphate (AZTP; retroviral). Given the dimensions of these molecules, the porous iron carboxylates of rigid structure MIL-100 and MIL-101 were chosen since they have 25-34 Å cages.

a) Encapsulation and Release of AZTP

Preliminary study of encapsulation of AZTTP in MIL-100 and MIL-101 nanoparticles: the encapsulation of the retroviral agent azidothymidine triphosphate (AZTP) was performed in porous iron carboxylates of rigid structure MIL-100 (500 nm nanoparticles) and MIL-101 (500 nm nanoparticles), which have cages of free sizes between 25 and 34 Å.
Insertion of the medicament was performed by immersing 2.5 mg of the dehydrated solids (100° C./12 hours) in aqueous solutions containing, respectively 50, 100, 250 and 500 µg of AZTP in 500 µl and 50 µg/50 µl with stirring for one hour. After adsorption of the medicament, the solid loaded with medicament is recovered by centrifugation at 5000 rpm for 15 minutes and dried under vacuum for three days. Quantification of the content of adsorbed medicament was performed by radioactive counting ($^3$H-AZTP).

It is observed that the use of solutions more concentrated with medicament leads to an increase in loading of the material with active principle, up to a maximum of 9% by weight (a record!!) of medicament in the MIL-100 nanoparticles. Considering that the solid MIL-101 has a pore volume that is virtually double (2 cm$^3$/g vs 1.2 cm$^3$/g), the latter is expected to have much larger capacities. For equal concentrations but with a higher ratio of AZTP/material initially introduced by weight, the active principle load increases. In addition, the encapsulation efficacy is excellent.

The encapsulation of AZTP may be optimized in the following manner:
  Increasing the concentration of the starting AZTP solution
  Several impregnation cycles
  Different impregnation times
  Use of solids surface-modified with PEG
  Use of different solids with a larger capacity (MIL-101 biphenyl, MIL-88D modified with different organic groups) and of hybrid solids with modified ligands (NH$_2$, Cl, NO$_2$, COOH, etc.) to optimize the medicament-solid interactions.

b) Encapsulation of AZTTP in PEGylated or Non-PEGylated MIL-100 Nanoparticles

MIL-100 nanoparticles were synthesized via the microwave route (CEM microwave) starting with a solution of 9.7 g of iron nitrate hexahydrate (Aldrich, 97%), 3.38 g of 1,3,5-benzenetricarboxylic acid (1,3,5-BTC, Aldrich, 99%) and 40 g of distilled water at 180° C. for 30 minutes (power 600 W). The particle size measured by light scattering is 400 nm.

The PEGylated MIL-100 nanoparticles were obtained by modifying the surface of the particles mentioned in Example 24. 30 mg of MIL-100 were suspended in 3 ml of an aqueous solution of 10 mg of amino-terminal polyethylene glycol (PEG-NH$_2$ 5000 g/mol, Aldrich, 97%) at 30° C. for three hours with stirring. These nanoparticles were recovered by centrifugation (10 000 rpm/10 minutes) and washed with distilled water.

The amount of PEG at the surface was determined via the method of Baleux and Champertier, based on the formation of a complex stained with iodine-iodide on the PEG, which is selectively measured by spectrophotometry at 500 nm. (The amount of PEG is 19% by mass and the particle size after PEGylation increased to 800 nm.) On the other hand, the observation of PEGylated and non-PEGylated nanoparticles by scanning electron microscopy (SEM) shows nanoparticles of 150 nm in both cases. This difference may be due to particulate aggregation phenomena.

The adsorption of AZT-TP (azidothymidine triphosphate; 1-[(2R,4S,5S)-4-azido-5-(hydroxymethyl)tetrahydrofuran-2-yl]-5-methylpyrimidine-2,4(1H,3H)-dione, Moravek) is studied with the PEGylated or non-PEGylated MIL-100 nanoparticles, using tritium-labeled AZT-TP ($^3$H-AZTP; Moravek; 3.8 Ci/mmol, 1 mCi/ml, 133.4 µg/ml, 250 µl).

The experiments are performed in quadruplicate, by suspending 2.5 mg of the solid MIL-100 dried beforehand (150° C./night) in 500 µl of an aqueous solution of 1 mg/ml of AZT-TP (50 µl of $^3$H-AZT-TP+3 ml of AZT-TP) at room temperature with stirring for 16 hours.

The nanoparticles encapsulating the AZT-TP are recovered by centrifugation (10 000 rpm/10 minutes, at room temperature) and dried under vacuum for three days. The radioactivity in the supernatant is determined by counting the radioactivity (Beckman Coulter LS 6500 multipurpose scintillation counter) and the AZT-TP adsorbed into the materials is quantified by the difference with the radioactivity of the stock solution.

The nanoparticles are degraded under acidic conditions (2.5 mg of nanoparticles are degraded in 1 ml of 5M HCl at 50° C. overnight) and the radioactivity is determined.

The amount of AZT-TP adsorbed into the materials is 8% in MIL-100 and 5% by mass in the PEGylated MIL-100.

c) Controlled Release of AZTTP from PEGylated MIL-100 and MIL-100 Nanoparticles

The release of AZT-TP is performed by suspending 2.5 mg of nanoparticles (2.5 mg of nanoparticles+8 wt % of AZT-TP for MIL-100 and 5 wt % for MIL-100 covered with PEG) at 37° C. in 1 ml of pH 7.4 phosphate buffer (Aldrich). The suspensions are maintained under two-dimensional stirring for the various incubation times (30 minutes, 2.5 hours, 5 hours, 7.5 hours, 24 hours, 48 hours, 72 hours, 96 hours, 168 hours, 240 hours). Next, the suspensions were centrifuged (10 000 rpm, 10 minutes) and 0.5 ml of supernatant was taken and replaced with fresh PBS (phosphate-buffered saline). The amount of AZT-TP released is determined by measuring the radioactivity in the supernatents (release medium).

The nanoparticles not covered with PEG release their active principle content gradually over two days, more slowly than those covered with PEG. This might be explained by a different location of AZT-TP within the nanoparticles. It is probable that the PEG "brush" at the surface sterically prevents the active principle from penetrating more deeply into the nanoparticles. This active principle, located in the upper layers of the material, is released more quickly.

Example 16: Formulation of Iron(III) Carboxylate Nanoparticles Loaded with Pharmaceutically Active Principles: Cidofovir a) Encapsulation and Release of Cidofovir (CDV)

The adsorption of Cidofovir (L-(S)-1-(3-hydroxy-2-phosphonylmethoxypropyl)cytosine, CDV, Moravek) was studied in MIL-88A, MIL-89, MIL-100 and MIL-101 nanoparticles, using $^{14}$C-labeled CDV ($^{14}$C-CDV).

The experiments are performed in triplicate, by suspending 2 mg of the material dehydrated beforehand (150° C./night for MIL-100 and 100° C./night for the rest) in 1 ml of an aqueous solution of 400 µg/ml of CDV (50 µl of $^{14}$C-CDV+ 3 ml of CDV) at room temperature with stirring for 16 hours.

The CDV-encapsulating nanoparticles are recovered by centrifugation (10 000 rpm/10 minutes, room temperature) and dried under vacuum for three days. The radioactivity in the supernatent is determined by counting the radioactivity (Beckman Coulter LS 6500 multipurpose scintillation counter) and the CDV adsorbed into the materials is quantified by the difference with the radioactivity of the stock solution.

The nanoparticles are degraded under acidic conditions (2 mg of nanoparticles are degraded in 1 ml of 5M HCl at 50° C. overnight) and the radioactivity is determined.

The amount of AZT-TP adsorbed into the materials is 8% in MIL-100 and 5% by mass in the PEGylated MIL-100.

TABLE 21

Encapsulation of CDV in the various iron carboxylate nanoparticles

| Solid | % CDV | % efficacy |
|---|---|---|
| MIL-88A | 2.6 | 12.2 |
| MIL-100 | 17.6 | 83.8 |
| MIL-101 | 2.8 | 14.0 |
| MIL-89 | 14.1 | 81.1 |

The very large capacities range between 3% and 18%. Thus, the encapsulation efficacies are very high (more than 80% for the solids MIL-100 and MIL-89).

b) Release of CDV by MIL-88A, MIL-100, MIL-101 and MIL-89 Nanoparticles

The release of CDV was performed by suspending 2 mg of nanoparticles (2 g of nanoparticles+wt % of CDV) at 37° C. in 1 ml of pH 7.4 phosphate buffer (Aldrich). The suspensions were maintained under two-dimensional stirring for the various incubation times. The suspensions were then centrifuged (10 000 rpm, 10 minutes) and 0.5 ml of supernatent was taken and replaced with fresh PBS. The amount of AZT-TP released was determined by measuring the radioactivity in the supernatents (release medium).

The encapsulation of Cidofovir may be optimized by modifying the following parameters:

Increasing the concentration of the starting solution

Several impregnation cycles

Various impregnation times

Use of various solids with greater capacity (MIL-101 biphenyl, MIL-88D modified with various organic groups) and of hybrid solids with modified ligands (NH2, Cl, NO2, CH3, COOH, etc.) to optimize the medicament-solid, interactions.

As a function of the encapsulation results, we will use solid nanoparticles surface-modified with PEG for the encapsulation tests.

Release tests will be performed in a physiological medium (phosphate buffer, NaCl, etc.).

Example 17: Encapsulation of Other Pharmaceutically Active Principles a) Formulation of Iron(III) Carboxylates Loaded with Paclitaxel

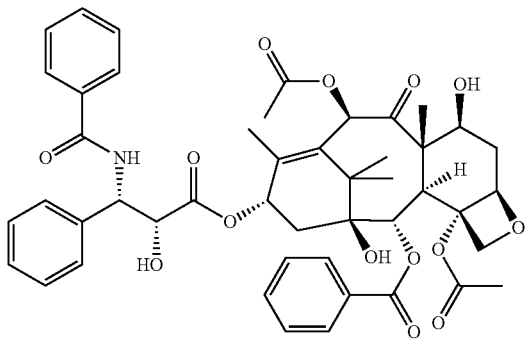

Paclitaxel, sold under the name Taxol, is soluble in ethanol and in DMSO (about 50 g/L).

It may be encapsulated by impregnating the nanoparticles in DMSO solutions of concentrations 20 to 50 g/L, according to a protocol similar to that used for encapsulating busulfan. The only difference is that solutions of paclitaxel in DMSO or ethanol are used.

b) Formulation of Iron(III) Carboxylates Loaded with Docetaxel

Docetaxel is a paclitaxel analog, of similar structure and activity, but it differs therefrom especially in its toxicity and its antitumor efficacy. Sold under the name Taxotere (it is a perfusion), this active principle has side effects (risk of water retention, ascites, pleural or pericardial effusion, cutaneous reactions, alopecia, etc.). Thus, its encapsulation in nanoparticles and its release in a tumor would be a major advance.

Docetaxel may also be encapsulated by impregnation with DMSO solutions or ethanol by using:
- different impregnation times
- several impregnation cycles
- different solids with greater capacity (MIL-101 (terephthalate), MIL-101 (2,6-naphthalene dicarboxylate), MIL-101 (4,4-biphenyl dicarboxylate) and/or MIL-88D modified with different organic groups) and of hybrid solids with modified ligands (CH3, COOH, etc.) to optimize the medicament-solid interactions. ["MIL-101 (terephthalate)" refers to the MOF solid of MIL-101 phase in which the ligand L is a terephthalate ligand. A similar convention is used for the other abovementioned MIL-101 solids].

As a function of the encapsulation results, we will use solid nanoparticles surface-modified with PEG for encapsulation tests.

c) Formulation of Iron(III) Carboxylates Loaded with Gemcitabine

Gemcitabine (dFdC) is a deoxycytidine analog. It is a specific antimetabolite of the S phase of the cell cycle (DNA synthesis phase). Gemcitabine is metabolized in cells with nucleoside kinases into nucleoside diphosphate (dFdCDP) and triphosphate (dFdCTP). These are the active metabolites.

Gemcitabine is water soluble. Thus, its encapsulation may be performed according to a protocol identical to the encapsulation of AZT triphosphate (impregnation in aqueous solutions of active principle).

The encapsulation of gemcitabine may be optimized by modifying the following parameters:
- Increasing the concentration of the starting solution
- Several impregnation cycles
- Different impregnation times
- Use of different solids with a larger capacity (MIL-101 biphenyl, MIL-88D modified with different organic groups) and of hybrid solids with modified ligands (NH2, Cl, NO2, CH3, COOH, etc.) to optimize the medicament-solid interactions.
- Depending on the encapsulation results, we will use solid nanoparticles surface-modified with PEG for encapsulation tests.
- Release tests will be performed in a physiological medium (phosphate buffer, NACl, etc.).

Example 18: Formulation of Iron(III) Carboxylates Loaded with Cosmetic Compound of Interest The encapsulation of various molecules of cosmetic interest is performed in porous iron carboxylates of rigid structure MIL-100 and of flexible structure MIL-53. The molecules chosen for the examples are ascorbic acid for its free-radical-scavenging properties, caffeine for its liporegulating activity, and urea as a moisturizer. The process described for the encapsulation of benzophenone is also applicable to these compounds. Finally, as for benzophenone-3 (UV-screening agent), of hydrophobic nature, benzophenone-4 of hydrophilic nature may also be encapsulated.

For the insertion of cosmetics, the dehydrated solids (100 or 150° C./12 hours) or non-dehydrated solids are placed in aqueous suspensions or in alcohol in the presence of variable amounts of cosmetics, the whole being stirred for different times. After adsorption, the solid loaded with cosmetics is recovered by centrifugation at 5000 rpm for 15 minutes and dried in air. Quantification of the amount of cosmetic adsorbed is performed by elemental analysis and TGA.

For cosmetic purposes, nanoparticles covered with hyaluronic acid and encapsulating active principles are particularly advantageous. Specifically, hyaluronic acid is a natural constituent of the dermis and plays an important role in the hydration and elasticity of the skin. As this substance diminishes with age, our skin becomes dry and wrinkled. About 56% of the hyaluronic acid contained in the body is found in the skin.

Coating MOFs with this polymer might give them bioadhesive properties for the skin.

a) Encapsulation of benzophenone-3

Benzophenone-3(2-hydroxy-4-methoxybenzophenone) (BZ3) is a very sparingly water-soluble solid (0.0037 g/l (20° C.)):

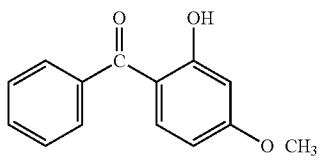

It is an anti-UV sunscreen. Benzophenone-3 is used in antisun creams and in cosmetic products as an "antiaging" substance. It is also used as a protector for active substances contained in cosmetics: it can prevent the UV-induced degradation of these substances, such as fragrances or dyes. This substance is a known allergen, with very strong allergenic power. It may be photosensitizing. Its encapsulation would be useful in order to avoid direct contact with the skin.

The experimental protocol used is as follows: dried nanoparticles (MIL-53(Fe), mean diameter 1.1 microns) were dispersed in 10 ml of a solution containing 10 micrograms of BZ3 per ml, so as to obtain final particle concentrations equal to 1 and 0.5 mg/ml. The low concentration of BZ3 chosen here is explained by its poor solubility in water. The compound MIL-53(Fe) also has very good affinity for aromatic molecules, which justifies the choice of this material for encapsulating benzophenone.

This BZ3 solution was obtained from a solution of BZ3 in DMSO (1 g/l). One ml of this solution was taken and then placed in 100 ml of MilliQ water.

The nanoparticles were incubated for 12 hours at room temperature and then recovered by ultracentrifugation (30 000 rpm, 30 minutes). The supernatent was taken up and then assayed (UV spectrophotometry, wavelength of 298 nm), thus making it possible to determine the amount not encapsulated. The encapsulated amount was determined by difference with the amount of BZ3 initially introduced. The experiments were performed in triplicate.

TABLE 22

Load contents obtained

| Particle concentration (mg/ml) | Encapsulation yield (mass %) | Load (mass %) |
|---|---|---|
| 1 | 76 ± 3 | 0.76 |
| 0.5 | 74 ± 3 | 1.49 |

The encapsulation yields (% encapsulated relative to the amount of BZ3 introduced) are satisfying (74-76%). On the other hand, the low loads are explained by the small amount of BZ3 introduced compared with the amount of particles. We find, nevertheless, that the loading increases when the introduced concentration of particles (relative to BZ3) decreases. Consequently, given that the aqueous solution of BZ3 used was sparingly concentrated, it may be entirely envisioned to considerably improve the loading of the particles with BZ3 by impregnating therein a suitable organic solvent in which the solubility of BZ3 will be markedly higher.

b) Encapsulation of benzophenone-4

Benzophenone-4(2-hydroxy-4-methoxybenzophenone-5-sulfonic acid) (BZ4) is a solid that is very soluble in water (100 mg/ml (20° C.)):

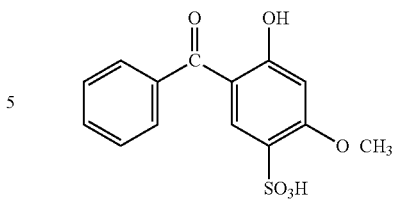

It is an anti-UVA and anti-UVB sunscreen, particularly used when a water-soluble formulation is demanded. Benzophenone-4 is used in antisun creams and cosmetic products as an "anti-aging" substance. It is also used as a protective agent for active substances contained in cosmetics: it can prevent the UV-induced degradation of these substances, such as fragrances or dyes. However, it may lead to immune reactions, in the form of itching, a burning sensation, desquamation, urticaria, and skin blisters, or a severe respiratory reaction. Its encapsulation would make it possible to maintain its activity while avoiding direct contact with the skin.

c) Encapsulation of Urea

Urea is an active substance of natural origin, which is found in all organs, tissues and fluids of the human body. It has very high solubility in water (1.08 g/ml (20° C.)).

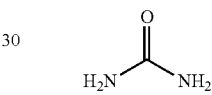

It is an important moisturizer of the horny layer. It has various effects:
It soothes itching, which is a major advantage in the case of infantile neurodermatitis.
It moisturizes the horny layer.
It has a desquamating effect and it normalizes cell division.
It has antibacterial properties, preventing overinfections, in particular in the case of chronic eczema.
It promotes the penetration of other medicinal substances simultaneously applied to the skin, for instance glucocorticoids. Thus, the dosage of medicaments may be reduced without reducing their efficacy and while thus limiting the side effects.

d) Encapsulation of Caffeine

Caffeine is a lipolytic agent known for its slimming properties. Its liporeducing action is powerful and dose-dependent. Caffeine is the most active form, since it is directly assimilable by the cell. However, caffeine salts are the ones most used in practice, since they are easier to incorporate into a cream.

It has good solubility in water (22 mg/ml (20° C.)).

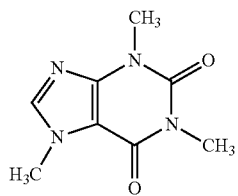

e) Experimental Encapsulation Protocols 150 mg of dried MIL-53(Fe) nanoparticles (mean diameter 1.1 microns; dehydrated at 150° C./8 hours) and MIL-100(Fe) nanoparticles (mean diameter 0.5 microns; dehydrated at 100° C./8 hours) were dispersed in 10 ml of aqueous solutions containing different cosmetic agents (concentrations close to saturation; see the table below), the whole being stirred for 2 hours or 3 days at room temperature. The particles are then recovered by centrifugation (20° C., 5000 rpm, 15 minutes).

The solids loaded with cosmetics are first characterized by X-ray powder diffraction (XRD). The mass content of cosmetic encapsulated in the porous solid is estimated by thermogravimetric analysis (TGA) and elemental analysis.

TABLE 23

Quantification of cosmetic in the solids MIL-53 and MIL-100 by TGA (FIGS. 4 and 5) and elemental analysis

| Material | Cosmetic | Concentration (mg/ml) | Impregnation time (h) | TGA |
|---|---|---|---|---|
| MIL-100 | C | 22 | 72 | 24.2 |
| | U | 500 | 72 | 69.2 |
| | BZ4 | 10 | 72 | 13.7 |
| | BZ4 | 10 | 2 | 15.2 |
| MIL-53 | C | 22 | 72 | 23.1 |
| | U | 500 | 72 | 63.5 |
| | BZ4 | 10 | 72 | 5.0 |
| | BZ4 | 10 | 2 | — |
| | BZ4 (EtOH) | 10 | 2 | 1.0 |
| MIL-88 | C | 22 | 72 | 43.6 |
| MIL-53 2COOH | C | 22 | 72 | 9.0 |
| MIL-53 2OH | C | 22 | 72 | 30.2 |
| MIL-53 NH2 | C | 22 | 72 | 25.4 |

(C: caffeine; U: urea; BZ4: benzophenone-4)

The concentration of the starting solutions is very close to saturation to force the insertion of the cosmetics into the pores and to avoid shifting the equilibrium toward a release in liquid phase (see the above table).

The cosmetic encapsulation capacity is very high in all cases, up to 60-70% for urea, which is a very polar small molecule. For caffeine, a larger molecule, slightly lower cosmetic insertion is observed, around 25-40% by mass. This molecule may interact with the polar parts (metal) and apolar parts (ligand) of the hybrid solids.

Finally, benzophenone-4 is encapsulated well into MIL-100 (up to 15%), but it shows much lower insertion into the solid MIL-53 (<5%) in agreement with dimensions close to the maximum size of the pores of this compound.

Conservation of the ordered crystal structure is verified in all the solids of rigid structure after encapsulation by XRD.

The release of caffeine from the solids of different structure (MIL-53, MIL-88 and MIL-100) and in solids based on modified ligands $MIL_{53-2}COOH$, $MIL_{53-2}OH$ and MIL53_NH2 was performed by suspending 50 mg of material containing caffeine in 5 ml of a phosphate-buffered saline PBS solution (Aldrich) pH 7.4 at 37° C. with stirring.

These suspensions are centrifuged (10 000 rpm, 10 minutes at 20° C.) and 1 ml of supernatant is taken and replaced with fresh PBS in the various release times. The concentration of caffeine released into the medium was determined by UV-visible spectroscopy at 254 nm.

It may be observed that it is possible to modify the dose administered over time as a function of the structure and composition of the material.

Example 19: Encapsulation of Fluorescent Molecules

Figure 32:
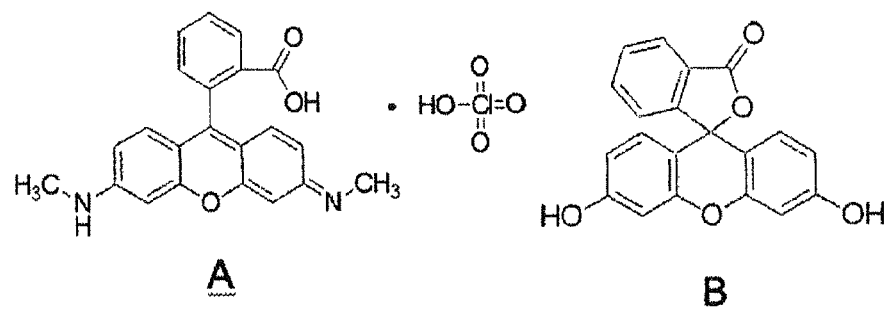
FIG. 32 represents rhodamine 116 perchlorate (A) and fluorescein (B) molecules.
Figure 33:
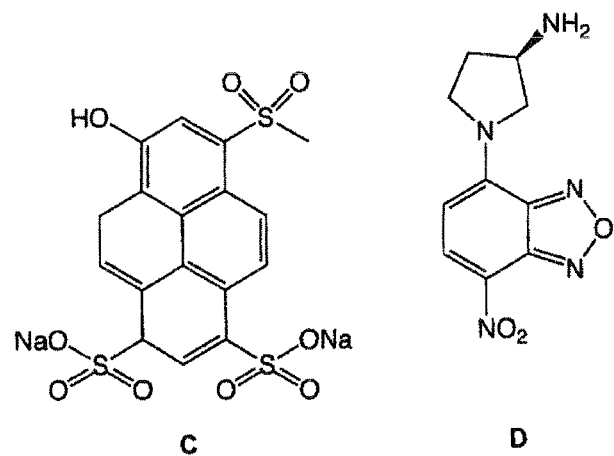
FIG. 33 represents 8-hydroxypyrene-1,3,6-trisulfonic acid (C) and (R)-(−)-4-(3-aminopyrrolidino)-7-nitrobenzofurazan (D) molecules.

Fluorescent molecules such as rhodamine perchlorate (A), fluorescein (B), the sodium salt of 8-hydroxypyrene-1,3,6-trisulfonic acid (C) or (R)-(–)-4-(3-aminopyrrolidino)-7-nitrobenzofurazan (D) were encapsulated in the solid MIL-101-$NH_2$ according to the protocol described below. These molecules are represented in FIGS. 32 and 33.

Procedure:

200 mg of solid rigid iron aminoterephthalate MIL-101-$NH_2$ (synthesized according to the microwave method described in Example 7) are suspended in 10 ml of a 2 mg/ml solution of fluorescent molecule in ethanol:

A: rhodamine 116 perchlorate (R116, Aldrich),

B: fluorescein (Aldrich),

C: trisodium salt of 8-hydroxypyrene-1,3,6-trisulfonic acid (PSO3, Aldrich, 98%), or D: (R)-(–)-4-(3-aminopyrrolidino)-7-nitrobenzofurazan (APNF, Aldrich, 98%).

The mixture of dissolved solid fluorescent molecule is stirred at room temperature with stirring for 15 hours. The solid loaded with fluorescent molecule is recovered by centrifugation at 10 000 rpm/10 minutes.

Quantification of the encapsulated fluorescent molecules is performed by TGA and/or elemental analysis. The materials encapsulating the fluorescent molecules are characterized by XRD to verify the conservation of the crystal structure, by FTIR to study the matrix-molecule interactions and by confocal fluorescence microscopy to determine the presence of fluorescence in the pores or at the surface (the fluorescence properties of each of these molecules are presented in the following table).

TABLE 24

| Fluorescence properties | | | |
|---|---|---|---|
| Fluorescent molecule | λ excitation (nm) | λ emission (nm) | Solvent |
| A (rhodamine 116) | 516 | 540 | ethanol |
| B fluorescein | 490 | 514 | 0.1M tris pH 8.0 |
| C (PSO3) | 460 | 510 | 0.1M tris pH 8.0 |
| D (APNF) | 490 | 535 | acetonitrile |

The in vivo imaging properties (bioluminescence, fluorescence) may be studied according to protocols known to those skilled in the art. Reference may be made, for example, to the publication by Kathryn E. Luker et al., Antiviral Research, Volume 78, Issue 3, June 2008, pages 179-187.

In addition, the same protocol is applicable to the encapsulation of molecules A, B, C and D in the case of the iron dimethyl-4,4'-biphenyldicarboxylate MOF solid (synthesized according to the solvothermal method described in Example 3).

Example 20: Encapsulation of Fluoro Molecules 1-(Pentafluoropropionyl)imidazole

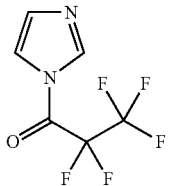 [SMILES: O=C(n1ccnc1)C(F)(F)C(F)(F)F]

200 mg of rigid iron trimesate MIL-100 (synthesized via the solvothermal method described previously) are dehydrated beforehand at 150° C. overnight and are suspended in 10 ml of a 2 mg/ml solution of perfluoro-pentanoic acid (Aldrich, 97%) or 1-(pentafluoro-propionyl)imidazole (Aldrich, 98%) in ethanol with stirring at room temperature for 15 hours. The solid is recovered by centrifugation at 10 000 rpm/10 minutes.

Quantification of the encapsulated fluoro molecules is performed by TGA and/or elemental analysis. The materials encapsulating the fluorescent molecules are characterized by XRD to verify the conservation of the crystal structure, by FTIR and 19F NMR to study the matrix-molecule interactions.

Example 21: Encapsulation of Urea by Sublimation

This protocol is especially applicable to molecules to be encapsulated of low evaporation temperature, such as urea, enabling simpler sublimation.

In this case, the reduced size of the urea molecule allows its encapsulation into flexible solid pores MIL-53 and rigid solid pores MIL-100 (syntheses described previously).

Figure 31:
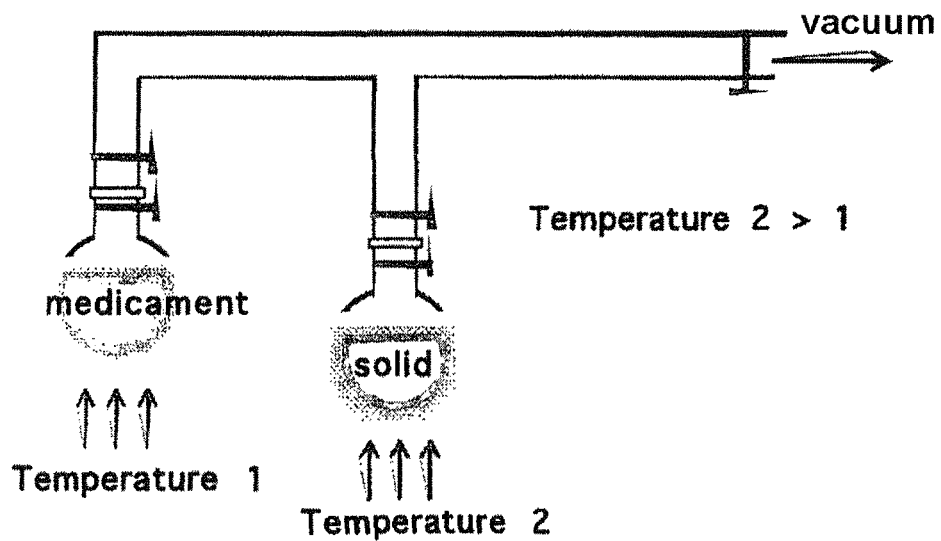
FIG. 31 represents the experimental setup for encapsulation by sublimation (example 21).

The experimental setup used for inserting PA by sublimation is presented in FIG. 31.

The sublimation encapsulation protocol is described in the following steps:
1. The porous solid is first dehydrated at 150° C. under vacuum for 12 hours (the flask valve containing the medicament is closed and the flask valve containing the solid is open to the vacuum).
2. The urea is heated under vacuum to sublimate it at the sublimation temperature T1 under vacuum of urea. The MOF solid is itself heated to the temperature T2, 5° C. higher than T1. The whole circuit is also heated to avoid recrystallization of the urea (the "medicament" flask valve is opened to the vacuum and the "solid" valve is closed).
3. The "solid" valve is then opened to place the sublimated medicament and the dehydrated solid in contact so as to achieve encapsulation of the medicament in the material.
5. The valve of the flask containing the "solid" is then closed.
6. Nitrogen gas is introduced into the solid flask.
7. The solid encapsulating the urea is then recovered.

VI. Surface-Modified Nanoparticles

Example 22: Formulation of Iron(III) Carboxylates Surface-Modified with Chitosan The surface modification of nanoparticles with chitosan makes it possible to envision various routes of administration of the nanoparticles by virtue of the specific bioadhesion properties of this polymer.

In this example, surface modification is performed during the synthesis of the material MIL-88A.

a) Preparation of Surface-Modified Nanoparticles

To a solution of $FeCl_3.6H_2O$ (1 mmol, 270 mg; Alfa Aesar, 98%) and fumaric acid (1 mmol, 116 mg; Acros, 99%) in 5 mL distilled water, in a 23 mL Teflon bomb, were added 7 mg of the surface-modifying agent, the modified chitosan, are added to a solution of $FeCl_3.6H_2O$ (1 mmol, 270 mg; Alfa Aesar, 98%) and fumaric acid (1 mmol, 116 mg; Acros, 99%) in 5 ml of distilled water, in a 23 ml Teflon bomb. Two types of chitosan modified with alkyl chains (C12, lauryl) were used; one with modification of 2% of alkyl chains (Q25) and the other modified with 7% (Q100).

For complete dissolution of the chitosan, the solution is stirred for 45 minutes.

The Teflon bomb is placed in a hermetically sealed metallic body and heated in an oven at 80° C. for 12 hours.

The solid obtained is recovered by centrifugation at 5000 rpm for 10 minutes and washed with distilled water and acetone.

b) Analysis and Characterization

The size of the particles obtained is measured with a Malvern Zetasizer Nano series—Nano-ZS Z potential machine; model Zen 3600; serial No. 500180; UK, observing a size of 2.64 and 0.91 microns for MIL-88A-Q 25 and MIL-88A-Q 100, respectively.

The X-ray diffraction (XRD) diagrams are collected with a Siemens D5000 X'Pert MDP diffractometer ($\lambda_{Cu}$, $K\alpha_1$, $K\alpha_2$) from 3 to 20° (2θ) with a step size of 0.04° and 2 s per step.

Figure 15:
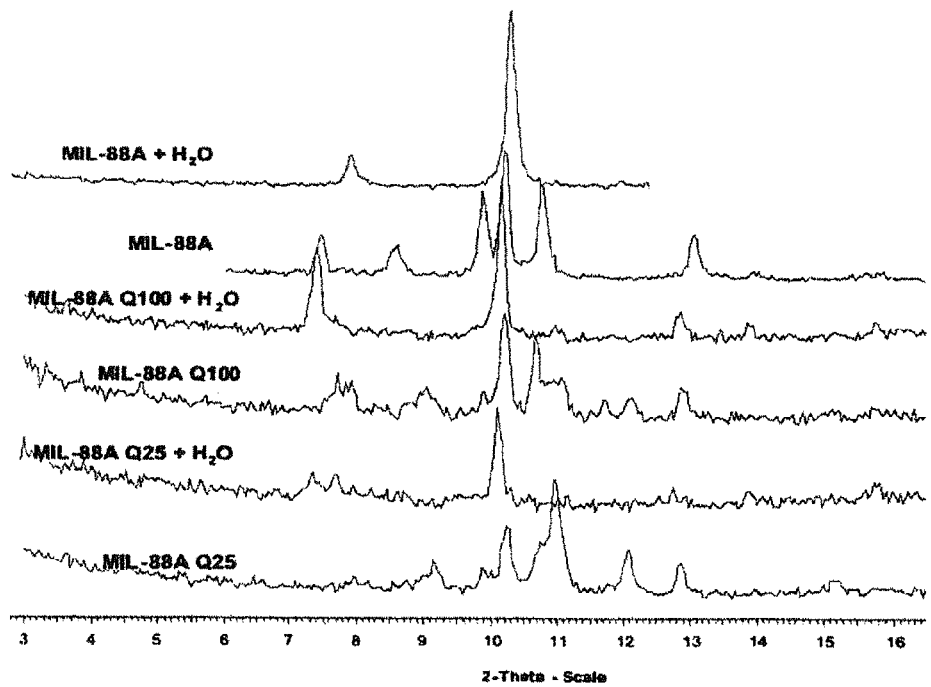
FIG. 15 represents the XRD diagrams of the unmodified material MIL-88A before (MIL88A) and after the addition of one drop of water (MIL88A+$H_2O$); MIL-88A modified with 7% chitosan before (MIL88AQ100) and after the addition of one drop of water (MIL88A Q100+$H_2O$); MIL-88A modified with 2% chitosan before (MIL88AQ25) and after the addition of one drop of water (MIL88A Q125+$H_2O$).

The XRD diagrams presented in FIG. 15 made it possible to verify that the phase obtained is indeed MIL-88A. The flexibility of the material is also verified by XRD by adding a drop of water to the solid.

Figure 16:
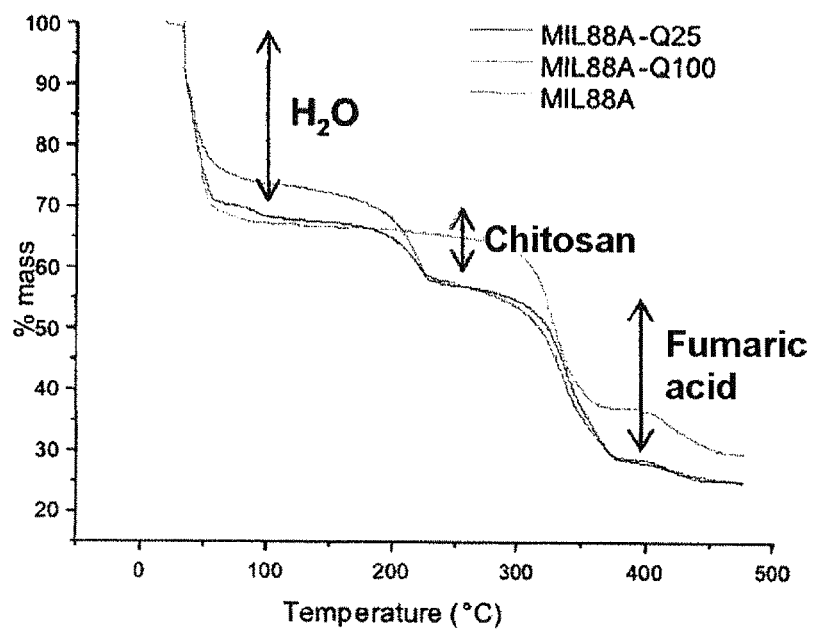
FIG. 16 represents the thermogravimetric analysis of the unmodified material MIL-88A (MIL88A; green), modified with 2% chitosan (MIL-88A-Q25, black) and modified with 7% chitosan (MIL-88A-Q100, red).

The amount of chitosan incorporated into the material is estimated by thermogravimetric analysis (TGA) presented in FIG. 16. The apparatus used is a TGA 2050 TA machine from 25 to 500° C. with a heating ramp of 2° C./minute under a stream of oxygen (100 ml/minute). In the materials, the amount of fumaric acid is indeed about 45% (relative to the dehydrated product). The materials MIL-88A-Q25 and MIL-88A-Q100 contain an amount of chitosan of about 16% and 22% (weight) relative to the dehydrated product, respectively.

Example 23: Formulation of Iron(III) Carboxylates Surface-Modified with Fluorescein-Biotin Dextran In this example, the dextran used is grafted firstly with fluorescein, and secondly with biotin (Dex B FITC 10 000 g/mol, anionic, lysine fixable, Molecular Probes, catalog D7178).

The characteristics of the dextran are as follows: dextran fluorescein and biotin, molecular weight 10 000 g/mol, anionic, capable of binding lysine ("mini-emerald"), batch 36031A, D7178, "Molecular Probes", in vitro detection technology, 1 mol fluorescein/mole, 2 mol biotin/mole.

a) Preparation of Surface-Modified Nanoparticles

Iron 1,3,5-benzenetricarboxylate MIL-100 particles (particle diameter 1.79 microns) were washed with MilliQ water.

Five milligrams of particles were dispersed in 0.5 ml of MilliQ water. 0.5 ml of an aqueous solution of Dex B FITC (5 mg/ml) was added to this suspension. They were incubated at room temperature for 24 hours and then recovered by centrifugation (3800 rpm, 10 minutes). The supernatant was taken up and the pellet (particles) was then resuspended in 0.5 ml of MilliQ water. After centrifuging again, the particles thus washed free of the excess Dex B FITC were placed on a slide for observation under a confocal microscope (excitation 488 nm, emission 515 nm).

b) Analysis and Characterization

Fluorescein allows the detection of the particles using a laser scanning confocal microscope, whereas biotin, which is hydrophobic, allows:
attachment in the core of the particles
functionalization with biotinylated ligands.

Figure 17:
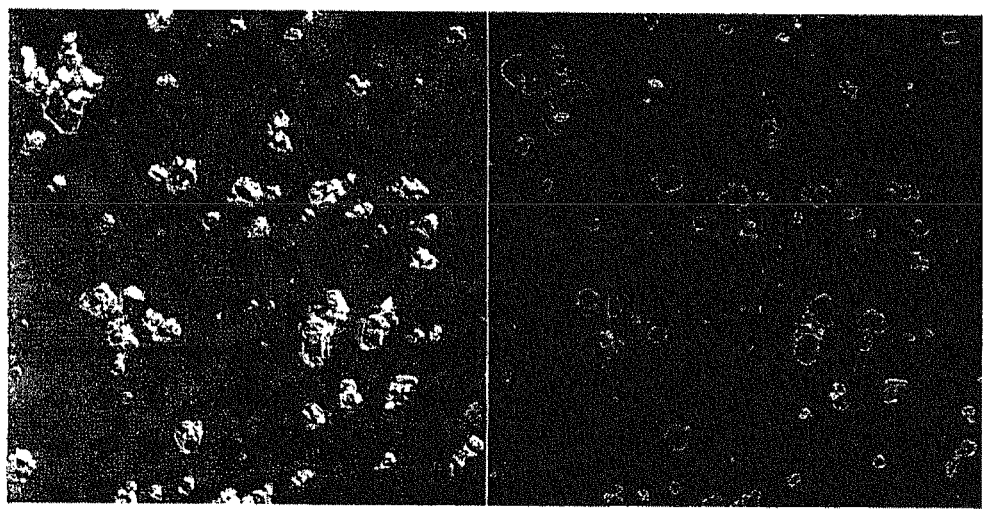
FIG. 17 represents the confocal microscopy images of the material MIL-100(Fe) surface-modified with dextran-fluorescein-biotin.

FIG. 17 shows the optical sections thus obtained. A halo is distinguished around the particles, indicating the presence of dextran (sole fluorescent compound) only at the surface. Specifically, the long polymer chains were not able to penetrate into the core of the particles.

This surface modification method has the advantage of not disturbing the core of the particles (containing the active principles) and of being performed post-synthesis, and thus of offering a variety of possible coatings.

Example 24: Formulation of Iron(III) Carboxylates Surface-Modified with Polyethylene Glycol (PEG)

To minimize the toxicity of busulfan in the liver, the nanoparticles need to be prevented from being directed toward the liver; the best method consists in surface-grafting the hybrid nanoparticles with hydrophilic chains of the poly(ethylene glycol) (PEG) type, so as to reduce their accumulation in this organ. We envision a full study of the in vitro degradation of particles covered or otherwise with PEG, in different media.

The PEG chains may have different end groups so as to graft to the surface of the materials. Thus, the interaction of PEG with the particle surface may be modified by using different types of PEG.
PEG-NH$_2$ (α-t-butyloxycarbonylamino-ω-amino poly (ethylene glycol) (PEG; Boc-NH-PEG-NH2, 5000 MW, Iris Biotech)
PEG-COOH (poly(ethylene glycol) carboxylic acid, Iris Biotech)
PEG-PO$_4$, synthesized in the laboratory according to the following process:

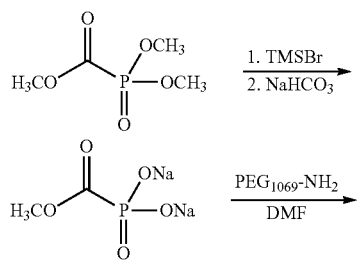

The phosphonate group is attached to the PEG-NH$_2$ via a condensation of amide with an ester bound to a phosphonate group. The sodium salt of the phosphonate was used. Next, the coupling was performed starting with trimethyl phosphonoformate [CAS 31142-23-1] according to the procedure by Robert A. Moss, Hugo Morales-Rojas, Saketh Vijayaraghavan and Jingzhi Tian, J. Am. Chem. Soc., 2004, 126, (35), 10923-10936.

Dissolution of the PEG-NH2 (87.6 mg, M=5400, Iris Biotech GmbH, PEG1069) in 2 ml of DMF (Fluka, 97%) with an excess of disodium methylphosphonoformate (50 mg, M=183.99) was heated at 100° C. for 15 hours with stirring. Next, the solvent was removed under vacuum and the residue suspended in absolute ethanol. The excess phosphonoformate is insoluble, and may thus be removed by filtration. The filtrate is concentrated to give the product (85 mg). $^{31}$P NMR, (D$_2$O), d=1.3 ppm.

The PEGylation may be performed during the synthesis or post-synthesis:

a) Surface Modification with PEG-COOH During the Synthesis

The syntheses of MOFs are performed directly in the presence of monomethoxy PEG monoacid (MeO-PEG-COOH) (Sigma, molar mass 5000 g/mol):

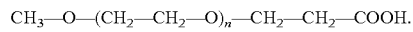

Monomethoxy PEG monoacid is introduced at 3; 8.5 or 13% relative to the total weight of solid used in the synthesis.

Preparation Process:

Iron acetate (1 mmol, synthesized according to synthesis A described in Example 1) and muconic acid (1 mmol; Fluka, 97%) are mixed in 10 ml of methanol (Aldrich, 99.9%). The whole is introduced into a 23 ml Teflon body. The PEG monoacid is then introduced to a height of 3; 8.5 or 13% by mass relative to the total weight of solid. 0.35 ml of 2M sodium hydroxide is optionally added. The solution is stirred for 20 minutes.

The Teflon bomb is placed in a hermetically sealed metallic body and heated in an oven at 100° C. for 12 hours.

The solid obtained is recovered by centrifugation at 5000 rpm for 10 minutes and washed with distilled water and acetone.

Assay.

Assay of the PEG in the iron carboxylates is performed as follows: the particles are totally degraded in acidic medium (5M HCl) so as to release the associated PEG. After neutralizing the solutions obtained (at pH 7) and destroying the nanoparticles with sodium hydroxide, assay of the PEG was performed by UV spectrophotometry (at a wavelength of 500 nm), according to the method described in B. Baleux et al. C.R. Acad. Sciences Paris, series C, 274 (1972) pages 1617-1620 [33]. The main results are collated in the following table.

TABLE 25

Modification of the material MIL-88A with PEG 5000 g/mol

| Addition of aqueous NaOH solution | Mass % of PEG introduced at the start of the synthesis | Mass % of PEG in the nanoparticle composition | Nanoparticle diameter (nm) (measured by light scattering) |
|---|---|---|---|
| — | 3 | 3.8 | 570 |
| yes | 3 | 4.8 | 230 |
| — | 8.5 | 13.4 | 590 |
| yes | 8.5 | 13 | 230 |
| — | 13 | 18.5 | 565 |
| yes | 13 | 18 | 310 |

We find that:
- the addition of sodium hydroxide makes it possible to reduce the size of the nanoparticles
- the mass % of PEG in the nanoparticles is greater than the % of PEG introduced at the start of the synthesis
- it is, remarkably, possible to obtain particles of about 230 nm containing 13% by weight of PEG, which is advantageous for medical applications ("furtivity")

Specifically, the "furtive" nanoparticles described in the literature generally contain less than 10% by mass of PEG, as described in R. Gref et al. *Colloids and Surfaces B: Biointerfaces*, Volume 18, Issues 3-4, October 2000, pages 301-313 [34].

b) Surface Modification of MIL-100 Nanoparticles with PEG Via the Post-Synthesis Method MIL-100 nanoparticles are synthesized via the microwave route (CEM microwave) starting with a solution of 9.7 g of iron nitrate hexahydrate (Aldrich, 97%), 3.38 g of 1,3,5-benzenetricarboxylic acid (1,3,5-BTC, Aldrich, 99%) and 40 g of distilled water at 180° C. for 30 minutes (power 600 W). The particle size measured by light scattering is 400 nm.

The PEGylated MIL-100 nanoparticles are obtained by surface modification of the particles mentioned previously. 30 mg of MIL-100 are suspended in 3 ml of an aqueous solution of 10 mg of amino-terminal polyethylene glycol (PEG-NH2 5000 g/mol, Aldrich, 97%) at 30° C. for 3 hours with stirring. These nanoparticles are recovered by centrifugation (10 000 rpm/10 min) and washed with distilled water.

The amount of surface PEG is determined by the method of Baleux and Champertier, based on the formation of a complex stained with iodine-iodide on the PEG, which is selectively measured by spectrophotometry at 500 nm. The amount of PEG is 19% by mass and the particle size after PEGylation increases to 800 nm. On the other hand, the observation of PEGylated and non-PEGylated nanoparticles by scanning electron microscopy (SEM) shows 150 nm nanoparticles in both cases. This difference is possibly due to particulate aggregation phenomena.

Example 25: Synthesis Via the Ultrasonication Route of Iron(III) Carboxylates Surface-Modified with Polyethylene Glycol (PEG)

Synthesis via the ultrasonication route of solid MIL-88A nanoparticles surface-modified with PEG is based on the procedure of Example 8, and was performed at different reaction times (30, 60, 90 and 120 minutes).

In the examples that follow, two procedures were performed:
a) in the first procedure, the PEG is added 15 minutes before the end of the synthesis
b) in the second procedure, the PEG is added at the start of the synthesis (t=0 min).

For each of the syntheses below, aqueous solutions of iron(III) chloride (2.7 mg/ml) and of fumaric acid (1.16 mg/ml) are prepared as described in Example 8 (Table 10).

a) Synthesis 1

5 ml of iron(III) chloride solution (2.7 mg/ml) and 5 ml of fumaric acid solution (1.16 mg/ml) are added to each of the eight 20 ml flasks:
- four flasks serve as control in which the reactions are performed for the four synthesis times: 30, 60, 90 and 120 minutes,
- in the other four flasks, 5 mg of PEG are added 15 minutes before the end of each of the syntheses, lasting 30, 60, 90 and 120 minutes (the end of a synthesis corresponds to removal from the ultrasonication bath).

The eight flasks are placed at the same time in a sonication bath at 0° C. for the corresponding times t (30, 60, 90 and 120 minutes).

After the synthesis, a volume of 0.1 ml of solution is taken from each flask in order to determine the particle size by light scattering using a Dynamic Light Scattering machine (DLS, Nanosizer). The rest of the solution is then centrifuged at 10 000 rpm at 0° C. for 15 minutes in order to separate the supernatant from the solid formed. The supernatant is removed using a Pasteur pipette and the pellet recovered is placed under a fume cupboard at room temperature.

Figure 29:
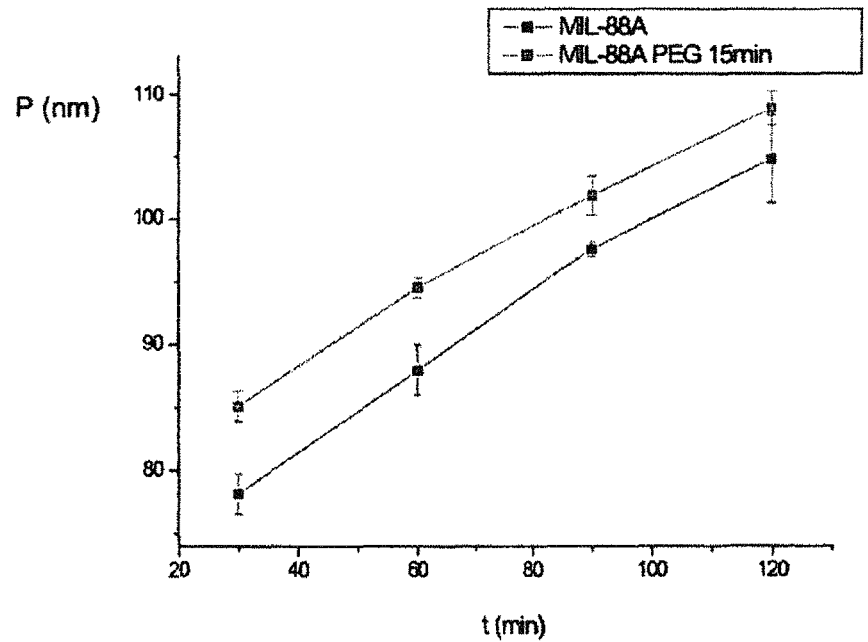
FIG. 29 represents the change in particle size (P in nm) as a function of time (t in min) for synthesis 1 via the ultrasonication route (0° C. in the presence or absence of PEG, added 15 minutes after start of the synthesis) (example 25).

The change in particle size (P in nm) as a function of time (t in minutes) is represented in FIG. 29. The presence of PEG 15 minutes before the end of the synthesis produces an increase in particle size of about 5 nm, which may be due to the thickness of the PEG layer (5000 Da).

b) Synthesis 2

5 ml of iron(III) chloride solution (2.7 mg/ml) and 5 ml of fumaric acid solution (1.16 mg/ml) are added to each of the eight 20 ml flasks:
- four flasks serve as control in which the reactions are performed for the four synthesis times: 30, 60, 90 and 120 minutes,
- in the other four flasks, 5 mg of PEG are added at the start of each of the syntheses, lasting 30, 60, 90 and 120 minutes.

The eight flasks are placed at the same time in a sonication bath at 0° C., for the corresponding times t (30, 60, 90 and 120 minutes).

After the synthesis, a volume of 0.1 ml of solution is taken from each flask so as to determine the particle size by light scattering using a Dynamic Light Scattering machine (DLS, Nanosizer). The rest of the solution is then centrifuged at 10 000 rpm at 0° C. for 15 minutes so as to separate the supernatant from the solid formed. The supernatant is removed using a Pasteur pipette and the pellet recovered is placed in a fume cupboard at room temperature.

Figure 30:
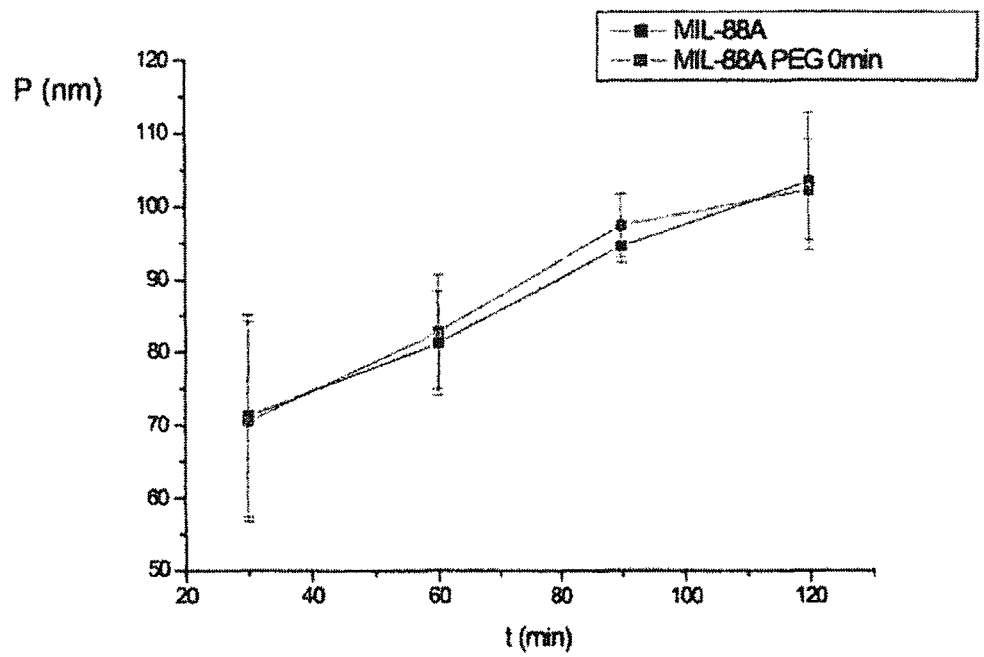
FIG. 30 represents the change in particle size (P in nm) as a function of time (t in min) for synthesis 2 via the ultrasonication route (0° C. in the presence or absence of PEG, added at time t=0) (example 25).

The change in particle size (P in nm) as a function of time (t in minutes) is represented in FIG. 30. This figure shows that there is no significant variation after the addition of PEG at the initial synthesis time.

Whether it is in the presence or absence of PEG at the initial synthesis time, it is possible to observe by XRD a shoulder at 11°, characteristic of the MIL-88A phase, which appears to increase in intensity with the synthesis time.

c) Conclusion of the Study

The aim of this study was to optimize the particle size, which must be less than 200 nm, so as to be able to make the particles compatible with intravenous administration. The results obtained are satisfactory since the particle diameters obtained are less than 200 nm (with verification of the crystal structures of MIL-88A type in most solids). Furthermore, although the yields are lower than those obtained via the solvothermal route or via microwave, they may be considered as acceptable (table below).

TABLE 26

Ultrasonication-route synthesis yields

| Time (min) | Yield (%) | | | |
|---|---|---|---|---|
| | Control | AcH | PEG t = 0 | PEG tf-15 min |
| 30 | 24 | 13.4 | 31.4 | 20.1 |
| 60 | 27.2 | 15 | 29.4 | Not measured |
| 90 | 35.6 | 14 | 24 | 28.3 |
| 120 | 35.1 | 19.1 | 32 | 41.2 |

It is possible to observe that the particle size increases as a function of the synthesis time.

Similarly, PEGylation at t=0 min results in smaller particle diameters than PEGylation at t=f-15 min, probably due to the fact that the crystal growth is stopped earlier.

Example 26: Formulation of MOF Solids Surface-Modified with Polyethylene Glycol (PEG) and Folic Acid (FA)

Folic Acid:

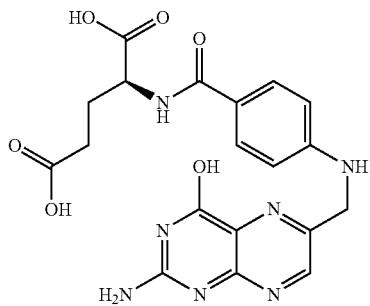 [SMILES: Nc1nc(O)c2nc(CNc3ccc(C(=O)N[C@@H](CCC(=O)O)C(=O)O)cc3)cnc2n1]

a) Synthesis 1: Modification of the Surface Area after Formulation of the Nanoparticles Surface Modification with PEG:

100 mg of MIL-100, MIL-88, MIL-53 or MIL-101 nanoparticles (dehydrated beforehand at 100° C./night) are dispersed by sonication in 100 ml of solution containing 17.9 mM of 2-(methoxy(polyethyleneoxy)-propyl)trimethoxysilane in anhydrous toluene. The mixture is subjected to ultrasound at 60° C. for 4 hours, under a stream of inert gas (nitrogen). The resulting colloidal suspension, containing the nanoparticles surface-modified with PEG, is washed twice with ethanol and twice with a 20 mM sodium citrate solution (pH 8.0) and resuspended finally in water.

Modification of the Surface with PEG and FA:

FA was attached to the nanoparticles by means of a difunctional spacer, silane-PEG-trifluoroethyl ester (TFEE) synthesized according to a method described in the literature by Kohler N. et al., *J Am Chem Soc* 2004; 126: 7206-7211.

100 mg of nanoparticles are covered with PEG-TFEE according to the same method as described above, using silane-PEG-TFEE in place of 2-methoxy(polyethyleneoxy)-propyltrimethoxysilane.

The resulting nanoparticles, covered with PEG-TFEE, are washed twice and then resuspended in 100 ml of dry toluene. A primary amine was grafted onto the end groups of the PEG chains by adding 1 ml of ethylenediamine (Sigma) to the nanoparticles maintained under a stream of nitrogen. The mixture was ultrasonicated (4 hours, 60° C.). The resulting nanoparticles, covered with the amine, were washed three times with ethanol, and three times with dimethyl sulfoxide (DMSO). The nanoparticles were finally resuspended in 50 ml of anhydrous DMSO. The FA was coupled to the amine end groups of the PEG chains by adding 50 ml of FA solution (23 mM FA in DMSO) with equimolar amounts of dicyclohexylcarbodiimide (DCC) (Sigma) and 10 µL of pyridine. The mixture was protected from light and reacted over night with two-dimensional stirring (180 rpm). The nanoparticles conjugated with PEGH and FA (NP-PEG-FA) were washed twice with ethanol and twice with a 20 mM sodium citrate solution (pH 8.0) and finally resuspended in this same sodium citrate solution.

b) Synthesis 2: Surface Modification During the Synthesis of the Nanoparticles

Surface modification of the MOF solids may also take place during the synthesis.

In the example that follows, the surface modification is performed with chitosan grafted beforehand with folic acid (FA).

An example of synthesis of chitosan grafted with folic acid via a PEG spacer is described in the publication by Peggy Chan et al., *Biomaterials*, Volume 28, Issue 3, 2007, pp. 540-549.

The following reagents were used to perform this example:
- chitosan (molar mass Mn of 255 kDa, viscosity: 200-800 cps in 1% acetic acid, sold by the company Sigma-Aldrich)
- N-hydroxylsuccinimide-PEG-maleimide (NHS-PEG-MAL, Mn 3400 Da, sold by the company Nektar, NOF Corporation, Tokyo, Japan)
- the succinimidyl ester of monomethoxy-PEG (mPEG-SPA, Mn 5000 Da, sold by the company Nektar, NOF Corporation, Tokyo, Japan).

The chitosan is deacetylated beforehand to obtain a degree of acetylation of 82% (determined by $^1$H-NMR) according to the process described by Wang L. S. (Thesis, National University of Singapore, Singapore, 2001).

100 mg of chitosan were dissolved in 50 ml of acetic acid solution (20%). The pH of the solution was adjusted to 6 by adding sodium hydroxide, and mPEG-SPA was introduced into the reaction mixture. The mixture was reacted for 24 hours at room temperature with stirring. The product obtained was dialyzed for 24 hours against deionized water, using a membrane with a cutoff threshold of 12 000 Da (Spectrum Laboratories, USA) and finally lyophilized.

To synthesize the chitosan grafted with PEG and FA, the N-hydroxysuccinimide ester of FA was prepared according to the method described by J. H. Van Steenis et al., *J Control Release* 87 (2003), pp. 167-176.

Briefly, 1 g of FA was added to a mixture of anhydrous DMSO (40 ml) and triethylamine (TEA, 0.5 ml). The mixture was stirred protected from light overnight, under anhydrous conditions. The other reagents, dicyclohexylcarbodiimide (DCC, 0.5 g) and N-hydroxysuccinimide (NHS, 0.52 g) were added and the mixture was reacted for 18 hours protected from light, and under anhydrous conditions. The precipitated by-product, dicyclohexylurea (DCU), was removed by filtration. The DMSO and TFA were evaporated off under vacuum. The reaction product was dried under vacuum and then dissolved in 1.5 ml of a 2/1 (v/v) mixture of DMSO and TEA. An equimolar amount of 2-aminoethanethiol (Wako) was added and the reaction was allowed to continue overnight under anhydrous conditions. Thus, a thiol group was able to be introduced onto the folic acid, and the resulting product is known as FA-SH.

100 mg of chitosan are dissolved in 50 ml of acetic acid solution (20%). The pH of the solution is adjusted to 6 by adding sodium hydroxide, and 100 mg of NHS-PEG-Mal are introduced into the reaction mixture. The mixture is reacted for 3 hours at room temperature with stirring, and the pH is then adjusted to 7. The mixture is reacted overnight, under anhydrous conditions. The FA-SH synthesized as previously was added gradually with stirring and the pH was adjusted to 6.5-7.5 with sodium hydroxide.

The conjugate obtained, known as FA-PEG chi, which bears FA coupled to chitosan via a PEG spacer arm, which is an advantage for reaching the folic acid receptor (as described in the literature, see, for example: A. Gabizon, H. Shmeeda, A. T. Horowitz and S. Zalipsky, Tumor cell targeting of liposome-entrapped drugs with phospholipids-anchored folic acid-PEG conjugates, *Adv Drug Deliv Rev* 56 (2004), pp. 1177-1192).

The degree of substitution may be adjusted by varying the PEG/chitosan mass ratio used in the reaction. This polymer was dialyzed for 48 hours against deionized water using a membrane with a cutoff threshold of 12 000 Da (Spectrum Laboratories, USA) and finally lyophilized.

c) Synthesis 3

The hybrid solids may be surface-modified by adsorption of polysaccharides such as biotin-grafted dextran.

It may thus be envisioned to adsorb, instead of biotin-grafted dextran, folic acid-grafted chitosan (synthesized as described in the publication cited hereinabove) and, optionally, if necessary, also grafted with other hydrophobic compounds such as cholesterol or aliphatic chain units, so as to ensure better adhesion to the surface of the nanoparticles.

Surface functionalization may also take place via adsorption of other FA-grafted polysaccharides.

d) Synthesis 4

The hybrid solids may be surface-modified with PEG during their synthesis. We propose to replace the monomethoxy PEG monoacid used in this synthesis with PEG monoacid comprising a reactive function blocked at the chain end, for instance the commercial product:

Boc-PEG-carbonateNHS, MW 5000, Boc=tert-butoxycarbonyl

Reference SUNBRIGHT® BO-050TS, NOF Corporation

After reaction, as indicated in the example, with the exception that we will use mixtures MeO-PEG-COOH and Boc-PEG-carbonateNHS (mass ratios 1/0.05 to 1/0.5) in place of MeO-PEG-COOH, the deprotection will take place by adding trifluoroacetic acid (TFA).

Possible Protocol:

0.6 ml of TFA is added to a suspension of 300 mg of nanoparticles in 2 ml of water. The mixture is reacted for 1 hour at room temperature with magnetic stirring. The particles are isolated by centrifugation and washed three times with double-distilled water.

The reactive groups at the surface are functionalized with ligands such as FA, for example as in synthesis A.

e) Characterization of the Nanoparticles

The amount of folic acid effectively coupled to the nanoparticles may be determined after degrading them in an acidic medium, neutralizing to pH 7 and then redissolving in a suitable solvent, such as dichloromethane, DMSO or a mixture of these two solvents. The folic acid may then be quantified by measuring the UV absorbance (at 358 nm, the molar extinction coefficient $\varepsilon$ of folic acid is 15.76 $M^{-1} \cdot cm^{-1}$).

To confirm that folic acid is indeed at the surface of the nanoparticles, we may use a technique such as plasmon surface resonance (BIAcore). Folate binding protein will be immobilized on the surface of the detector, on a thin film of activated dextran (standard procedure recommended by the manufacturer BIAcore). The amount of nanoparticles effectively attached to this support will be evaluated relative to that of nanoparticles not covered with folic acid.

Example 27: Formulation of Mixed MOF Solids: Based on Gadolinium and Iron

Two Synthetic Conditions are Possible:

Synthesis 1:

0.028 g (0.5 mmol) of metallic iron powder Fe° (Riedel-de Haën, 99%), 0.225 g of gadolinium(III) nitrate hexahydrate (0.5 mmol, Aldrich, 99.9%) and 0.140 g of 1,3,5-benzenetricarboxylic acid (0.666 mmol, Aldrich, 95%) dispersed in 10 ml of deionized water, the whole left for 24 hours at 180° C. in a 23 ml Teflon body placed in a Paar metallic bomb. The solid is then filtered off and washed with water and then with ethanol.

Synthesis 2:

0.065 g (~0.5 mmol per 1 iron per trimer) of iron(III) acetate (prepared according to the synthesis described in Example 1), 0.225 g of gadolinium(III) nitrate hexahydrate (0.5 mmol, Aldrich, 99.9%) and 0.140 g of 1,3,5-benzenetricarboxylic acid (0.666 mmol, Aldrich, 95%) dispersed in 10 ml of deionized water (or methanol or ethanol or dimethylformamide), the whole left for 12 hours at 150° C. in a 23 ml Teflon body placed in a Paar metallic bomb. The solid is then filtered off and washed with water and then with ethanol.

LIST OF REFERENCES

[1] U.S. patent application Ser. No. 10/039,733
[2] U.S. patent application Ser. No. 10/061,147
[3] U.S. patent application Ser. No. 10/137,043
[4] U.S. Pat. No. 5,648,508
[5] U.S. Pat. No. 6,638,494
[6] Bone Marrow Transplant. 2002, 30 (12), 833-841
[7] U.S. Pat. No. 4,329,332
[8] J. Bouligand, P. Couvreur, A. Layre, A. Deroussent, A. Paci, E. Delain, G. Vassal, R. Graf «Busulfan-loaded long-circulating nanospheres, a very attractive challenge for both galenists and pharmacologists», Int. J. Pharm., 2004
[9] K. Byrapsa, M. Yoshimura, «Handbook of hydrothermal technology», Noyes Publications, Parkridge, N.J., USA, William Andrew Publishing, LLC, Norwich N.Y. USA, 2001
[10] G. Tompsett, W. C. Conner, K. S. Yngvesson, *Chem Phys Chem.* 2006, 7, 296
[11] S.-E. Park, J.-S. Chang, Y. K. Hwang, D. S. Kim, S. H. Jhung, J.-S. Hwang, *Catal. Survey Asia* 2004, 8, 91
[12] C. S. Cundy, *Collect. Czech. Chem. Commun.* 1998, 63, 1699
[13] S. H. Jhung, J.-H. Lee, J.-S. Chang, *Bull. Kor. Chem. Soc.* 2005, 26, 880
[14] A. Pichon, *Cryst. Eng. Comm.* 8, 2006, 211-214

[15] D. Braga, *Angew. Chem. Int. Ed.* 45, 2006, 142-246
[16] D. Braga, *Dalton Trans.*, 2006, 1249-1263.
[17] Sabine Balthasar, Kerstin Michaelis, Norbert Dinauer, Hagen von Briesen, Jörg Kreuter and Klaus Langer, "Preparation and characterisation of antibody modified gelatin nanoparticles as drug carrier system for uptake in lymphocytes", *Biomaterials*, 2005, 26, 15, 2723-2732.
[18] Ruxandra Gref, Patrick Couvreur, Gillian Barratt and Evgueni Mysiakine, "Surface-engineered nanoparticles for multiple ligand coupling", *Biomaterials*, 2003, 24, 24, 4529-4537
[19] Stella B, Marsaud V, Arpicco S, Geraud G, Cattel L, Couvreur P, Renoir J M., "Biological characterization of folic acid-conjugated poly(H2NPEGCA-co-HDCA) nanoparticles in cellular models", *J Drug Target.* 2007, 15(2), 146-53
[20] Hattori Y, Maitani Y., "Folate-linked lipid-based nanoparticle for targeted gene delivery", *Curr Drug Deliv.* 2005, 2(3), 243-52
[21] Mulder W J, Griffioen A W, Strijkers G J, Cormode D P, Nicolay K, Fayad Z A, «Magnetic and fluorescent nanoparticles for multimodality imaging», *Nanomed.* 2007, 2(3), 307-324
[22] A. K. Gupta, R. R. Naregalkar, V. D. Daidya, M. Gupta, «Recent advances on surface engineering or magnetic iron oxide nanoparticles and their biomedical applications», *Nanomed.* 2007, 2(1), 23-39
[23] P Caravan, «Strategies for increasing the sensitivity of gadolinium based MRI contrast agents», *Chem. Soc. Rev.*, 2006, 35, 512-523
[24] Yan-Ping Ren, La-Sheng Long, Bing-Wei Mao, You-Zhu Yuan, Rong-Bin Huang, and Lan-Sun Zheng, *Angew. Chem. Int. Ed.* 2003, 42, No. 5, 532
[25] C. T. Dziobkowski, T. J. Wrobleski, D. B. Brown, *Inorg. Chem.*, 1982, 21, 671
[26] C. Serre, F. Millange, C. Thouvenot, M. Nogues, G. Marsolier, D. Loüer, G. Férey *J. Am. Chem. Soc.*, 2002, 124, 13519
[27] T. Loiseau, C. Mellot-Draznieks, H. Muggera, G. Férey, M. Haouas, F. Taulelle, *C.R. Acad. Sci*, 2005, 8, 765
[28] C. Serre, F. Millange, S. Surblé, G. Férey *Angew. Chem. Int. Ed.* 2004, 43, 6286
[29] Suzy Surblé, Christian Serre, Caroline Mellot-Draznieks, Franck Millange, and Gérard Férey: *Chem. Comm.* 2006 284-286
[30] C. Serre, C. Mellot-Draznieks, S. Surblé, N. Audebrand, Y. Fillinchuk and G. Férey: *Science*, 2007, 315, 1828
[31] C. Mellot-Draznieks, C. Serre, S. Surblé, N. Audebrand and G. Férey: *J. Am. Chem. Soc.*, 2005, 127, 16273-16278
[32] Sung Hwa Jhung, Jin-Ho Lee, Ji Woong Yoon, Christian Serre, Gérard Férey and Jong-San Chang «Facile Synthesis of the Chromium Terephthalate MIL-101 with Giant Pores and Its Sorption Ability for Benzene», *Adv. Mater,* 2006, 19(1), 121-124.
[33] B. Baleux, G. Champetier "Chimie analytique-dosage colorimétrique d'agents de surface non ioniques polyoxyéthylenes à l'aide d'une solution iode-iodurée [Analytical chemistry—colorimetric assay of nonionic polyoxyethylene surface agents using an iodine-iodide solution]", *C.R. Acad. Sciences Paris*, 1972, series C, 274, 1617-1620
[34] R. Gref, M. Lück, P. Quellec, M. Marchand, E. Dellacherie, S. Harnisch, T. Blunk and R. H. Müller, "Stealth" corona-core nanoparticles surface modified by polyethylene glycol (PEG): influences of the corona (PEG chain length and surface density) and of the core composition on phagocytic uptake and plasma protein adsorption", *Colloids and Surfaces B: Biointerfaces*, 2000, 18, 3-4, 301-313
[35] G. Oros, T. Cserhati, E. Forgacs, *Chemosphere* 52, 2003, 185
[36] A. M. Badawi, E. M. S. Azzam, S. M. I. Morsy, *Bioorg. Med. Chem.*, 14, 2006, 8661
[37] W.-J. Tsai, Y.-J Shiao, S-J Lin, W-F Chiou, L-C Lin, T-H Yang, C-M Teng, T-S Wu, L-M Yang, *Bioorg. Med. Chem. Letters* 16, 2006, 4440
[38] Kim, Y.; Swager, T. M. *Chem. Commun.*, 2005, 372-374
[39] L. Anzalone, J. A. Hirsch, *J. Org. Chem.*, 1985, 50, 2128-213
[40] Shiotani Akinori, Z. Naturforsch. 1994, 49, 12, 1731-1736
[41] Ameerunisha et al., *J. Chem. Soc. Perkin Trans.* 2, 1679, 1995
[42] Kohler N, Fryxell G E, Zhang M Q. A bifunctional poly(ethylene glycol)silane immobilized on metallic oxide-based nanoparticles for conjugation with cell targeting agents. *J Am Chem Soc* 2004; 126: 7206-7211
[43] Peggy Chan, Motoichi Kurisawa, Joo Eun Chung, Yi-Yan Yang, Synthesis and characterization of chitosan-g-poly(ethylene glycol)-folate as a non-viral carrier for tumor-targeted gene delivery, *Biomaterials*, Volume 28, Issue 3, 2007, pp 540-549
[44] Wang L S. Polyelectrolyte complex (PEC) membrane composed of chitosan and alginate for wound dressing application. Thesis, National University of Singapore, Singapore, 2001.
[45] J. H. Van Steenis, E. M. van Maarseveen, F. J. Verbaan, R. Verrijk, D. J. A. Crommelin and G. Storm et al., Preparation and characterization of folate-targeted PEG-coated pDMAEMA-based polyplexes, *J Control Release* 87 (2003), pp. 167-176.
[46] Roch et al, *J Chem Phys* 110, 5403-5411, 1999
[47] Kathryn E. Luker and Gary D. Luker, Applications of bioluminescence imaging to antiviral research and therapy: Multiple luciferase enzymes and quantitation, Antiviral Research, Volume 78, Issue 3, June 2008, Pages 179-187

The invention claimed is:
1. A process for preparing isoreticular porous crystalline MOF nanoparticles comprising a three-dimensional succession of units having formula (I) below:

$$Fe_mO_kX_lL_p \qquad \text{Formula (I)}$$

in which:
Fe represents the metallic ion $Fe^{3+}$ or $Fe^{2+}$;
m is 1 to 4;
k is 0 to 4;
l is 0 to 4;
p is 1 to 4;
X is a ligand chosen from the group comprising $OH^-$, $Cl^-$, $F^-$, $I^-$, $Br^-$, $SO_4^{2-}$, $NO_3^-$, $ClO_4^-$, $PF_6^-$, $BF_3^-$, $R^1$—$(COO)_n^-$, $R^1$—$(SO_3)_n^-$, $R^1$—$(PO_3)_n^-$, in which $R^1$ is a hydrogen atom, an optionally substituted, linear or branched $C_1$ to $C_{12}$ alkyl, n=1 to 4;
L is a spacer ligand comprising a radical R bearing q carboxylate groups

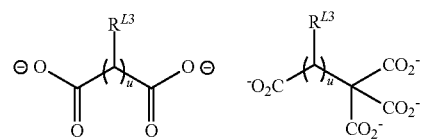

-continued

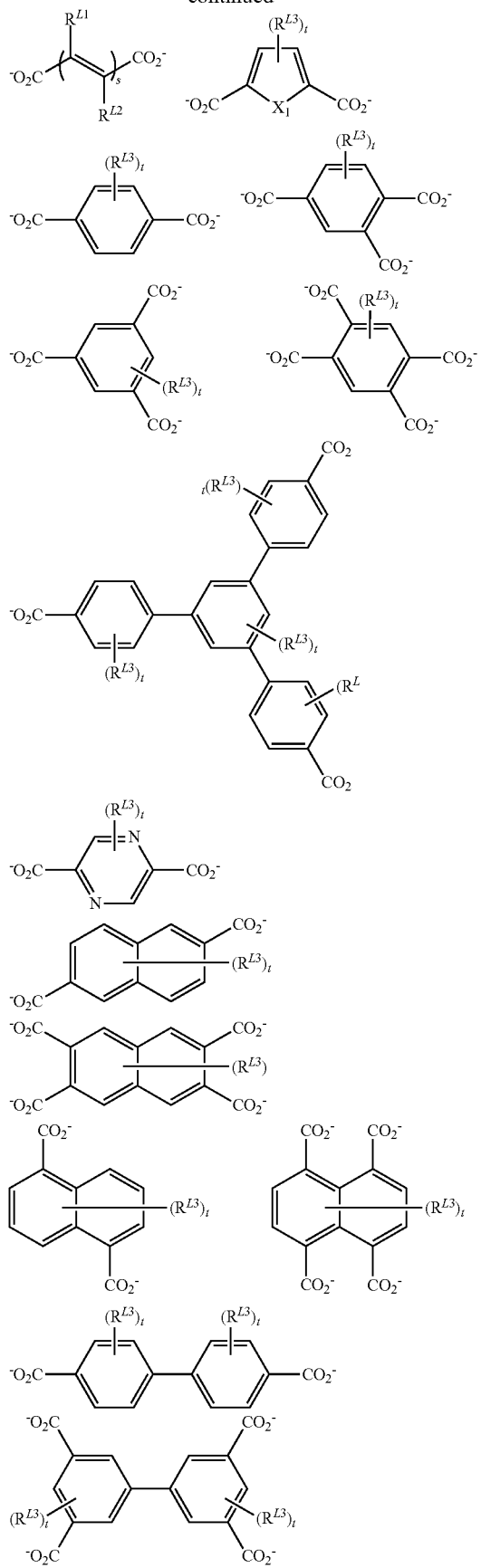
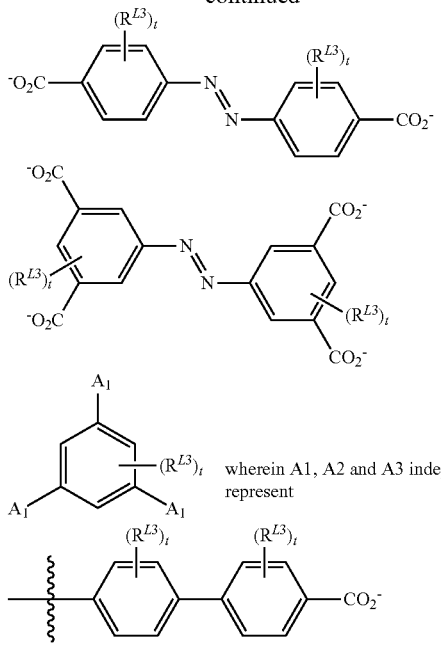

in which
q is 1, 2, 3, 4, 5 or 6;
* denotes the point of attachment of the carboxylate to the radical R;
# denotes the possible points of attachment of the carboxylate to the metal ion;
R represents:
(i) a $C_{1-12}$alkyl, $C_{2-12}$alkene or $C_{2-12}$alkyne radical;
(ii) a fused or non-fused monocyclic or polycyclic aryl radical, comprising 6 to 50 carbon atoms;
(iii) a fused or non-fused monocyclic or polycyclic heteroaryl, comprising 1 to 50 carbon atoms;
(iv) an organic radical comprising a metal element chosen from the group comprising ferrocene, porphyrin, phthalocyanin and a Schiff's base $R^{X1}R^{X2}$—C=N—$R^{X3}$,
in which $R^{X1}$ and $R^{X2}$ are independently a hydrogen atom, a linear, branched or cyclic, optionally substituted $C_{1-12}$alkyl, $C_{2-12}$alkene or $C_{2-12}$alkyne radical, or an optionally branched and/or substituted monocyclic or polycyclic aryl comprising 6 to 50 carbon atoms;
and $R^{X3}$ is a linear, branched or cyclic, optionally substituted $C_{1-12}$alkyl, $C_{2-12}$alkene or $C_{2-12}$alkyne radical, or an optionally branched and/or substituted monocyclic or polycyclic aryl comprising 6 to 50 carbon atoms;
the radical R being optionally substituted with one or more groups $R^2$ independently chosen from the group comprising $C_{1-10}$alkyl; $C_{2-10}$alkene; $C_{2-10}$alkyne; $C_{3-10}$cycloalkyl; $C_{1-10}$heteroalkyl; $C_{1-10}$haloalkyl; $C_{6-10}$aryl; $C_{3-10}$heteroaryl; $C_{5-20}$heterocycle; $C_{1-10}$alkyl$C_{6-10}$aryl; $C_{1-10}$alkyl$C_{3-10}$heteroaryl; $C_{1-10}$alkoxy; $C_{6-10}$aryloxy; $C_{3-10}$heteroalkoxy; $C_{3-10}$heteroaryloxy; $C_{1-10}$alkylthio; $C_{6-10}$arylthio; $C_{1-10}$heteroalkylthio; $C_{3-10}$heteroarylthio; F; Cl; Br; I; —$NO_2$; —CN; —$CF_3$; —$CH_2CF_3$; —$CHCl_2$; —OH; —$CH_2OH$; —$CH_2CH_2OH$; —$NH_2$; —$CH_2NH_2$; —NHCOH; —COOH; —$CONH_2$; —$SO_3H$; —$CH_2SO_2CH_3$; —$PO_3H_2$; —$B(OR^{G1})_2$; or a function -$GR^{G1}$ in which G is —O—, —S—, —$NR^{G2}$—, —C(=O)—, —S(=O)—, —$SO_2$—, —C(=O)O—, —C(=O)$NR^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, —NR$^{G2}$C(=S)—, —SC(=S)NR$^{G2}$—, —NR$^{G2}$C(=S)S—, —NR$^{G2}$C(=S)NR$^{G2}$—, —SC(=NR$^{G2}$)—, —C(=S)NR$^{G2}$—, —OC(=S)NR$^{G2}$—, —NR$^{G2}$C(=S)O—, —SC(=O)NR$^{G2}$—, —NR$^{G2}$C(=O)S—, —C(=O)S—, —SC(=O)—, —SC(=O)S—, —C(=S)O—, —OC(=S)—, —OC(=S)O— or —SO$_2$NR$^{G2}$—, in which each occurrence of R$^{G1}$, R$^{G2}$ and R$^{G3}$ is, independently of the other occurrences of R$^{G1}$, a hydrogen atom; a halogen atom; or a linear, branched or cyclic, optionally substituted $C_{1-12}$alkyl, $C_{1-12}$heteroalkyl, $C_{2-10}$alkene or $C_{2-10}$alkyne group; or a group $C_{6-10}$aryl, $C_{3-10}$heteroaryl, $C_{5-10}$heterocycle, $C_{1-10}$alkyl$C_{6-10}$aryl or $C_{1-10}$alkyl$C_{3-10}$heteroaryl in which the aryl, heteroaryl or heterocyclic radical is optionally substituted; or alternatively, when G represents —NR$^{G2}$—, R$^{G1}$ and R$^{G2}$ together with the nitrogen atom to which they are attached form an optionally substituted heterocycle or heteroaryl;

the process comprising at least one reaction step (i) that consists in mixing in a polar solvent:
- at least one solution comprising at least one metallic inorganic precursor in the form of iron metal, an iron(III) salt, an iron(II) salt or a coordination complex comprising the metal ion $Fe^{3+}$,
- at least one ligand L' comprising a di-, tri-, tetra- or hexadentate ligand selected from the group consisting of:

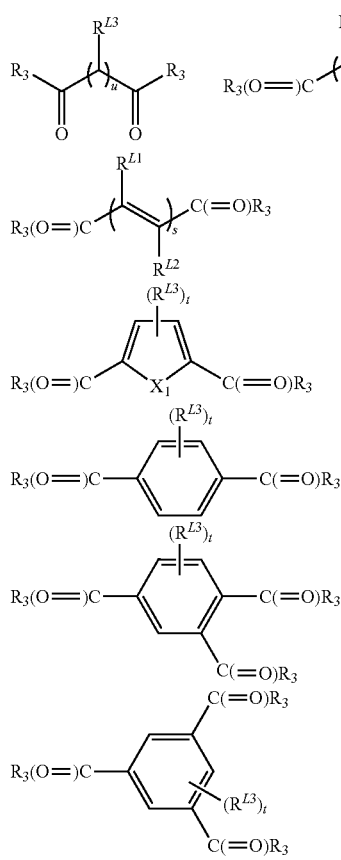

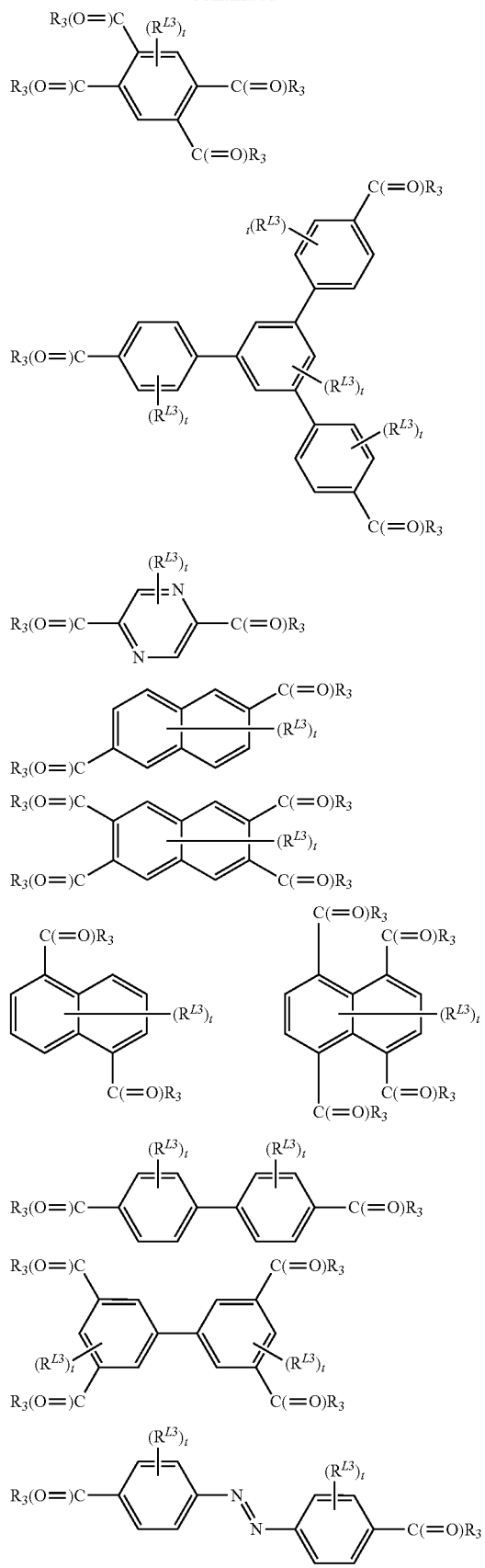

-continued

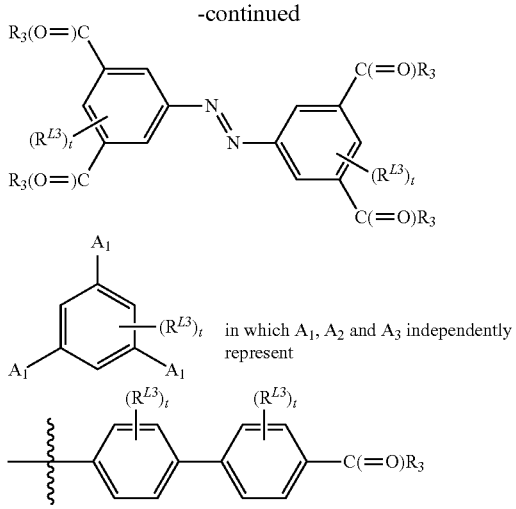

In which
R³ is selected from the group consisting of a radical —OH, a radical —OY in which Y represents an alkali metal cation, a halogen or a radical —OR⁴, —O—C(=O)R⁴ or —NR⁴R⁴', in which R⁴ and R⁴', identical or different, represent $C_{1-12}$ alkyl radicals,
$X_1$ represents O or S,
s represents an integer from 1 to 4,
each occurrence of t independently represents an integer from 1 to 4,
u represents an integer from 1 to 7,
$R^{L1}$ and $R^{L2}$ independently represent H, a halogen or a $C_1$ to $C_6$ alkyl, and
each occurrence of $R^{L3}$ independently represents H, a halogen, OH, $NH_2$, $NO_2$ or a $C_1$ to $C_6$ alkyl,
so as to obtain the said nanoparticles, wherein,
when the process is carried out via the solvothermal route, the reaction temperature is between 20 and 200° C., the reaction time is between 30 minutes and 72 hours, the concentration of ligand L' and of metallic inorganic precursor is—between 1 and 200 mmol/L, a monocarboxylic acid cosolvent is added in the course of synthesis of the MOF nanoparticle to stop crystal growth of the MOF nanoparticle, before the end of the synthesis; and
when the process is carried out via the ultrasonication route, the reaction temperature is between −5° C. and 20° C., the reaction time is between 15 minutes and 2 hours, the concentration of ligand L' and of metallic inorganic precursor is between 10 mol/l and $10^{-2}$ mol/l, and a monocarboxylic acid is added.

2. The process for preparing nanoparticles as claimed in claim 1, in which the ligand L' used represents a di-, tri- or tetracarboxylic acid selected from the group consisting of: $C_2H_2(CO_2H)_2$ (fumaric acid), $C_2H_4(CO_2H)_2$ (succinic acid), $C_3H_6(CO_2H)_2$ (glutaric acid), $C_4H_4(CO_2H)_2$ (muconic acid), $C_4H_8(CO_2H)_2$ (adipic acid), $C_7H_{14}(CO_2H)_2$ (azelaic acid), $C_5H_3S(CO_2H)_2$ (2,5-thiophenedicarboxylic acid), $C_6H_4(CO_2H)_2$ (terephthalic acid), $C_6H_2N_2(CO_2H)_2$ (2,5-pyrazinedicarboxylic acid), $C_{10}H_6(CO_2H)_2$ (naphthalene-2,6-dicarboxylic acid), $C_{12}H_8(CO_2H)_2$ (biphenyl-4,4'-dicarboxylic acid), $C_{12}H_8N_2(CO_2H)_2$ (azobenzenedicarboxylic acid), $C_6H_3(CO_2H)_3$ (benzene-1,2,4-tricarboxylic acid), $C_6H_3(CO_2H)_3$ (benzene-1,3,5-tricarboxylate acid), $C_{24}H_{15}(CO_2H)_3$ (benzene-1,3,5-tribenzoic acid), $C_6H_2(CO_2H)_4$ (benzene-1,2,4,5-tetracarboxylic acid), $C_{10}H_4(CO_2H)_4$ (naphthalene-2,3,6,7-tetracarboxylic acid), $C_{10}H_4(CO_2H)_4$ (naphthalene-1,4,5,8-tetracarboxylic acid), $C_{12}H_6(CO_2H)_4$ (biphenyl-3,5,3',5'-tetracarboxylic acid), and modified analogs chosen from the group comprising 2-aminoterephthalic acid, 2-nitroterephthalic acid, 2-methylterephthalic acid, 2-chloroterephthalic acid, 2-bromoterephthalic acid, 2,5-dihydroxoterephthalic acid, tetrafluoroterephthalic acid, 2,5-dicarboxyterephthalic acid, dimethyl-4,4'-biphenyldicarboxylic acid, tetramethyl-4,4'-biphenyldicarboxylic acid, dicarboxy-4,4'-biphenyldicarboxylic acid, 2,5-pyrazinedicarboxylic acid, 2,5-diperfluoroterephthalic acid, azobenzene-4,4'-dicarboxylic acid, 3,3'-dichloroazobenzene-4,4'-dicarboxylic acid, 3,3'-dihydroxoazobenzene-4,4'-dicarboxylic acid, 3,3'-diperfluoroazobenzene-4,4'-dicarboxylic acid, 3,5,3',5'-azobenzenetetracarboxylic acid, 2,5-dimethylterephthalic acid, and perfluoroglutaric acid.

3. The process for preparing nanoparticles as claimed in claim 1, in which the reaction step (i) is performed with at least one of the reaction conditions below:
  (a) a reaction temperature from 0° C. to 220° C.;
  (b) a stirring speed from 0 to 1000 rpm;
  (c) a reaction time from 1 minute to 96 hours;
  (d) a pH from 0 to 7;
  (e) the addition of at least one monocarboxylic acid cosolvent to the solvent, to the precursor, to the ligand or to the mixture thereof, said monocarboxylic acid cosolvent being selected from the group consisting of acetic acid, formic acid and benzoic acid;
  (f) the solvent is selected from the group consisting of water, alcohols $R^S$—OH in which $R^S$ is a linear or branched $C_1$ to $C_6$ alkyl radical, dimethylformamide, dimethyl sulfoxide, acetonitrile, tetrahydrofuran, diethylformamide, chloroform, cyclohexane, acetone, cyanobenzene, dichloromethane, nitrobenzene, ethylene glycol, dimethylacetamide, and mixtures of these solvents, which may be miscible or immiscible;
  (g) in a supercritical medium;
  (h) under microwaves and/or under ultrasound;
  (i) under electrochemical electrolysis conditions;
  (j) under conditions using a roll mill;
  (k) in a gas stream.

4. The process for preparing nanoparticles as claimed in claim 1, further comprising a step (ii) of introducing into said nanoparticle at least one molecule of interest which may be a pharmaceutically active principle and/or a compound of cosmetic interest and/or marker.

5. The process for preparing nanoparticles as claimed in claim 4, further comprising a step (iii) of binding to said nanoparticle at least one organic surface agent selected from the group consisting of an oligosaccharide, a polysaccharide, a glycosaminoglycan, a polymer, a surfactant, a vitamin, a coenzyme, an antibody or antibody fragment, an amino acid and a peptide.

* * * * *